(12) United States Patent
Chen et al.

(10) Patent No.: US 8,778,973 B2
(45) Date of Patent: Jul. 15, 2014

(54) ALKENE OXINDOLE DERIVATIVES

(71) Applicant: Hoffmann-La Roche Inc., Nutley, NJ (US)

(72) Inventors: Li Chen, Shanghai (CN); Lichun Feng, Shanghai (CN); Mengwei Huang, Shanghai (CN); Jia Li, Shanghai (CN); Fajun Nan, Shanghai (CN); Tao Pang, Jiangsu (CN); Lifang Yu, Chicago, IL (US); Mei Zhang, Shanghai (CN)

(73) Assignee: Hoffmann-LaRoche Inc., Nutley, NY (US)

( * ) Notice: Subject to any disclaimer, the term of this patent is extended or adjusted under 35 U.S.C. 154(b) by 2 days.

(21) Appl. No.: 13/744,480

(22) Filed: Jan. 18, 2013

(65) Prior Publication Data

US 2013/0131114 A1 May 23, 2013

Related U.S. Application Data

(63) Continuation of application No. 12/881,211, filed on Sep. 14, 2010, now abandoned.

(30) Foreign Application Priority Data

Sep. 21, 2009 (WO) ................ PCT/CN2009/074060

(51) Int. Cl.
*A61K 31/44* (2006.01)
(52) U.S. Cl.
USPC ............................ 514/339; 514/418; 514/414
(58) Field of Classification Search
USPC .......................................... 514/339, 418, 414
See application file for complete search history.

(56) References Cited

U.S. PATENT DOCUMENTS 5,977,130 A 11/1999 Sato et al.
7,799,782 B2 * 9/2010 Munson et al. ............ 514/234.5

FOREIGN PATENT DOCUMENTS

EP 1935883 6/2008
WO 98/50356 11/1998
WO 2008/033562 3/2008

OTHER PUBLICATIONS

Friedman et al., "Nature" 395:763-770 ( 1998).
Fryer et al., "The Journal of Biological Chem." 277:25226-25232 ( 2002).
Woods et al., "Molecular & Cellular Biology" 20:6704-6711 ( 2000).
Semple et al., "The Journal of Clinical Investigation" 116:581-589 ( 2006).
Ansel et al., "Pharm. Dosage Forms & Drug Delivery Systems":456-457 ( 1995).
Bastin et al., "Organic Process Research & Development" 4:427-435 ( 2000).
Minokoshi et al., "Nature" 415:339-343 ( 2002).
Muoio et al., "Diabetes" 46:1360-1363 ( 1997).
Cheung et al., J. Org. Chem. 70:3741-3744 ( 2005).
Zhou et al., "The Journal of Clinical Investigation" 108:1167-1174 ( 2001).
Yamauchi et al., "Nature Medicine" 7:941-946 ( 2001).
Owen et al., The Biochemical Journal 348(Part 3):607-614 ( 2000).
Shaw et al., "Science (New York) NY" 310:1642-1646 ( 2005).
Pang et al., "The Journal of Biological Chemistry" 283:16051-16060 ( 2008).
Hardie et al., "Nature Reviews Molecular Cell Biology" 8:774-785 ( 2007).
Kadowaki et al., "The Journal of Clinical Investigation" 116:1784-1792 ( 2006).
Yamauchi et al., "Nature Medicine" 8:1288-1295 ( 2002).
Tang et al., CAS 149:176121 ( 2008).
Carling et al., "Trends in Biochem. Science" 29:18-24 ( 2004).
Long et al., "The Journal of Clinical Investigation" 116:1776-1783 ( 2006).
Hardie et al., "Annual Review of Pharmacology & Toxicology" 47:185-210 ( 2007).
Deng et al., Organic Letters 9(25):5207-5210 ( 2007).
Kahn et al., "Cell Metabolism" 1:15-25 ( 2005).
Song et al., Tetrahedron Letters (Examiner cited), 50(27):3912-3916 ( 2009).
Pinto et al., Organic Letters:4927-4930 ( 2006).
Cool et al., "Cell Metabolism" 3:403-416 ( 2006).
El-Mir et al., "The Journal of Biological Chemistry" 275:223-228 ( 2000).
Yanada et al., J. Org. Chem. 70:6972-6975 ( 2005).
The English translation of the Chinese Office Action, issued on Jul. 8, 2013, in the corresponding Chinese application No. 201080041819. 2., pp. 11.

* cited by examiner

*Primary Examiner* — Rei-tsang Shiao

(57) ABSTRACT

The present invention provides compounds of formula (I),

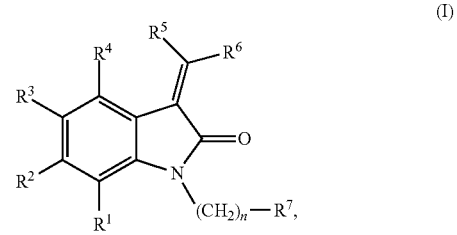

as well as pharmaceutically acceptable salt thereof, wherein $R^1$ to $R^7$ have the significance given herein. The compounds are useful in the treatment of prophylaxis of diseases that are related to AMPK regulation.

31 Claims, No Drawings

ALKENE OXINDOLE DERIVATIVES

PRIORITY TO RELATED APPLICATION(S)

This application is a continuation application of U.S. Ser. No. 12/881,211, filed Sep. 14, 2010, and claims the benefit of International Patent Application No. PCT/CN2009/074060, filed Sep. 21, 2009, which are hereby incorporated by reference in their entirety.

FIELD OF THE INVENTION

The invention relates to compounds which are activators of AMP-activated protein kinase (AMPK) and which are useful in the treatment or prophylaxis of diseases that are related to AMPK regulation, such as obesity, dyslipidemia, hyperglycemia, type 1 or type 2 diabetes.

BACKGROUND OF THE INVENTION

Obesity and type 2 diabetes, hypertension and cardiovascular disease, are diseases that feature serious disturbances in glucose and lipid metabolism that severely affect the health and quality of life of affected individuals. The increasing prevalence of these diseases makes finding new drug targets for treating this syndrome an urgent task.

AMP-activated protein kinase acts as a cellular energy sensor and regulator. It is activated by an increase in the cellular AMP:ATP ratio induced by metabolic stress. Once activated, AMPK switches on catabolic pathways that generate ATP and switches off ATP-consuming anabolic pathways by acute regulation of the activity of key enzymes in metabolism and chronic regulation of the expression of pivotal transcription factors (Hardie, D G. Nature Reviews 8 (2007b), 774-785; Woods, A et al. Molecular and Cellular Biology 20 (2000), 6704-6711). The growing evidence of AMPK regulatory effects on glucose and lipid metabolism makes it a potential drug target for treatment of diabetes and metabolic syndrome (Carling, D. Trends Biochem Sci 29 (2004), 18-24; Hardie, D G. Annual Review of Pharmacology and Toxicology 47 (2007a), 185-210; Kahn, B B et al. Cell Metabolism 1 (2005), 15-25; Long, Y C et al. The Journal of Clinical Investigation 116 (2006), 1776-1783).

At the physiological level, this concept has been supported by two adipokines, leptin and adiponectin, both of which exert excellent effects on glucose and lipid metabolism (Friedman, J M and Halaas, J L. Nature 395 (1998), 763-770; Muoio, D M et al. Diabetes 46 (1997), 1360-1363; Yamauchi, T et al. Nature Medicine 7 (2001), 941-946). Recent studies suggest that leptin and adiponectin exert their antidiabetic effects by activating AMPK. Leptin stimulates muscle fatty acid oxidation by activating AMPK directly and through a hypothalamic-adrenergic pathway (Minokoshi, Y et al. Nature 415 (2002), 339-343). Adiponectin stimulates glucose uptake and fatty acid oxidation in vitro by activation of AMPK. Furthermore, it exerts its hypoglycemic effect by decreasing PEPCK and G6Pase expression, whereas the administration of dominant negative α1 adenovirus reverses the effect in vivo (Yamauchi, T et al. Nature Medicine 8 (2002), 1288-1295).

At the pharmacological level, the concept of AMPK as a potential target for treating metabolic syndrome has been further supported by the discovery of two major classes of existing antidiabetic drugs: thiazolidinediones (rosiglitazone, troglitazone and pioglitazone) and biguanides (metformin and phenformin) activate AMPK in cultured cells and in vivo. Rosiglitazone is traditionally considered to be a PPARγ agonist and exerts its antidiabetic effects through differentiation of adipocytes (Semple, R K et al. The Journal of clinical investigation 116 (2006), 581-589). Recent findings indicate that AMPK may be involved in the antidiabetic effects of rosiglitazone (Brunmair, B et al. The Journal of Biological Chemistry 277 (2002), 25226-25232; Kadowaki, T et al. The Journal of Clinical Investigation 116 (2006), 1784-1792). In the case of metformin, an existing antidiabetic agent without a defined mechanism of action, recent studies demonstrate that it could activate AMPK in vitro and in vivo by inhibiting complex I (El-Mir, M Y et al. The Journal of Biological Chemistry 275 (2000), 223-228; Owen, M R et al. The Biochemical Journal 348 Pt 3 (2000), 607-614; Zhou, G et al. The Journal of Clinical Investigation 108 (2001), 1167-1174), and the hypoglycemic effect could be blocked completely by knockout of its upstream kinase LKB1, confirming the key role of AMPK in mediating the antidiabetic effect of metformin (Shaw, R J et al. Science (New York) N.Y. 310 (2005), 1642-1646).

Most recently, Cool and coworkers have identified a small direct AMPK activator, A-769662, which exerts antidiabetic effects in vivo (Cool, B et al. Cell Metabolism 3 (2006), 403-416). Jia Li's laboratory has identified a small AMPK activator, PT1, which activates the inactive forms of AMPK α2398 and α1394 with micromolar activity and exerts some cellular effects (Pang, T et al. The Journal of Biological Chemistry 283 (2008), 16051-16060).

It has been found that the compounds of the present invention are potent AMPK activators. The compounds of the invention are therefore useful in the treatment or prophylaxis of diseases that are related to AMPK regulation, such as obesity, dyslipidemia, hyperglycemia, type 1 or type 2 diabetes.

SUMMARY OF THE INVENTION

The present invention relates to a compound of formula (I),

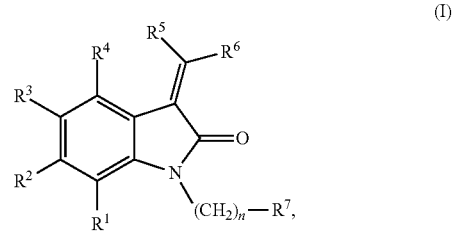

wherein
$R^1$ is selected from the group consisting of: hydrogen, halogen, alkoxy, cyano, haloalkyl, alkylsulfanyl, aminosulfonyl, alkylsulfonyl, haloalkoxy and alkylcarbonyl;
$R^2$ is selected from the group consisting of: hydrogen, halogen, alkoxy, cyano, haloalkyl, alkylsulfanyl, aminosulfonyl, alkylsulfonyl, haloalkoxy and alkylcarbonyl;
$R^3$ is selected from the group consisting of: hydrogen, halogen, alkoxy, cyano, haloalkyl, alkylsulfanyl, aminosulfonyl, alkylsulfonyl, haloalkoxy and alkylcarbonyl;
$R^4$ is selected from the group consisting of: hydrogen, halogen, alkoxy, cyano, haloalkyl, alkylsulfanyl, aminosulfonyl, alkylsulfonyl, haloalkoxy and alkylcarbonyl;
$R^5$ is selected from the group consisting of: alkyl, hydroxyalkyl, cycloalkyl, phenylalkyl, halophenylalkyl, phenyl, substituted phenyl, thiophenyl and pyridinyl, wherein said substituted phenyl is phenyl substituted with one to three substituents independently selected from the group consisting of alkyl, alkoxy, halogen, cyano, haloalkyl, alkylsulfanyl, aminosulfonyl, alkylsulfonyl, haloalkoxy and alkylcarbonyl;

$R^6$ is selected from the group consisting of: alkyl, hydroxyalkyl, cycloalkyl, phenylalkyl, halophenylalkyl, phenyl, substituted phenyl, thiophenyl and pyridinyl, wherein said substituted phenyl is phenyl substituted with one to three substituents independently selected from the group consisting of alkyl, alkoxy, halogen, cyano, haloalkyl, alkylsulfanyl, aminosulfonyl, alkylsulfonyl, haloalkoxy and alkylcarbonyl;

$R^7$ is selected from the group consisting of: substituted phenyl, pyridinyl, substituted pyridinyl, thiazolyl, substituted thiazolyl and carboxy, wherein said substituted phenyl is phenyl substituted with one to three substituents independently selected from the group consisting of alkyl, hydroxy, alkoxy, carboxy, alkoxycarbonylalkyl, alkylaminocarbonyl, carboxyalkoxy, alkoxycarbonyl, alkoxycarbonylalkoxy and alkylsulfonylaminocarbonyl, and said substituted pyridinyl and said substituted thiazolyl are, respectively, pyridinyl and thiazolyl substituted with alkoxycarbonyl or carboxy; and n is 0 or 1;

or a pharmaceutically acceptable salt or ester thereof;

with the provisos that:

$R^5$ and $R^6$ are not both methoxyphenyl at the same time; and when one of $R^5$ and $R^6$ is phenyl and the other one is phenyl, methylphenyl or alkoxyphenyl, $R^7$ is alkoxycarbonylphenyl.

The invention also relates to a pharmaceutical composition comprising a compound of formula I, or a pharmaceutically acceptable salt or ester thereof, and a therapeutically inert carrier.

The invention also relates to a process for the manufacture of these novel compounds and medicaments containing them.

The compounds of the invention have an activation effect on AMP (adenosine monophosphate)-activated protein kinase, which results in lowered blood glucose. The invention thus also concerns the use of such compounds for the treatment or prophylaxis of diseases that are related to AMPK regulation, such as obesity, dyslipidemia, hyperglycemia, type 1 or type 2 diabetes.

DETAILS DESCRIPTION OF THE INVENTION

The present invention relates to a compound of formula (I),

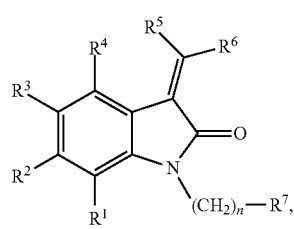

(I)

wherein $R^1$ is selected from the group consisting of: hydrogen, halogen, alkoxy, cyano, haloalkyl, alkylsulfanyl, aminosulfonyl, alkylsulfonyl, haloalkoxy and alkylcarbonyl;

$R^2$ is selected from the group consisting of: hydrogen, halogen, alkoxy, cyano, haloalkyl, alkylsulfanyl, aminosulfonyl, alkylsulfonyl, haloalkoxy and alkylcarbonyl;

$R^3$ is selected from the group consisting of: hydrogen, halogen, alkoxy, cyano, haloalkyl, alkylsulfanyl, aminosulfonyl, alkylsulfonyl, haloalkoxy and alkylcarbonyl;

$R^4$ is selected from the group consisting of: hydrogen, halogen, alkoxy, cyano, haloalkyl, alkylsulfanyl, aminosulfonyl, alkylsulfonyl, haloalkoxy and alkylcarbonyl;

$R^5$ is selected from the group consisting of: alkyl, hydroxyalkyl, cycloalkyl, phenylalkyl, halophenylalkyl, phenyl, substituted phenyl, thiophenyl and pyridinyl, wherein said substituted phenyl is phenyl substituted with one to three substituents independently selected from the group consisting of alkyl, alkoxy, halogen, cyano, haloalkyl, alkylsulfanyl, aminosulfonyl, alkylsulfonyl, haloalkoxy and alkylcarbonyl;

$R^6$ is selected from the group consisting of: alkyl, hydroxyalkyl, cycloalkyl, phenylalkyl, halophenylalkyl, phenyl, substituted phenyl, thiophenyl and pyridinyl, wherein said substituted phenyl is phenyl substituted with one to three substituents independently selected from the group consisting of alkyl, alkoxy, halogen, cyano, haloalkyl, alkylsulfanyl, aminosulfonyl, alkylsulfonyl, haloalkoxy and alkylcarbonyl;

$R^7$ is selected from the group consisting of: substituted phenyl, pyridinyl, substituted pyridinyl, thiazolyl, substituted thiazolyl and carboxy, wherein said substituted phenyl is phenyl substituted with one to three substituents independently selected from the group consisting of alkyl, hydroxy, alkoxy, carboxy, alkoxycarbonylalkyl, alkylaminocarbonyl, carboxyalkoxy, alkoxycarbonyl, alkoxycarbonylalkoxy and alkylsulfonylaminocarbonyl, and said substituted pyridinyl and said substituted thiazolyl are, respectively, pyridinyl and thiazolyl substituted with alkoxycarbonyl or carboxy; and n is 0 or 1;

or a pharmaceutically acceptable salt or ester thereof;

with the provisos that:

$R^5$ and $R^6$ are not both methoxyphenyl at the same time; and when one of $R^5$ and $R^6$ is phenyl and the other one is phenyl, methylphenyl or alkoxyphenyl, $R^7$ is alkoxycarbonylphenyl.

The compounds of the invention have an activation effect on AMP (adenosine monophosphate)-activated protein kinase, which results in lowered blood glucose.

As used herein, the term "alkyl" alone or in combination signifies a saturated, linear- or branched chain alkyl group containing 1 to 8, preferably 1 to 6, more preferably 1 to 4 carbon atoms, for example methyl, ethyl, propyl, isopropyl, 1-butyl, 2-butyl and tert-butyl. Preferred "alkyl" groups are methyl, ethyl, isopropyl and tert-butyl.

The term "alkoxy" alone or in combination signifies a group alkyl-O—, wherein the "alkyl" is as defined above; for example methoxy, ethoxy, propoxy, isopropoxy, n-butoxy, i-butoxy, 2-butoxy and t-butoxy. Preferred alkoxy groups are methoxy and ethoxy and more preferably methoxy.

The term "cycloalkyl" alone or in combination refers to a saturated carbon ring containing from 3 to 7 carbon atoms, preferably from 3 to 6 carbon atoms, for example, cyclopropyl, cyclobutyl, cyclopentyl, cyclohexyl and cycloheptyl. A preferred cycloalkyl group is cyclohexyl.

The term "halogen" means fluorine, chlorine, bromine or iodine. Halogen is preferably fluorine or chlorine.

The term "carboxy" alone or in combination refers to the group —COOH.

The term "carbonyl" alone or in combination refers to the group —C(O)—.

The term "amino" alone or in combination refers to primary (—$NH_2$—), secondary (—NH—) or tertiary amino (—N—).

The term "alkylsulfanyl" alone or in combination refers to the group —S-alkyl.

The term "sulfonyl" alone or in combination refers to the group —S(O)$_2$—.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et. al., Organic Process Research & Development 2000, 4, 427-435; or in Ansel, H., et. al., In: Pharmaceutical Dosage Forms and Drug Delivery Systems, 6th ed. (1995), pp. 196 and 1456-1457. Preferred are the sodium salts of the compounds of formula (I).

"Pharmaceutically acceptable esters" means that compounds of formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention. Preferred are the methyl and ethyl esters of the compounds of formula (I).

Preferred is a compound according of formula (I) wherein $R^1$ is selected from the group consisting of: hydrogen, halogen and alkoxy.

Further preferred is a compound of formula (I) wherein $R^1$ is selected from the group consisting of: hydrogen, fluoro and chloro.

Still further preferred is a compound of formula (I) wherein $R^1$ is hydrogen.

A compound of formula (I) wherein $R^2$ is selected from the group consisting of: hydrogen, halogen and alkoxy is preferred.

Also preferred is a compound of formula (I) wherein $R^2$ is hydrogen or fluoro.

Also particularly preferred is a compound of formula (I) wherein $R^3$ is selected from the group consisting of: hydrogen, halogen and alkoxy.

A compound of formula (I) wherein $R^3$ is selected from the group consisting of: hydrogen, fluoro, chloro and methoxy is also preferred.

In particular, preferred is a compound of formula (I) wherein $R^3$ is hydrogen.

Furthermore, preferred is a compound of formula (I) wherein $R^4$ is selected from the group consisting of: hydrogen, halogen and alkoxy.

A compound of formula (I) wherein $R^4$ is hydrogen or fluoro is preferred.

A compound of formula (I) wherein $R^5$ is selected from the group consisting of: alkyl, halophenylalkyl, phenyl, substituted phenyl, thiophenyl and pyridinyl, wherein said substituted phenyl is phenyl substituted with one to three substituents independently selected from the group consisting of alkyl, alkoxy, halogen, cyano, haloalkyl, alkylsulfanyl, aminosulfonyl, alkylsulfonyl, haloalkoxy and alkylcarbonyl is further preferred.

In particular, preferred is a compound of formula (I) wherein $R^5$ is selected from the group consisting of: phenyl, chlorophenyl, methoxyphenyl, methylphenyl, cyanophenyl, trifluoromethylphenyl, chlorofluorophenyl, trimethoxyphenyl, difluorophenyl, dichlorophenyl, bromophenyl, chlorotrifluoromethylphenyl, methylsulfanylphenyl, aminosulfonylphenyl, methylsulfonylphenyl, thiophenyl, fluorophenyl, pyridinyl, bis(trifluoromethyl)phenyl, isopropylphenyl, neopentyl, isopentyl, methylcarbonylphenyl and tert-butyl.

Also preferred is a compound of formula (I) wherein $R^5$ is halophenyl or cyanophenyl.

A compound of formula (I) wherein $R^5$ is chlorophenyl or cyanophenyl is also preferred.

Furthermore, preferred is a compound of formula (I) wherein $R^6$ is selected from the group consisting of: alkyl, hydroxyalkyl, cycloalkyl, phenyl and halophenyl.

Moreover, a compound of formula (I) wherein $R^6$ is alkyl or phenyl is also preferred.

Further, a compound of formula (I) wherein $R^6$ is isopropyl or phenyl is also preferred.

In particular, preferred is a compound of formula (I) wherein $R^6$ is selected from the group consisting of: methyl, phenyl, methoxyphenyl, chlorophenyl, neopentyl, isopropyl, cyclohexyl, hydroxypropyl and tert-butyl.

Particularly preferred is a compound of formula (I) wherein $R^7$ is selected from the group consisting of: substituted phenyl, substituted pyridinyl, substituted thiazolyl and carboxy, wherein said substituted phenyl is phenyl substituted with one to three substituents independently selected from alkyl, hydroxy, alkoxy, carboxy, alkoxycarbonylalkyl, alkylaminocarbonyl, carboxyalkoxy, alkoxycarbonyl, alkoxycarbonylalkoxy and alkylsulfonylaminocarbonyl, and said substituted pyridinyl and said substituted thiazolyl are, respectively, pyridinyl and thiazolyl substituted with alkoxycarbonyl or carboxy.

Also particularly preferred is a compound of formula (I) wherein $R^7$ is selected from the group consisting of: carboxyphenyl, alkoxycarbonylphenyl and carboxypyridinyl.

A compound according of formula (I) wherein $R^7$ is selected from the group consisting of: carboxyphenyl, methoxycarbonylphenyl and carboxypyridinyl is further preferred.

Further preferred is a compound of formula (I) wherein $R^7$ is selected from the group consisting of: ethoxycarbonylphenyl, methoxycarbonylmethylphenyl, phenyl substituted with methyl and methoxycarbonyl, carboxy, methoxycarbonylphenyl, ethoxycarbonylmethoxyphenyl, isopropylaminocarbonylphenyl, methoxycarbonylpyridinyl, ethoxycarbonylthiazolyl, methoxyphenyl, trihydroxyphenyl, hydroxyphenyl, carboxyphenyl, carboxymethoxyphenyl, carboxythiazolyl, carboxypyridinyl and methylsulfonylminocarbonylphenyl.

Also preferred is a compound of formula (I) wherein n is 1.

Particularly preferred is a compound of formula (I) selected from the group consisting of:

3-{2-Oxo-3-[1-phenyl-eth-(E)-ylidene]-2,3-dihydro-indol-1-yl}-benzoic acid ethyl ester;

(3-{2-Oxo-3-[1-phenyl-eth-(E)-ylidene]-2,3-dihydro-indol-1-yl}-phenyl)-acetic acid methyl ester;
2-Methyl-5-{2-oxo-3-[1-phenyl-eth-(E)-ylidene]-2,3-dihydro-indol-1-yl}-benzoic acid methyl ester;
[2-Oxo-3-(1-phenyl-ethylidene)-2,3-dihydro-indol-1-yl]-acetic acid;
3-{3-[1-(4-Chloro-phenyl)-1-phenyl-meth-(E)-ylidene]-2-oxo-2,3-dihydro-indol-1-ylmethyl}-benzoic acid methyl ester;
3-{3-[1-(4-Chloro-phenyl)-1-phenyl-meth-(E)-ylidene]-7-fluoro-2-oxo-2,3-dihydro-indol-1-ylmethyl}-benzoic acid methyl ester;
3-(3-Benzhydrylidene-2-oxo-2,3-dihydro-indol-1-ylmethyl)-benzoic acid methyl ester;
3-{3-[1-(4-Methoxy-phenyl)-1-phenyl-meth-(E)-ylidene]-2-oxo-2,3-dihydro-indol-1-ylmethyl}-benzoic acid methyl ester;
3-{2-Oxo-3-[1-phenyl-1-p-tolyl-meth-(E)-ylidene]-2,3-dihydro-indol-1-ylmethyl}-benzoic acid methyl ester;
3-{3-[1-(4-Chloro-phenyl)-1-(2-methoxy-phenyl)-meth-(Z)-ylidene]-2-oxo-2,3-dihydro-indol-1-ylmethyl}-benzoic acid methyl ester;
3-{3-[1-(4-Cyano-phenyl)-1-phenyl-meth-(E)-ylidene]-2-oxo-2,3-dihydro-indol-1-ylmethyl}-benzoic acid methyl ester;
3-{2-Oxo-3-[1-phenyl-1-(4-trifluoromethyl-phenyl)-meth-(E)-ylidene]-2,3-dihydro-indol-1-ylmethyl}-benzoic acid methyl ester;
3-{3-[1-(3-Chloro-4-fluoro-phenyl)-1-phenyl-meth-(E)-ylidene]-2-oxo-2,3-dihydro-indol-1-ylmethyl}-benzoic acid methyl ester;
3-{2-Oxo-3-[1-phenyl-1-(3,4,5-trimethoxy-phenyl)-meth-(E)-ylidene]-2,3-dihydro-indol-1-ylmethyl}-benzoic acid methyl ester;
3-{3-[1-(3,4-Difluoro-phenyl)-1-phenyl-meth-(E)-ylidene]-2-oxo-2,3-dihydro-indol-1-ylmethyl}-benzoic acid methyl ester;
3-{3-[1-(3-Chloro-phenyl)-1-phenyl-meth-(E)-ylidene]-2-oxo-2,3-dihydro-indol-1-ylmethyl}-benzoic acid methyl ester;
3-{3-[1-(2-Chloro-phenyl)-1-phenyl-meth-(E)-ylidene]-2-oxo-2,3-dihydro-indol-1-ylmethyl}-benzoic acid methyl ester;
3-{3-[1-(4-Chloro-phenyl)-1-phenyl-meth-(E)-ylidene]-5-fluoro-2-oxo-2,3-dihydro-indol-1-ylmethyl}-benzoic acid methyl ester;
3-{3-[1-(3,5-Dichloro-phenyl)-1-phenyl-meth-(E)-ylidene]-2-oxo-2,3-dihydro-indol-1-ylmethyl}-benzoic acid methyl ester;
3-{3-[1-(2,3-Dichloro-phenyl)-1-phenyl-meth-(E)-ylidene]-2-oxo-2,3-dihydro-indol-1-ylmethyl}-benzoic acid methyl ester;
4-{3-[1-(4-Chloro-phenyl)-1-phenyl-meth-(E)-ylidene]-2-oxo-2,3-dihydro-indol-1-ylmethyl}-benzoic acid methyl ester;
3-{3-[1-(4-Chloro-phenyl)-1-phenyl-meth-(E)-ylidene]-5-methoxy-2-oxo-2,3-dihydro-indol-1-ylmethyl}-benzoic acid methyl ester;
3-{3-[1-(2-Bromo-phenyl)-1-phenyl-meth-(E)-ylidene]-2-oxo-2,3-dihydro-indol-1-ylmethyl}-benzoic acid methyl ester;
3-{3-[1-(2-Chloro-5-trifluoromethyl-phenyl)-1-phenyl-meth-(E)-ylidene]-2-oxo-2,3-dihydro-indol-1-ylmethyl}-benzoic acid methyl ester;
3-{3-[1-(4-Chloro-phenyl)-1-phenyl-meth-(E)-ylidene]-4-fluoro-2-oxo-2,3-dihydro-indol-1-ylmethyl}-benzoic acid methyl ester;
3-{3-[1-(4-Chloro-phenyl)-1-phenyl-meth-(E)-ylidene]-6-fluoro-2-oxo-2,3-dihydro-indol-1-ylmethyl}-benzoic acid methyl ester;
3-{3-[1-(3-Bromo-phenyl)-1-phenyl-meth-(E)-ylidene]-2-oxo-2,3-dihydro-indol-1-ylmethyl}-benzoic acid methyl ester;
3-{3-[1-(2-Methylsulfanyl-phenyl)-1-phenyl-meth-(E)-ylidene]-2-oxo-2,3-dihydro-indol-1-ylmethyl}-benzoic acid methyl ester;
3-{7-Chloro-3-[1-(4-chloro-phenyl)-1-phenyl-meth-(E)-ylidene]-5-fluoro-2-oxo-2,3-dihydro-indol-1-ylmethyl}-benzoic acid methyl ester;
3-{2-Oxo-3-[1-phenyl-1-(3-trifluoromethyl-phenyl)-meth-(E)-ylidene]-2,3-dihydro-indol-1-ylmethyl}-benzoic acid methyl ester;
3-{2-Oxo-3-[1-phenyl-1-(4-sulfamoyl-phenyl)-meth-(E)-ylidene]-2,3-dihydro-indol-1-ylmethyl}-benzoic acid methyl ester;
3-{3-[1-(2-Methanesulfonyl-phenyl)-1-phenyl-meth-(E)-ylidene]-2-oxo-2,3-dihydro-indol-1-ylmethyl}-benzoic acid methyl ester;
3-{2-Oxo-3-[1-phenyl-1-thiophen-3-yl-meth-(E)-ylidene]-2,3-dihydro-indol-1-ylmethyl}-benzoic acid methyl ester;
3-{3-[1-(4-Chloro-phenyl)-1-phenyl-meth-(Z)-ylidene]-2-oxo-2,3-dihydro-indol-1-ylmethyl}-benzoic acid methyl ester;
3-{3-[1-(4-Chloro-phenyl)-1-(4-trifluoromethyl-phenyl)-meth-(Z)-ylidene]-2-oxo-2,3-dihydro-indol-1-ylmethyl}-benzoic acid methyl ester;
(4-{3-[1-(4-Chloro-phenyl)-1-phenyl-meth-(E)-ylidene]-2-oxo-2,3-dihydro-indol-1-ylmethyl}-phenoxy)-acetic acid ethyl ester;
3-{3-[1-(4-Chloro-phenyl)-1-phenyl-meth-(E)-ylidene]-2-oxo-2,3-dihydro-indol-1-ylmethyl}-N-isopropyl-benzamide;
6-{3-[1-(4-Chloro-phenyl)-1-phenyl-meth-(E)-ylidene]-2-oxo-2,3-dihydro-indol-1-ylmethyl}-nicotinic acid methyl ester;
2-{3-[1-(4-Chloro-phenyl)-1-phenyl-meth-(E)-ylidene]-2-oxo-2,3-dihydro-indol-1-ylmethyl}-thiazole-4-carboxylic acid ethyl ester;
3-[1-(4-Chloro-phenyl)-1-phenyl-meth-(E)-ylidene]-1-(4-methoxy-benzyl)-1,3-dihydro-indol-2-one;
3-[1-(4-Chloro-phenyl)-1-phenyl-meth-(E)-ylidene]-1-(3,4,5-trihydroxy-benzyl)-1,3-dihydro-indol-2-one;
3-[1-(4-Chloro-phenyl)-1-phenyl-meth-(Z)-ylidene]-1-(3,4,5-trihydroxy-benzyl)-1,3-dihydro-indol-2-one;
3-[1-(4-Chloro-phenyl)-1-phenyl-meth-(E)-ylidene]-1-(4-hydroxy-benzyl)-1,3-dihydro-indol-2-one;
3-{3-[1-(4-chloro-phenyl)-1-phenyl-meth-(E)-ylidene]-2-oxo-2,3-dihydro-indol-1-ylmethyl}-benzoic acid;
3-{3-[1-(4-Fluoro-phenyl)-1-phenyl-meth-(E)-ylidene]-2-oxo-2,3-dihydro-indol-1-ylmethyl}-benzoic acid;
3-{3-[1-(4-Methoxy-phenyl)-1-phenyl-meth-(E)-ylidene]-2-oxo-2,3-dihydro-indol-1-ylmethyl}-benzoic acid;
3-{3-[1-(4-Chloro-phenyl)-1-(2-methoxy-phenyl)-meth-(Z)-ylidene]-2-oxo-2,3-dihydro-indol-1-ylmethyl}-benzoic acid;
3-{2-Oxo-3-[1-phenyl-1-(4-trifluoromethyl-phenyl)-meth-(E)-ylidene]-2,3-dihydro-indol-1-ylmethyl}-benzoic acid;
3-{2-Oxo-3-[1-phenyl-1-(2-trifluoromethoxy-phenyl)-meth-(E)-ylidene]-2,3-dihydro-indol-1-ylmethyl}-benzoic acid;
3-{3-[1-(3-Chloro-4-fluoro-phenyl)-1-phenyl-meth-(E)-ylidene]-2-oxo-2,3-dihydro-indol-1-ylmethyl}-benzoic acid;

3-{2-Oxo-3-[1-phenyl-1-(3,4,5-trimethoxy-phenyl)-meth-(E)-ylidene]-2,3-dihydro-indol-1-ylmethyl}-benzoic acid;
3-{3-[1-(3-Chloro-phenyl)-1-phenyl-meth-(E)-ylidene]-2-oxo-2,3-dihydro-indol-1-ylmethyl}-benzoic acid;
3-{3-[1-(4-Chloro-phenyl)-1-phenyl-meth-(E)-ylidene]-5-fluoro-2-oxo-2,3-dihydro-indol-1-ylmethyl}-benzoic acid;
3-{3-[1-(3,5-Dichloro-phenyl)-1-phenyl-meth-(E)-ylidene]-2-oxo-2,3-dihydro-indol-1-ylmethyl}-benzoic acid;
3-{3-[1-(2,3-Dichloro-phenyl)-1-phenyl-meth-(E)-ylidene]-2-oxo-2,3-dihydro-indol-1-ylmethyl}-benzoic acid;
2-{3-[1-(4-Chloro-phenyl)-1-phenyl-meth-(E)-ylidene]-2-oxo-2,3-dihydro-indol-1-ylmethyl}-benzoic acid;
4-{3-[1-(4-Chloro-phenyl)-1-phenyl-meth-(E)-ylidene]-2-oxo-2,3-dihydro-indol-1-ylmethyl}-benzoic acid;
3-{3-[1-(4-Chloro-phenyl)-1-phenyl-meth-(E)-ylidene]-5-methoxy-2-oxo-2,3-dihydro-indol-1-ylmethyl}-benzoic acid;
6-{3-[1-(4-Chloro-phenyl)-1-phenyl-meth-(E)-ylidene]-2-oxo-2,3-dihydro-indol-1-ylmethyl}-nicotinic acid;
3-{3-[1-(4-Chloro-phenyl)-1-phenyl-meth-(E)-ylidene]-4-fluoro-2-oxo-2,3-dihydro-indol-1-ylmethyl}-benzoic acid;
3-{3-[1-(4-Chloro-phenyl)-1-phenyl-meth-(E)-ylidene]-6-fluoro-2-oxo-2,3-dihydro-indol-1-ylmethyl}-benzoic acid;
3-{3-[1-(2-Methylsulfanyl-phenyl)-1-phenyl-meth-(E)-ylidene]-2-oxo-2,3-dihydro-indol-1-ylmethyl}-benzoic acid;
3-{2-Oxo-3-[1-phenyl-1-pyridin-3-yl-meth-(E)-ylidene]-2,3-dihydro-indol-1-ylmethyl}-benzoic acid;
3-{3-[1-(2-Chloro-5-trifluoromethyl-phenyl)-1-phenyl-meth-(E)-ylidene]-2-oxo-2,3-dihydro-indol-1-ylmethyl}-benzoic acid;
3-{3-[1-(3,5-Bis-trifluoromethyl-phenyl)-1-phenyl-meth-(E)-ylidene]-2-oxo-2,3-dihydro-indol-1-ylmethyl}-benzoic acid;
3-{2-Oxo-3-[1-phenyl-1-(3-trifluoromethyl-phenyl)-meth-(E)-ylidene]-2,3-dihydro-indol-1-ylmethyl}-benzoic acid;
3-{2-Oxo-3-[1-phenyl-1-(4-sulfamoyl-phenyl)-meth-(E)-ylidene]-2,3-dihydro-indol-1-ylmethyl}-benzoic acid;
3-{3-[1-(4-Chloro-phenyl)-1-phenyl-meth-(Z)-ylidene]-2-oxo-2,3-dihydro-indol-1-ylmethyl}-benzoic acid;
3-{3-[1-(4-Chloro-phenyl)-1-(4-trifluoromethyl-phenyl)-meth-(Z)-ylidene]-2-oxo-2,3-dihydro-indol-1-ylmethyl}-benzoic acid;
(4-{3-[1-(4-Chloro-phenyl)-1-phenyl-meth-(E)-ylidene]-2-oxo-2,3-dihydro-indol-1-ylmethyl}-phenoxy)-acetic acid;
3-{3-[1-(4-Isopropyl-phenyl)-1-phenyl-meth-(E)-ylidene]-2-oxo-2,3-dihydro-indol-1-ylmethyl}-benzoic acid;
3-{3-[1-(3,4-Difluoro-phenyl)-1-phenyl-meth-(E)-ylidene]-2-oxo-2,3-dihydro-indol-1-ylmethyl}-benzoic acid;
3-{3-[1-(4-Chloro-phenyl)-1-phenyl-meth-(E)-ylidene]-7-fluoro-2-oxo-2,3-dihydro-indol-1-ylmethyl}-benzoic acid;
3-{5-Chloro-3-[1-(4-chloro-phenyl)-1-phenyl-meth-(E)-ylidene]-2-oxo-2,3-dihydro-indol-1-ylmethyl}-benzoic acid;
3-{3-[1-(2-Chloro-phenyl)-1-phenyl-meth-(E)-ylidene]-2-oxo-2,3-dihydro-indol-1-ylmethyl}-benzoic acid;
2-{3-[1-(4-Chloro-phenyl)-1-phenyl-meth-(E)-ylidene]-2-oxo-2,3-dihydro-indol-1-ylmethyl}-thiazole-4-carboxylic acid;
3-{3-[4-Methyl-1-phenyl-pent-(Z)-ylidene]-2-oxo-2,3-dihydro-indol-1-ylmethyl}-benzoic acid methyl ester;
3-{3-[3,3-Dimethyl-1-phenyl-but-(Z)-ylidene]-2-oxo-2,3-dihydro-indol-1-ylmethyl}-benzoic acid methyl ester;
3-{3-[2-(4-Chloro-phenyl)-1-phenyl-eth-(Z)-ylidene]-2-oxo-2,3-dihydro-indol-1-ylmethyl}-benzoic acid methyl ester;
3-{3-[3,3-Dimethyl-1-phenyl-but-(E)-ylidene]-2-oxo-2,3-dihydro-indol-1-ylmethyl}-benzoic acid methyl ester;
3-{3-[4-Methyl-1-phenyl-pent-(Z)-ylidene]-2-oxo-2,3-dihydro-indol-1-ylmethyl}-benzoic acid;
3-{3-[1-(4-Chloro-benzyl)-2-methyl-prop-(Z)-ylidene]-2-oxo-2,3-dihydro-indol-1-ylmethyl}-benzoic acid;
3-{3-[1-(4-Fluoro-phenyl)-eth-(Z)-ylidene]-2-oxo-2,3-dihydro-indol-1-ylmethyl}benzoic acid;
3-{3-[1-(4-Chloro-phenyl)-2-methyl-prop-(E)-ylidene]-2-oxo-2,3-dihydro-indol-1-ylmethyl}-benzoic acid methyl ester;
3-{3-[2-Methyl-1-phenyl-prop-(E)-ylidene]-2-oxo-2,3-dihydro-indol-1-ylmethyl}-benzoic acid methyl ester;
3-{3-[1-(4-Acetyl-phenyl)-2-methyl-prop-(E)-ylidene]-2-oxo-2,3-dihydro-indol-1-ylmethyl}-benzoic acid methyl ester;
3-{3-[1-(4-Chloro-phenyl)-1-cyclohexyl-meth-(E)-ylidene]-2-oxo-2,3-dihydro-indol-1-ylmethyl}-benzoic acid methyl ester;
3-{3-[2-Methyl-1-(4-trifluoromethyl-phenyl)-prop-(E)-ylidene]-2-oxo-2,3-dihydro-indol-1-ylmethyl}-benzoic acid methyl ester;
3-{3-[1-(4-Chloro-phenyl)-2-hydroxy-2-methyl-prop-(Z)-ylidene]-2-oxo-2,3-dihydro-indol-1-ylmethyl}-benzoic acid methyl ester;
3-{3-[1-(4-Cyano-phenyl)-2-hydroxy-2-methyl-prop-(Z)-ylidene]-2-oxo-2,3-dihydro-indol-1-ylmethyl}-benzoic acid methyl ester;
3-{3-[1-(4-Chloro-phenyl)-2,2-dimethyl-prop-(Z)-ylidene]-2-oxo-2,3-dihydro-indol-1-ylmethyl}-benzoic acid methyl ester;
3-{3-[1-(4-Cyano-phenyl)-2,2-dimethyl-prop-(E)-ylidene]-2-oxo-2,3-dihydro-indol-1-ylmethyl}-benzoic acid methyl ester;
3-{3-[1-(4-Chloro-phenyl)-2,2-dimethyl-prop-(E)-ylidene]-2-oxo-2,3-dihydro-indol-1-ylmethyl}-benzoic acid methyl ester;
3-{3-[1-(4-Chloro-phenyl)-2-methyl-prop-(E)-ylidene]-2-oxo-2,3-dihydro-indol-1-ylmethyl}-benzoic acid;
3-{3-[1-(4-Cyano-phenyl)-2-methyl-prop-(E)-ylidene]-2-oxo-2,3-dihydro-indol-1-ylmethyl}-benzoic acid;
6-{3-[1-(4-Chloro-phenyl)-2-methyl-prop-(E)-ylidene]-2-oxo-2,3-dihydro-indol-1-ylmethyl}-pyridine-2-carboxylic acid;
6-{3-[1-(4-Cyano-phenyl)-2-methyl-prop-(E)-ylidene]-2-oxo-2,3-dihydro-indol-1-ylmethyl}-pyridine-2-carboxylic acid;
3-{3-[1-(4-Chloro-phenyl)-2,2-dimethyl-prop-(Z)-ylidene]-2-oxo-2,3-dihydro-indol-1-ylmethyl}-benzoic acid;
3-{3-[1-(4-Cyano-phenyl)-2,2-dimethyl-prop-(E)-ylidene]-2-oxo-2,3-dihydro-indol-1-ylmethyl}-benzoic acid;
3-{3-[1-(4-Chloro-phenyl)-2,2-dimethyl-prop-(E)-ylidene]-2-oxo-2,3-dihydro-indol-1-ylmethyl}-benzoic acid;
3-{3-[1-(4-Fluoro-phenyl)-2-methyl-prop-(E)-ylidene]-2-oxo-2,3-dihydro-indol-1-ylmethyl}-benzoic acid;
6-{3-[1-(4-Fluoro-phenyl)-2-methyl-prop-(E)-ylidene]-2-oxo-2,3-dihydro-indol-1-ylmethyl}-pyridine-2-carboxylic acid;

3-{3-[2-Methyl-1-pyridin-3-yl-prop-(E)-ylidene]-2-oxo-2,
3-dihydro-indol-1-ylmethyl}-benzoic acid;

3-{3-[1-(4-Chloro-phenyl)-1-cyclohexyl-meth-(E)-ylidene]-2-oxo-2,3-dihydro-indol-1-ylmethyl}-benzoic acid;

3-{3-[2-Methyl-1-(4-trifluoromethyl-phenyl)-prop-(E)-ylidene]-2-oxo-2,3-dihydro-indol-1-ylmethyl}-benzoic acid;

3-{3-[2-Methyl-1-thiophen-3-yl)-prop-(E)-ylidene]-2-oxo-2,3-dihydro-indol-1-ylmethyl}-benzoic acid;

3-{5-Chloro-3-[2-methyl-1-(4-trifluoromethyl-phenyl)-prop-(E)-ylidene]-2-oxo-2,3-dihydro-indol-1-ylmethyl}-benzoic acid;

3-{3-[1-(4-Acetyl-phenyl)-2-methyl-prop-(E)-ylidene]-2-oxo-2,3-dihydro-indol-1-ylmethyl}-benzoic acid;

N-(3-{3-[1-(4-Chloro-phenyl)-2-methyl-prop-(E)-ylidene]-2-oxo-2,3-dihydro-indol-1-ylmethyl}-benzoyl)-methanesulfonamide;

N-(3-{3-[1-(4-Chloro-phenyl)-2,2-dimethyl-prop-(E)-ylidene]-2-oxo-2,3-dihydro-indol-1-ylmethyl}-benzoyl)-methanesulfonamide; and N-(3-{3-[1-(4-Chloro-phenyl)-2,2-dimethyl-prop-(Z)-ylidene]-2-oxo-2,3-dihydro-indol-1-ylmethyl}-benzoyl)-methanesulfonamide;

or a pharmaceutically acceptable salt or ester thereof.

Also particularly preferred is a compound of formula (I) selected from the group consisting of:

3-{3-[1-(4-Chloro-phenyl)-1-phenyl-meth-(E)-ylidene]-2-oxo-2,3-dihydro-indol-1-ylmethyl}-benzoic acid;

3-{3-[1-(4-Chloro-phenyl)-2-methyl-prop-(E)-ylidene]-2-oxo-2,3-dihydro-indol-1-ylmethyl}-benzoic acid;

3-{3-[1-(4-Cyano-phenyl)-2-methyl-prop-(E)-ylidene]-2-oxo-2,3-dihydro-indol-1-ylmethyl}-benzoic acid;

6-{3-[1-(4-Chloro-phenyl)-2-methyl-prop-(E)-ylidene]-2-oxo-2,3-dihydro-indol-1-ylmethyl}-pyridine-2-carboxylic acid; and 6-{3-[1-(4-Cyano-phenyl)-2-methyl-prop-(E)-ylidene]-2-oxo-2,3-dihydro-indol-1-ylmethyl}-pyridine-2-carboxylic acid;

or a pharmaceutically acceptable salt or ester thereof.

The compounds of the present invention can be prepared by any conventional means. Suitable processes for synthesizing these compounds are provided in the examples. Generally, compounds of formula (I) can be prepared according to the schemes illustrated below.

In the following schemes, Ar is phenyl, substituted phenyl, pyridinyl, substituted pyridinyl, thiazolyl or substituted thiazolyl, wherein substituted phenyl is phenyl substituted with one to three substituents independently selected from alkyl, hydroxy, alkoxy, carboxy, alkoxycarbonyl, alkoxycarbonylalkyl, alkylaminocarbonyl, carboxyalkoxy, alkoxycarbonylalkoxy and alkylsulfonylaminocarbonyl, wherein substituted pyridinyl and substituted thiazolyl are pyridinyl and thiazolyl substituted with alkoxycarbonyl or carboxy. $R^8$ is independently selected from the group consisting of alkyl, alkoxy, halogen, cyano, haloalkyl, alkylsulfanyl, aminosulfonyl, alkylsulfonyl, haloalkoxy and alkylcarbonyl as mono-substituent, bi-substituent or tri-substituent. $R^1$ to $R^7$ are as defined above unless otherwise indicated.

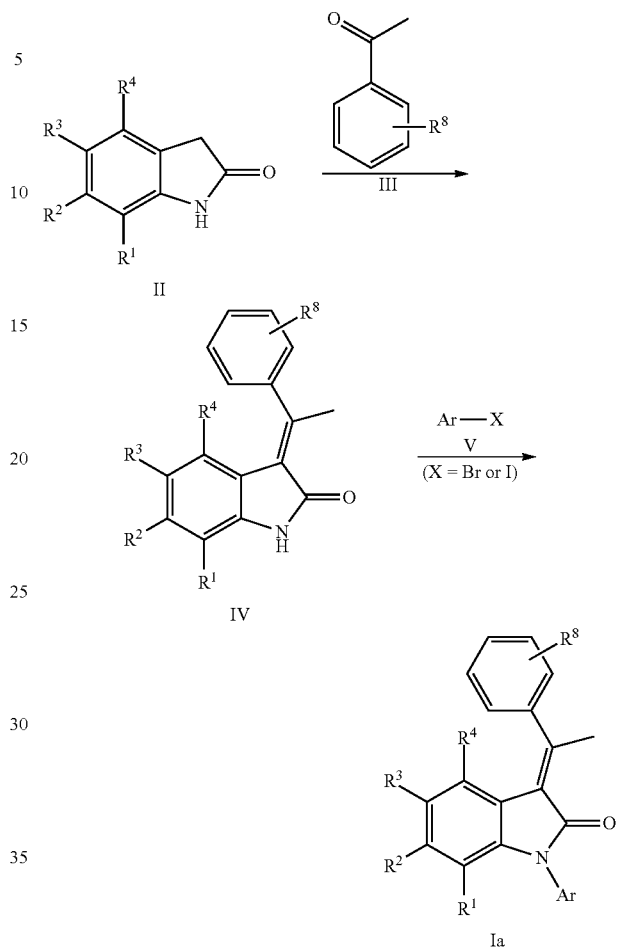

Scheme 1

One method for synthesizing a compound of the invention is set forth in Scheme 1, wherein the oxindole Ia is prepared. In this process, the condensation reaction between the substituted oxindole II and the substituted acetophenone III gives the intermediate IV, which subsequently undergoes coupling reaction in the presence of copper salt catalyst to produce compound Ia.

In the first step outlined in Scheme 1, intermediate IV can be prepared by a condensation reaction between the substituted oxindole II and the substituted acetophenone III. The reaction can be carried out in the presence of an organic base such as piperidine or pyrrolidine, in an organic solvent such as methanol, ethanol, toluene or the mixture thereof, under reflux overnight.

The intermediate IV couples with the aryl halide V to afford the compound of formula Ia. The coupling reaction can be carried out in the presence of a copper catalyst such as copper(I) iodide (CuI), in combination with a ligand such as 2,2'-bipyridine, proline, N,N'-dimethyl glycine or ethylene glycol, and a suitable base such as sodium carbonate, potassium carbonate, cesium carbonate, sodium methoxide, sodium tert-butoxide, potassium tert-butoxide, sodium hydride, triethylamine, or 1,8-diazabicyclo[5.4.0]undec-7-ene (DBU), in a suitable organic solvent such as acetonitrile, dichloromethane, tetrahydrofuran, toluene, benzene, 1,4-dioxane, N,N-dimethylformamide, dimethyl sulfoxide, N-methylpyrrolidinone or a mixture thereof, at a temperature between 100 and 180° C. for 15 to 60 minutes under microwave irradiation. Alternatively, the reaction can be carried out at elevated temperature such as 80° C. for a longer reaction time without microwave irradiation (Ley, S. V. et al., Angew. Chem. Int. Ed. 42 (2003) 5400).

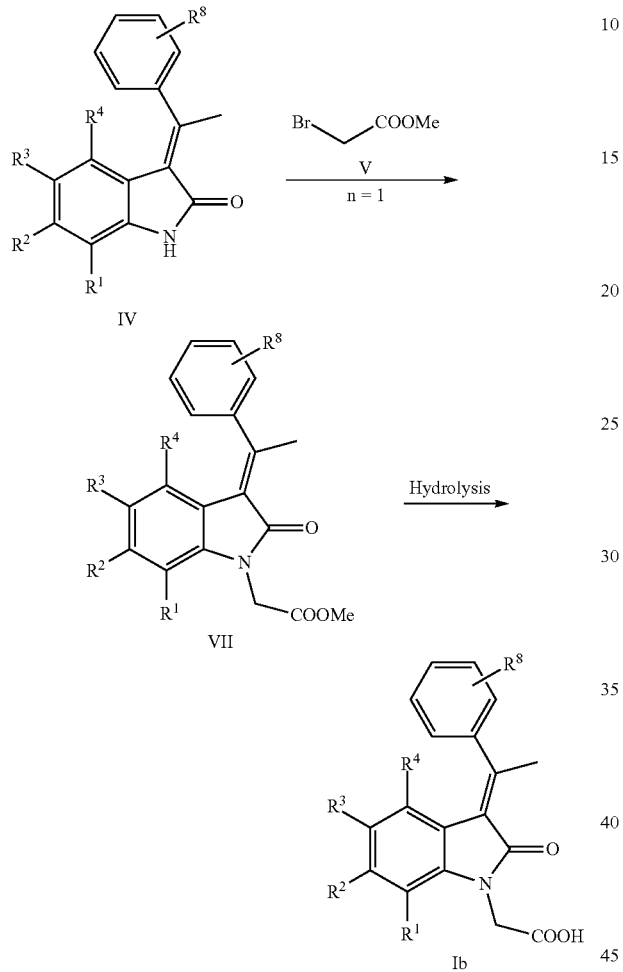

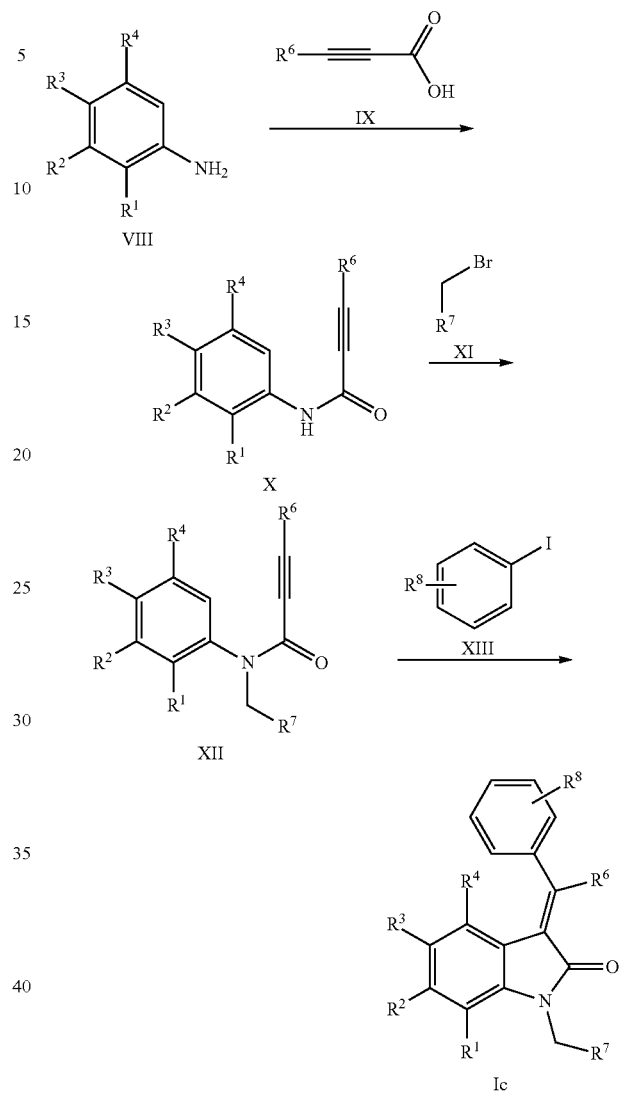

The compound of formula Ib can be prepared according to Scheme 2. In this process, the condensation reaction between the compound IV and the commercially available reagent VI gives the intermediate VII, which subsequently undergoes a hydrolysis reaction to afford the compound of formula Ib.

In the first step outlined in Scheme 2, starting material IV can be obtained through the synthetic method illustrated in Scheme 1. The intermediate VII can be prepared by an alkylation reaction between VI and IV when using base such as sodium hydride, potassium carbonate or cesium carbonate in organic solvent such as tetrahydrofuran, N,N-dimethylformamide or the mixture thereof, at room temperature for several hours.

Finally, hydrolysis of the methyl ester VII affords the compound Ib. Hydrolysis of the methyl ester can be carried out in the presence of an aqueous inorganic base such as lithium hydroxide, sodium hydroxide or potassium hydroxide in a solvent such as methanol, 1,4-dioxane or tetrahydrofuran at room temperature for several hours.

The compound of formula Ic can be prepared according to Scheme 3. This approach is based on a highly efficient palladium-catalyzed synthesis of asymmetrically substituted 3-(diarylmethylenyl)indolinone from readily accessible starting materials. This reaction can be carried out successfully in the presence of catalytic amount of Pd(OAc)$_2$, using N,N-dimethylformamide as solvent and NaOAc as a base. The reaction usually takes place at 110° C. and needs several hours to complete (Artur Pinto et al., Org. Lett. 4927, 2006). The amide X can be prepared by the coupling reaction between aniline VIII and carboxylic acid IX in the presence of coupling reagent such as 1,3-dicyclohexylcarbodiimide.

Intermediate XII can be prepared by alkylation reaction between XI and X. The reaction usually needs sodium hydride, potassium carbonate or cesium carbonate as a base and is carried out at room temperature for several hours in organic solvent such as tetrahydrofuran or N,N-dimethylformamide.

Scheme 4

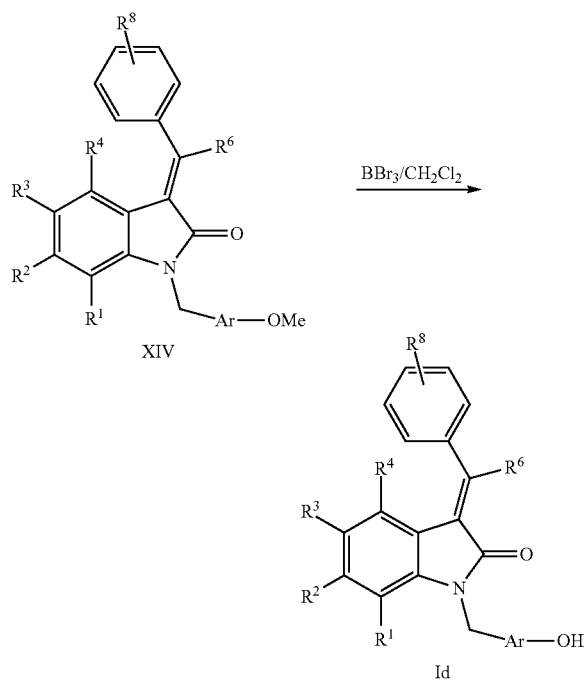

XIV can be prepared by the method described in Scheme 3. Treatment of XIV with boron tribromide in dichloromethane successfully affords Id.

Scheme 5

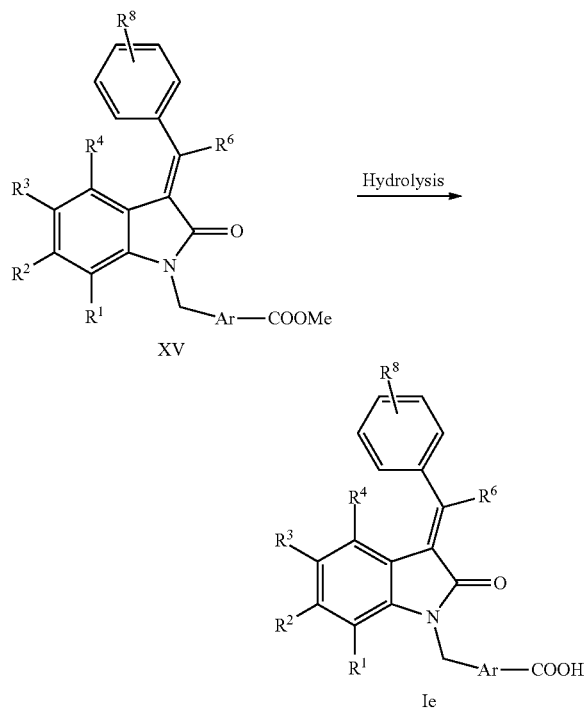

XV can be prepared by the method described in Scheme 3. Hydrolysis of XV in a solvent such as methanol, 1,4-dioxane or tetrahydrofuran at room temperature for several hours in the presence of an aqueous inorganic base such as lithium hydroxide, sodium hydroxide or potassium hydroxide successfully affords acid Ie.

Scheme 6

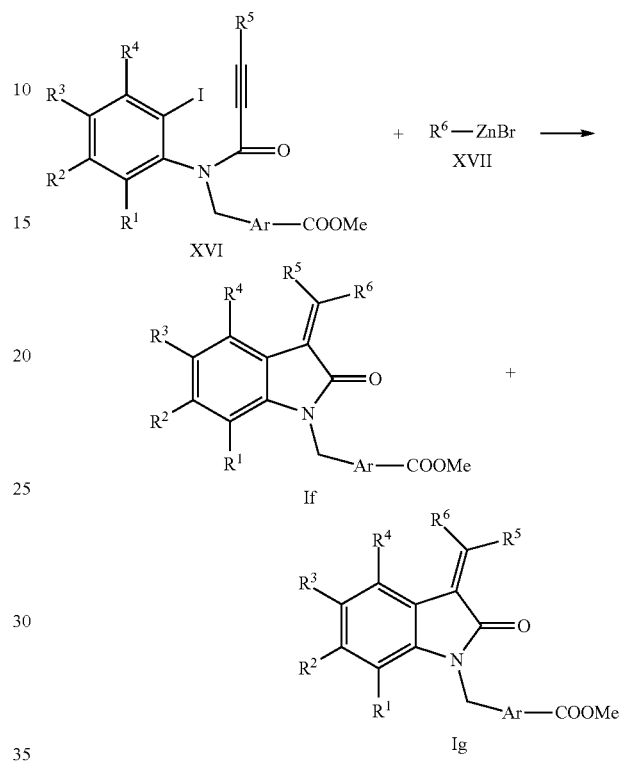

The compounds of formula If and Ig can be prepared according to Scheme 6. This approach is based on Nickel catalyzed carboannulation reaction of zinc reagent XVII with unsaturated compound XVI (Ruixue Deng. et al., Org. Lett. 5207, 2007).

The starting material XVI can be prepared according to the method described in Scheme 3.

Scheme 7

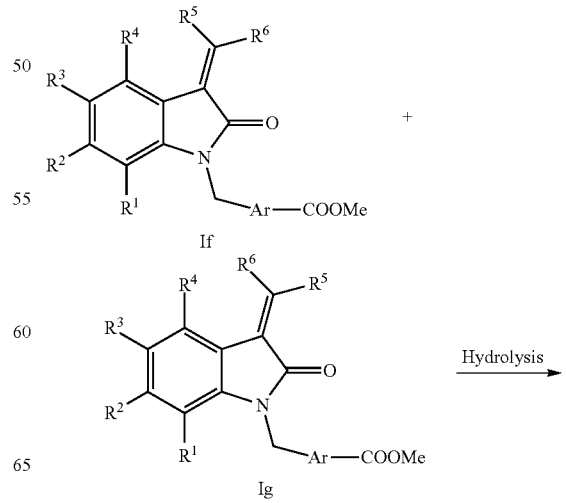

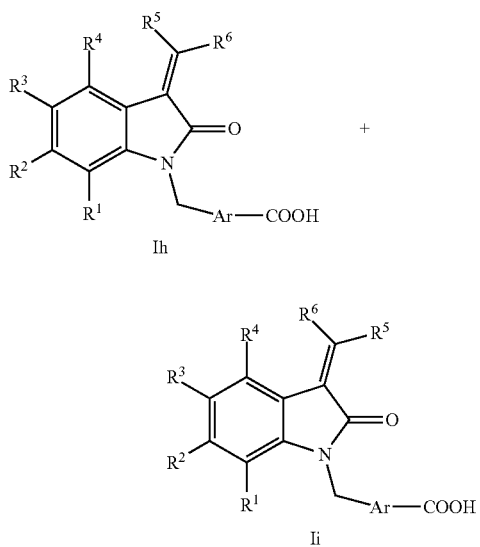

Ih

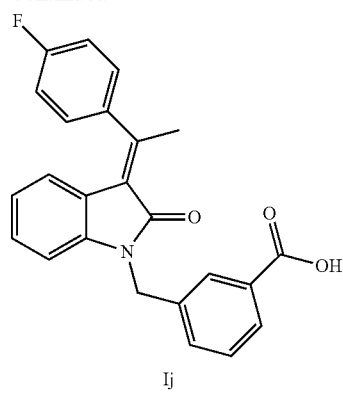

Ij

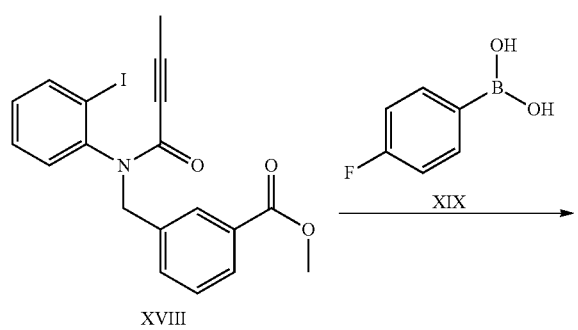

Ii

The compounds of formula Ih and Ii can be prepared according to Scheme 7. Hydrolysis of If and Ig in a solvent such as methanol, 1,4-dioxane or tetrahydrofuran at room temperature for several hours in the presence of an aqueous inorganic base such as lithium hydroxide, sodium hydroxide or potassium hydroxide successfully affords acids Ih and Ii.

The compounds of formula Ij can be prepared according to Scheme 8. The key step is the palladium catalyzed Heck-Carbocyclization/Suzuki-Coupling Reaction between iodide XVIII and boronic acid XIX in the presence of catalytic amount of $Pd(PPh_3)_4$. This reaction proceeds smoothly when using CsF or copper thiophene-2-carboxylic acid as base (Reiko, Y. et al., J. Org. Chem. 70, 6972, 2005; Wing S. Cheung. et al., J. Org. Chem. 70, 3741, 2005).

Hydrolysis of XX in a solvent such as methanol, 1,4-dioxane or tetrahydrofuran at room temperature for several hours in the presence of an aqueous inorganic base such as lithium hydroxide, sodium hydroxide or potassium hydroxide successfully affords acid Ij.

The starting material XVIII can be prepared according to the procedure described in Scheme 3.

Scheme 8

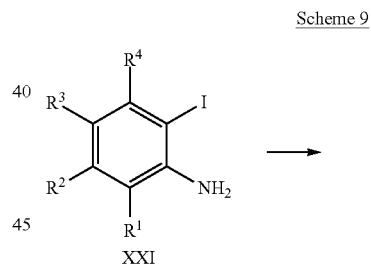

XVIII

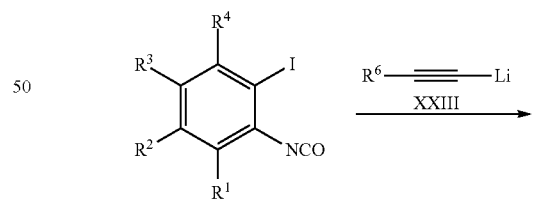

XX

Scheme 9

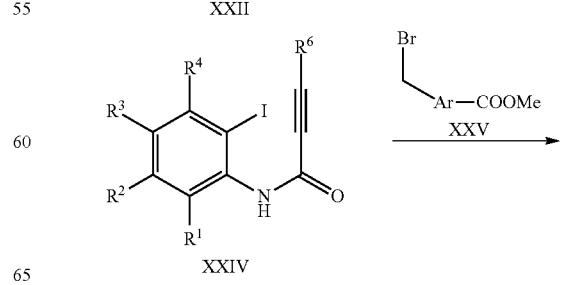

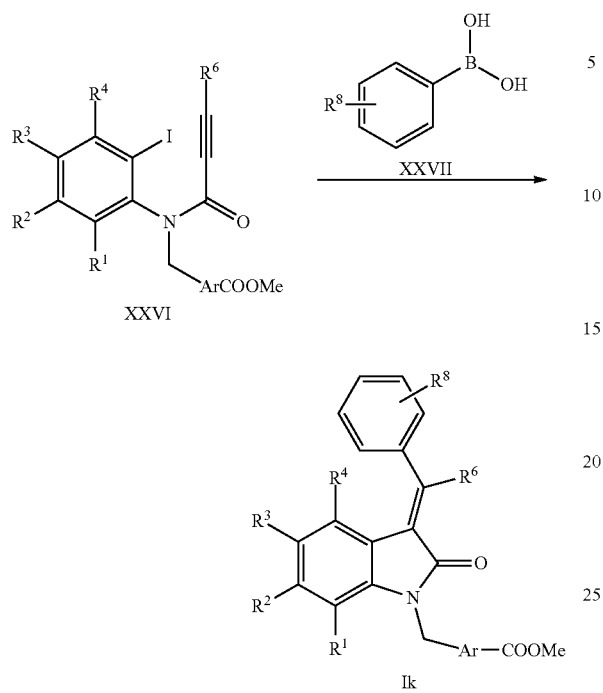

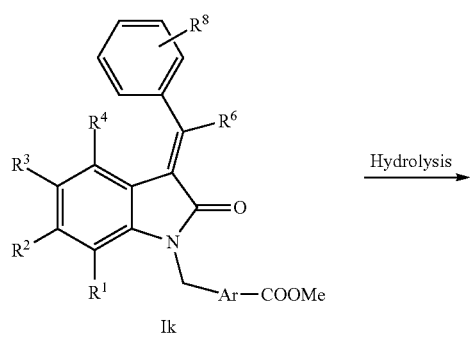

The compounds of formula Ik can be prepared according to Scheme 9. The key step is the palladium catalyzed Heck-Carbocyclization/Suzuki-Coupling Reaction between iodide XXVI and boronic acid XXVII in the presence of catalytic amount of Pd(PPh$_3$)$_4$. This reaction proceeds smoothly when using CsF or copper thiophene-2-carboxylic acid as base (Reiko, Y. et al., J. Org. Chem. 70, 6972, 2005; Wing S. Cheung. et al., J. Org. Chem. 70, 3741, 2005).

The amide XXVI can be prepared by the alkylation between amide XXIV and benzyl bromide XXV as described in Scheme 3. Amide XXIV can be prepared by reacting isocyanate XXII with lithium reagent XXIII generated from n-butyl lithium and acetylene. The isocyanate XXII can be prepared by treating 2-iodo-anilines XXI with triphosgene in organic solvent such as dichloromethane in the presence of saturated aqueous sodium bicarbonate solution.

Scheme 10

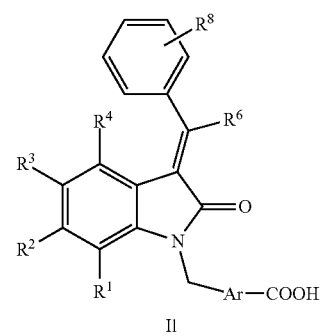

The compounds of formula II can be prepared according to Scheme 10. Hydrolysis of ester Ik in a solvent such as methanol, 1,4-dioxane or tetrahydrofuran at room temperature for several hours in the presence of an aqueous inorganic base such as lithium hydroxide, sodium hydroxide or potassium hydroxide successfully affords acid II.

Scheme 11

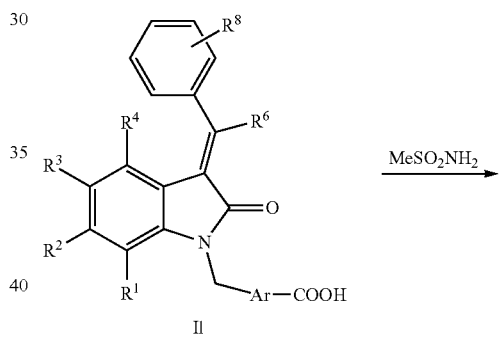

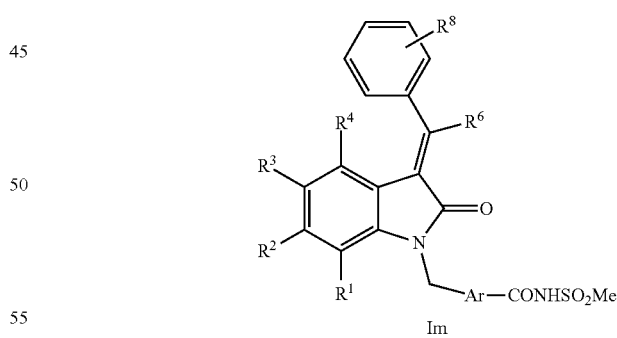

The compounds of formula Im can be prepared according to Scheme 11. Treatment of acid Il with methylsulfonamide in the presence of coupling reagent such as 1-(3-Dimethylaminopropyl)-3-ethylcarbodiimide hydrochloride and organic base such as DMAP for hours successfully affords compound Im.

The invention also relates to a process for the preparation of a compound of formula (I) comprising one of the following steps:

(a) the reaction of a compound according to formula (A)

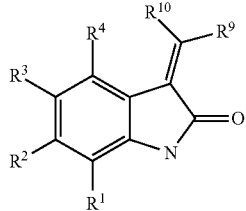
(A)

in the presence R⁷—X and a copper catalyst;
(b) the reaction of a compound according to formula (B)

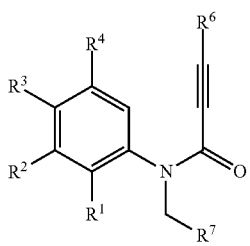
(B)

in the presence of R⁸—I and a palladium catalyst;
(c) the reaction of a compound according to formula (C)

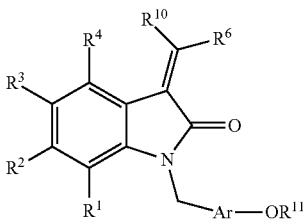
(C)

in the presence of boron tribromide;
(d) the reaction of a compound according to formula (D)

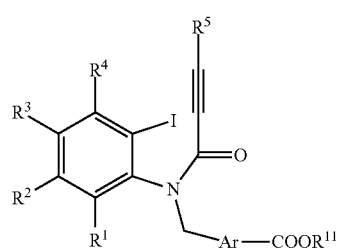
(D)

in the presence of R⁶—ZnBr and a nickel catalyst;

(e) the reaction of a compound according to formula (E)

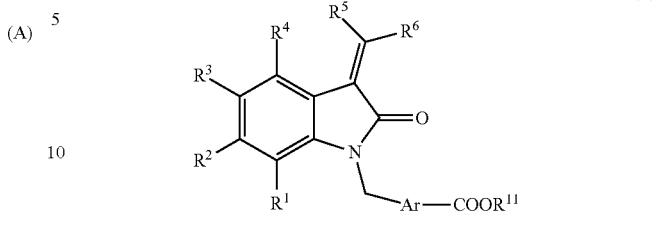
(E)

in the presence of a base;
(f) the reaction of a compound according to formula (F)

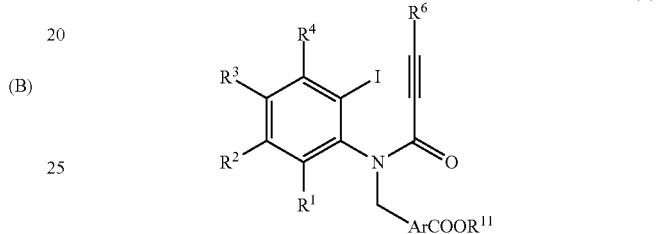
(F)

in the presence of R⁸—B(OH)₂ and a palladium catalyst;
(g) the reaction of a compound according to formula (G)

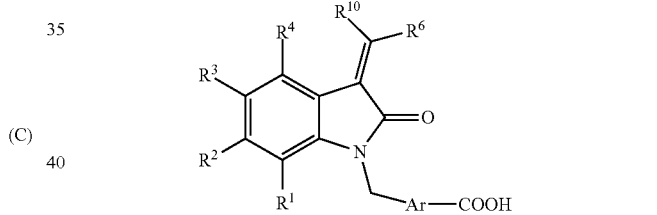
(G)

in the presence of MeSO₂NH₂ and a coupling reagent;
wherein R¹ to R⁷ are as defined above, wherein Ar is selected from the group consisting of: phenyl, substituted phenyl, pyridinyl and thiazolyl, wherein substituted phenyl is phenyl substituted with one or two substituents independently selected from the group consisting of: alkyl, hydroxy, alkoxy, carboxy, alkoxycarbonylalkyl, alkylaminocarbonyl, carboxyalkoxy, alkoxycarbonyl, alkoxycarbonylalkoxy and alkylsulfonylaminocarbonyl, wherein R¹⁰ is phenyl substituted with one to three substituents independently selected from the group consisting of: alkyl, alkoxy, halogen, cyano, haloalkyl, alkylsulfanyl, aminosulfonyl, alkylsulfonyl, haloalkoxy and alkylcarbonyl, wherein R⁹ is alkyl, wherein R¹¹ is alkyl and wherein X is chloro or bromo.

R⁹ is preferably methyl or ethyl. R¹¹ is preferably selected from the group consisting of: C₁-C₄ alkyl, preferably methyl and ethyl, more preferably methyl.

The reaction of step (a) can be carried out in the presence of coupling reagent, such as a copper catalyst, such as copper(I) iodide (CuI), in combination with a ligand such as 2,2'-bipyridine, proline, N,N'-dimethyl glycine or ethylene glycol, and a suitable base such as sodium carbonate, potassium carbonate, cesium carbonate, sodium methoxide, sodium tert-butoxide, potassium tert-butoxide, sodium hydride, triethylamine, or 1,8-diazabicyclo[5.4.0]undec-7-ene (DBU), in a suitable organic solvent such as acetonitrile, dichloromethane, tetrahydrofuran, toluene, benzene, 1,4-dioxane, N,N-dimethylformamide, dimethyl sulfoxide, N-methylpyrrolidinone or a mixture thereof. The reaction temperature can be for example between 100 and 180° C., e.g. for 15 to 60 minutes under microwave irradiation. Alternatively, the reaction can be carried out at an elevated temperature such as 80° C. for a longer reaction time without microwave irradiation.

The reaction of step (b) can be carried out in the presence of catalytic amount of $Pd(OAc)_2$, using N,N-dimethylformamide as solvent and NaOAc as a base. The reaction usually takes place at 110° C. and may need several hours to complete.

Step (c) is preferably carried out in dichloromethane.

Step (e) can be carried out in a solvent such as methanol, 1,4-dioxane or tetrahydrofuran, e.g. at room temperature for several hours. The base is preferably an aqueous inorganic base such as lithium hydroxide, sodium hydroxide or potassium hydroxide.

The reaction of step (f) can be carried out in the presence of catalytic amount of $Pd(PPh_3)_4$. A base is preferably employed. This reaction proceeds smoothly when using CsF or copper thiophene-2-carboxylic acid as base.

The reaction of step (g) can be achieved in the presence of coupling reagent such as 1-(3-Dimethylaminopropyl)-3-ethylcarbodiimide hydrochloride and an organic base such as DMAP.

The invention also relates to a compound of formula (I) for use as therapeutically active substance.

The invention also relates to a pharmaceutical composition comprising a compound of formula (I) and a therapeutically inert carrier.

The use of a compound of formula (I) for the preparation of medicaments useful in the treatment or prophylaxis diseases that are related to AMPK regulation is an object of the invention.

The invention relates in particular to the use of a compound of formula (I) for the preparation of a medicament for the treatment or prophylaxis of obesity, dyslipidemia, hyperglycemia, type 1 diabetes or type 2 diabetes, in particular type 2 diabetes.

Said medicaments, e.g. in the form of pharmaceutical preparations, can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions with an effective amount of a compound as defined above.

The above-mentioned pharmaceutical composition can be obtained by processing the compounds according to this invention with pharmaceutically inert inorganic or organic carriers. Lactose, corn starch or derivatives thereof, talc, stearic acids or its salts and the like can be used, for example, can be used as such carriers for tablets, coated tablets, dragées and hard gelatin capsules. Suitable carriers for soft gelatin capsules are, for example, vegetable oils, waxes, fats, semisolid and liquid polyols and the like. Depending on the nature of the active substance no carriers are, however, usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical composition can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage depends on various factors such as manner of administration, species, age and/or individual state of health. The doses to be administered daily are about 5-400 mg/kg, preferably about 10-100 mg/kg, and can be taken singly or distributed over several administrations.

A compound of formula (I) when manufactured according to the above process is also an object of the invention.

Furthermore, the invention also relates to a method for the treatment or prophylaxis of diseases that are related to AMPK regulation, which method comprises administering an effective amount of a compound of formula (I).

The invention further relates to a method for the treatment or prophylaxis of obesity, dyslipidemia, hyperglycemia, type 1 diabetes or type 2 diabetes, in particular type 2 diabetes, which method comprises administering an effective amount of a compound of formula (I).

Furthermore, the invention also relates to a compound of formula (I) for the preparation of medicaments useful in the treatment of cancers that are related to AMPK regulation and provides a method for the treatment of cancers that are related to AMPK regulation.

The invention is illustrated by the following examples which have no limiting character. Unless explicitly otherwise stated, all reactions, reaction conditions, abbreviations and symbols have the meanings well known to a person of ordinary skill in organic chemistry.

EXAMPLES

Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 uM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 um, OBD™ 30×100 mm) column or SunFire™ Perp $C_{18}$ (5 um, OBD™ 30×100 mm) column.

LC/MS spectra were obtained using a MicroMass Plateform LC (Waters™ alliance 2795-ZQ2000). Standard LC/MS conditions were as follows (running time 6 min):

Acidic condition: A: 0.1% formic acid in $H_2O$; B: 0.1% formic acid in acetonitrile;

Basic condition: A: 0.01% $NH_3.H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(M+H)^+$.

The microwave assisted reactions were carried out in a Biotage Initiator Sixty.

NMR spectra were obtained using Bruker Avance 400 MHz.

All reactions involving air-sensitive reagents were performed under an argon atmosphere. Reagents were used as received from commercial suppliers without further purification unless otherwise noted.

In case a mixture of E and Z isomers is produced during a reaction, these isomers are separated by methods described herein or known to the man skilled in the art such as e.g. chromatography or crystallization.

Example 1

3-[2-Oxo-3-(1-phenyl-ethylidene)-2,3-dihydro-indol-1-yl]-benzoic acid ethyl ester

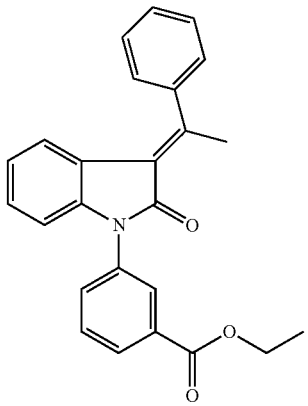 [SMILES: CCOC(=O)c1cccc(N2C(=O)/C(=C(\C)c3ccccc3)c3ccccc32)c1]

3-(1-Phenyl-ethylidene)-1,3-dihydro-indol-2-one

Oxindole (0.1332 g, 1 mmol) and acetophenone (1.4 ml, 1.2 mmol) were mixed in toluene; then pyrrolidine (0.17 ml, 2 mmol) was added. The mixture refluxed for 3 hand monitored by TLC. When the reaction was finished the solvent was removed under reduced pressure. The residue was separated by flash chromatography column (gradient elution, 10-25% ethyl acetate in petroleum ether) to give 3-(1-phenyl-ethylidene)-1,3-dihydro-indol-2-one as yellow powder (200 mg, 85%). $^1$H NMR (400 MHz, DMSO-$d_6$) δ ppm 2.70 (s, 3H) 5.96 (d, J=7.83 Hz, 1H) 6.51-6.57 (m, 1H) 6.77 (d, J=7.58 Hz, 1H) 7.00-7.10 (m, 1H) 7.30-7.37 (m, 2H) 7.44-7.58 (m, 3H) 10.54 (br. s., 1H). MS calcd. for $C_{16}H_{13}NO$ 235, obsd. (ESI$^+$) [(M+H)$^+$] 236.

3-[2-Oxo-3-(1-phenyl-ethylidene)-2,3-dihydro-indol-1-yl]-benzoic acid ethyl ester A Schlenk tube was charged with CuI (9.6 mg, 0.050 mmol, 5.0 mol %), 3-(1-phenyl-ethylidene)-1,3-dihydro-indol-2-one (352.7 mg, 1.5 mmol), and $K_2CO_3$ (276 mg, 2.0 mmol), evacuated, and backfilled with argon. N,N'-dimethylethylenediamine (11 uL, 0.10 mmol, 10 mol %), ethyl 3-iodobenzoate (278.8 mg, 1.01 mmol), and acetonitrile (1.5 ml) were added under argon. The Schlenk tube was sealed with a Teflon valve and the reaction mixture was stirred at 80° C. for 23 h. The reaction was monitored by HPLC. When the reaction was finished, the solvent was removed under reduced pressure. The residue was separated by flash chromatography column (gradient elution, 5-10% ethyl acetate in petroleum ether) to give 3-[2-oxo-3-(1-phenyl-ethylidene)-2,3-dihydro-indol-1-yl]-benzoic acid ethyl ester as yellow powder (344 mg, 90%). $^1$H NMR (400 MHz, CDCl$_3$) δppm 1.42 (t, J=7.20 Hz, 3H) 2.87 (s, 3H) 4.42 (q, J=7.07 Hz, 2H) 6.25 (d, J=7.58 Hz, 1H) 6.68-6.78 (m, 2H) 7.09 (t, J=7.71 Hz, 1H) 7.34-7.40 (m, 2H) 7.47-7.58 (m, 3H) 7.62-7.72 (m, 2H) 8.11-8.19 (m, 2H). MS calcd. for $C_{25}H_{21}NO_3$ 383, obsd. (ESI$^+$) [(M+H)$^+$] 383.9.

Example 2

(3-{2-Oxo-3-[1-phenyl-eth-(E)-ylidene]-2,3-dihydro-indol-1-yl}-phenyl)-acetic acid methyl ester

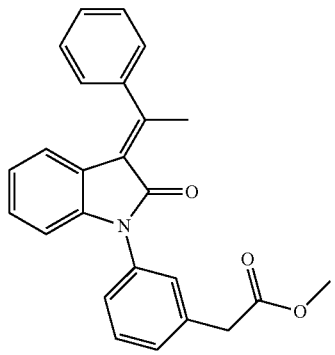 [SMILES: COC(=O)Cc1cccc(N2C(=O)/C(=C(\C)c3ccccc3)c3ccccc32)c1]

The title compound was prepared in analogy to Example 1 starting from (3-bromo-phenyl)-acetic acid methyl ester (commercially available) and 3-[1-phenyl-eth-(E)-ylidene]-1,3-dihydro-indol-2-one. $^1$H NMR (400 MHz, DMSO-$d_6$) δppm 2.77 (s, 3H) 3.65 (s, 3H) 3.81 (s, 2H) 6.08 (d, J=7.33 Hz, 1H) 6.66-6.72 (m, 2H) 7.11 (t, J=7.33 Hz, 1H) 7.35-7.44 (m, 5H) 7.51-7.61 (m, 4H).

Example 3

2-Methyl-5-{2-oxo-3-[1-phenyl-eth-(E)-ylidene]-2,3-dihydro-indol-1-yl}-benzoic acid methyl ester

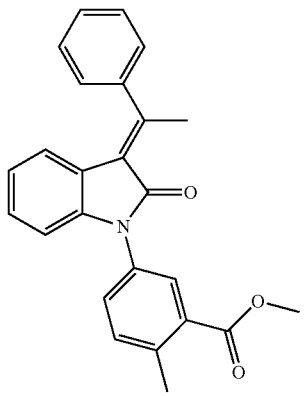 [SMILES: COC(=O)c1cc(N2C(=O)/C(=C(\C)c3ccccc3)c3ccccc32)ccc1C]

The title compound was prepared in analogy to Example 1 starting from 5-bromo-2-methyl-benzoic acid methyl ester (commercially available) and 3-[1-phenyl-eth-(E)-ylidene]-1,3-dihydro-indol-2-one. $^1$H NMR (400 MHz, chloroform-d) δppm 2.71 (s, 3H) 2.86 (s, 3H) 3.91 (s, 3H) 6.24 (d, J=7.83

Hz, 1H) 6.67-6.75 (m, 2H) 7.08 (t, J=7.83 Hz, 1H) 7.34-7.37 (m, 2H) 7.43-7.47 (m, 1H) 7.49-7.56 (m, 4H) 8.05 (d, J=2.27 Hz, 1H).

Example 4

[2-Oxo-3-(1-phenyl-ethylidene)-2,3-dihydro-indol-1-yl]-acetic acid

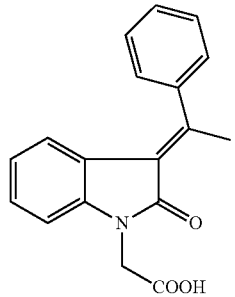 [SMILES: C/C(=C1\C(=O)N(CC(=O)O)c2ccccc21)c1ccccc1]

3-(1-Phenyl-ethylidene)-1,3-dihydro-indol-2-one

The synthetic method of 3-(1-phenyl-ethylidene)-1,3-dihydro-indol-2-one is described in Example 1.

[2-Oxo-3-(1-phenyl-ethylidene)-2,3-dihydro-indol-1-yl]-acetic acid methyl ester 3-(1-Phenyl-ethylidene)-1,3-dihydro-indol-2-one (294 mg, 1 mmol) was dissolved in anhydrous DMF, then methyl bromoacetate (184 mg, 1.2 mmol) was added. Finally, $Cs_2CO_3$ (488 mg, 1.5 mmol) was added in one portion. The mixture was stirred at room temperature overnight. The reaction was monitored by HPLC. When the reaction was finished, the solvent was removed under reduced pressure. The residue was separated by flash chromatography column (gradient elution, 5-10% ethyl acetate in petroleum ether) to give [2-oxo-3-(1-phenyl-ethylidene)-2,3-dihydro-indol-1-yl]-acetic acid methyl ester as yellow powder (230 mg, 75%). MS calcd. for $C_{19}H_{17}NO_3$ 307, obsd. (ESI$^+$) [(M+1)$^+$] 308.1.

[2-Oxo-3-(1-phenyl-ethylidene)-2,3-dihydro-indol-1-yl]-acetic acid

[2-Oxo-3-(1-phenyl-ethylidene)-2,3-dihydro-indol-1-yl]-acetic acid methyl ester (50 mg, 0.16 mmol) was dissolved in menthol 1 ml; then 0.1 ml water was added. Finally, lithium hydroxide (10 mg) was added. The mixture was stirred overnight. The reaction was monitored by HPLC. When the reaction was finished, the solvent was removed under reduced pressure. The residue was dissolved in 2 ml DMF for prepared HPLC to give [2-oxo-3-(1-phenyl-ethylidene)-2,3-dihydro-indol-1-yl]-acetic acid as white powder (11 mg). $^1$H NMR (400 MHz, CDCl$_3$) δ ppm 2.82 (s, 3H) 4.61 (s, 2H) 6.20 (d, J=7.58 Hz, 1H) 6.66-6.73 (m, 2H) 7.14 (t, J=7.58 Hz, 1H) 7.31 (s, 2H) 7.46-7.54 (m, 3H). MS calcd. for $C_{18}H_{15}NO_3$ 293, obsd. (ESI$^+$) [(M+H)$^+$]294.1.

Example 5

3-((3-((4-Chlorophenyl)(phenyl)meth-(E)-ylene)-2-oxoindolin-1-yl)methyl)benzoic acid methyl ester

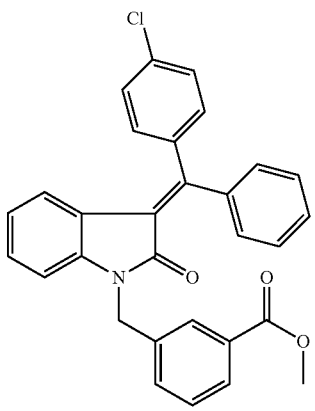 [SMILES: COC(=O)c1cccc(CN2C(=O)/C(=C(\c3ccccc3)c3ccc(Cl)cc3)c3ccccc32)c1]

3-Phenyl-propynoic acid phenylamide

Phenylamine (1.86 g, 20 mmol) and phenylpropiolic acid (3.22 g, 22 mmol) were dissolved in dichloromethane (50 ml) and 1,3-dicyclohexylcarbodiimide (4.8 g, 23.2 mmol) was added in one portion at 0° C. The mixture was stirred room temperature for 14 h. The mixture was poured into water and extracted with dichloromethane (3×15 ml). The organic layers were combined, dried over anhydrous sodium sulfate and concentrated in vacuo. Purification by flash column chromatography on silica gel, eluting with hexanes-EtOAc (6:1 and then 4:1) afforded 3-phenyl-propynoic acid phenylamide 2.7 g (62%).

3-{[Phenyl-(3-phenyl-propynoyl)-amino]-methyl}-benzoic acid methyl ester

3-Phenyl-propynoic acid phenylamide (951.4 mg, 4.3 mmol), 3-bromomethyl-benzoic acid methyl ester (1.2 g, 5.16 mmol) and $Cs_2CO_3$ (2.1 g, 6.45 mmol) were dissolved in DMF (20 ml). The mixture was stirred at room temperature for 16 h. The mixture was poured into water and extracted with ethyl acetate, dried over anhydrous sodium sulfate and concentrated under reduced pressure. Purification was by flash column chromatography on silica gel, eluting with hexanes-EtOAc (6:1 and then 4:1) afforded 3-{[phenyl-(3-phenyl-propynoyl)-amino]-methyl}-benzoic acid methyl ester 1.03 g (65%).

3-{3-[1-(4-Chloro-phenyl)-1-phenyl-meth-(E)-ylidene]-2-oxo-2,3-dihydro-indol-1-ylmethyl}-benzoic acid methyl ester To a solution of 3-{[phenyl-(3-phenyl-propynoyl)-amino]-methyl}-benzoic acid methyl ester (369.4 mg, 1 mmol) in THF (5 ml) were added palladium(II) acetate (11.2 mg, 0.05 mmol), triphenylphosphine (26.2 mg, 0.1 mmol), 1-chloro-4-iodobenzene (262.3 mg, 1.1 mmol) and cesium fluoride (456 mg, 3 mmol) at room temperature. The solution was stirred for 3 h at 110° C. under an argon atmosphere. After being quenched with water, the mixture was extracted with ethyl acetate, dried over magnesium sulfate and concentrated under reduced pressure. The residue was purified by flash column chromatography on silica gel eluting with (hexane/ ethyl acetate=5/1) to give 3-{3-[1-(4-chloro-phenyl)-1-phenyl-meth-(E)-ylidene]-2-oxo-2,3-dihydro-indol-1-ylmethyl}-benzoic acid methyl ester, yield 297 mg (62%); $^1$H NMR (CDCl$_3$, 300 MHz) δ ppm 8.00 (s, 1H), 7.92 (d, 1H), 7.50 (d, 1H), 7.26-7.43 (m, 10H), 7.08 (dt, 1H), 6.71 (dt, 1H), 6.59 (d, 1H), 6.52 (d, 1H), 4.95 (s, 2H), 3.90 (s, 3H).

Example 6

3-{3-[1-(4-Chloro-phenyl)-1-phenyl-meth-(E)-ylidene]-7-fluoro-2-oxo-2,3-dihydro-indol-1-ylmethyl}-benzoic acid methyl ester

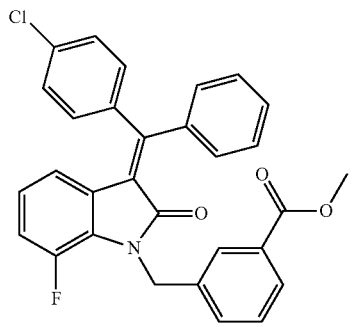 [SMILES: COC(=O)c1cccc(CN2C(=O)/C(=C(\c3ccccc3)c3ccc(Cl)cc3)c3cccc(F)c32)c1]

The title compound was prepared in analogy to Example 5 starting from 1-chloro-4-iodo-benzene (commercially available) and 3-{[(2-fluoro-phenyl)-(3-phenyl-propynoyl)-amino]-methyl}-benzoic acid methyl ester. $^1$H NMR (300 Hz, CDCl$_3$): δppm 3.88 (s, 3H), 5.11 (s, 2H), 6.22 (d, 1H), 6.61-6.67 (m, 1H), 6.82-6.89 (dd, 1H), 7.26-7.43 (m, 10H), 7.52 (d, 1H), 7.92 (d, 1H), 8.01 (s, 1H).

Example 7

3-(3-Benzhydrylidene-2-oxo-2,3-dihydro-indol-1-ylmethyl)-benzoic acid methyl ester

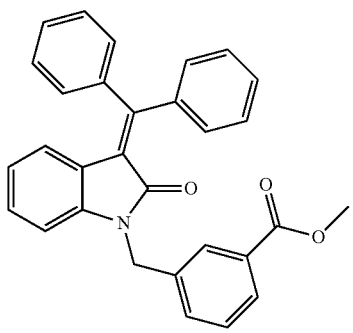 [SMILES: COC(=O)c1cccc(CN2C(=O)C(=C(c3ccccc3)c3ccccc3)c3ccccc32)c1]

The title compound was prepared in analogy to Example 5 starting from iodo-benzene (commercially available) and 3-{[phenyl-(3-phenyl propynoyl)-amino]-methyl}-benzoic acid methyl ester. $^1$H NMR (CDCl$_3$, 300 MHz) δppm 8.01 (s, 1H), 8.00 (d, 1H), 7.93 (d, 1H), 7.33-7.52 (m, 12H), 7.05 (dt, 1H), 6.66 (m, 2H), 6.43 (d, 2H), 4.96 (s, 2H), 3.91 (s, 3H).

Example 8

3-{3-[1-(4-Methoxy-phenyl)-1-phenyl-meth-(E)-ylidene]-2-oxo-2,3-dihydro-indol-1-ylmethyl}-benzoic acid methyl ester

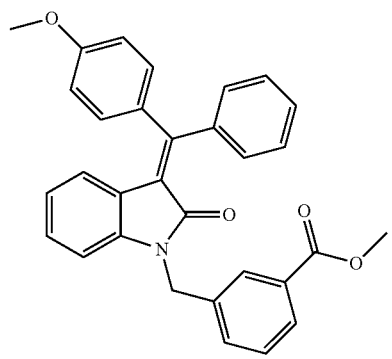

The title compound was prepared in analogy to Example 5 starting from 1-iodo 4-methoxy-benzene (commercially available) and 3-{[phenyl-(3-phenyl propynoyl)-amino]-methyl}-benzoic acid methyl ester. $^1$H NMR (CDCl$_3$, 300 MHz) δppm 8.01 (s, 1H), 7.94 (d, 1H), 7.49 (d, 1H), 7.26-7.38 (m, 8H), 7.06 (m, 1H), 6.94 (m, 2H), 6.63-6.70 (m, 3H), 4.97 (s, 2H), 3.91 (s, 3H), 3.88 (s, 3H).

Example 9

3-{2-Oxo-3-[1-phenyl-1-p-tolyl-meth-(E)-ylidene]-2,3-dihydro-indol-1-ylmethyl}-benzoic acid methyl ester

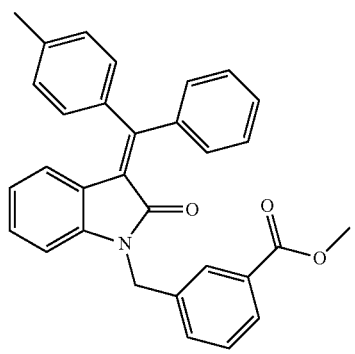 [SMILES: COC(=O)c1cccc(CN2C(=O)/C(=C(\c3ccccc3)c3ccc(C)cc3)c3ccccc32)c1]

The title compound was prepared in analogy to Example 5 starting from 1-methyl-4-iodo-benzene (commercially available) and 3-{[phenyl-(3-phenyl propynoyl)-amino]-methyl}-benzoic acid methyl ester. $^1$H NMR (CDCl$_3$, 300 MHz) δppm 8.01 (s, 1H), 7.92 (d, 1H), 7.24-7.52 (m, 11H), 7.05 (t, 1H), 7.56-7.71 (m, 3H), 4.96 (s, 2H), 3.91 (s, 3H), 2.44 (s, 3H).

Example 10

3-{3-[1-(4-Chloro-phenyl)-1-(2-methoxy-phenyl)-meth-(Z)-ylidene]-2-oxo-2,3-dihydro-indol-1-ylmethyl}-benzoic acid methyl ester

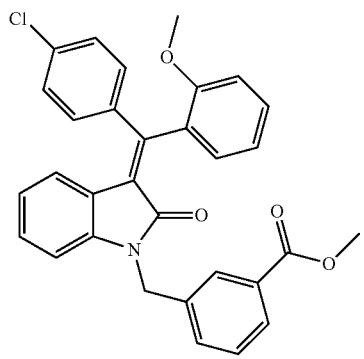 [SMILES: COC(=O)c1cccc(CN2C(=O)/C(=C(/c3ccc(Cl)cc3)c3ccccc3OC)c3ccccc32)c1]

The title compound was prepared in analogy to Example 5 starting from 1-chloro-4-iodo-benzene (commercially available) and 3-({[3-(2-methoxy-phenyl)-propynoyl]-phenyl-amino}-methyl)-benzoic acid methyl ester. $^1$H NMR (CDCl$_3$, 300 MHz) δppm 7.99 (s, 1H), 7.92 (d, 1H), 7.26-7.49 (m, 7H), 6.93-7.15 (m, 4H), 6.72 (t, 1H), 6.61-6.64 (m, 2H), 4.93 (dd, 2H), 3.90 (s, 3H), 3.63 (s, 3H).

Example 11

3-{3-[1-(4-Cyano-phenyl)-1-phenyl-meth-(E)-ylidene]-2-oxo-2,3-dihydro-indol-1-ylmethyl}-benzoic acid methyl ester

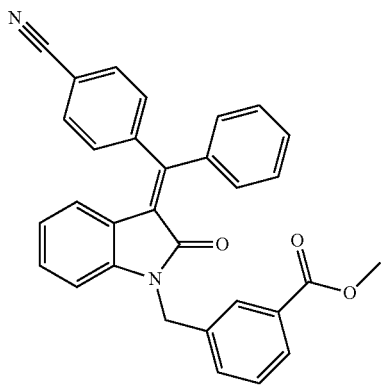 [SMILES: COC(=O)c1cccc(CN2C(=O)/C(=C(\c3ccccc3)c3ccc(C#N)cc3)c3ccccc32)c1]

The title compound was prepared in analogy to Example 5 starting from 4-iodo-benzonitrile (commercially available) and 3-{[phenyl-(3-phenyl propynoyl)-amino]-methyl}-benzoic acid methyl ester. $^1$H NMR (CDCl$_3$, 300 MHz) δppm 8.00 (s, 1H), 7.93 (d, 1H), 7.74-7.76 (m, 2H), 7.35-7.51 (m, 9H), 7.10 (t, 1H), 6.56-6.72 (m, 2H), 6.35 (d, 1H), 4.95 (s, 2H), 3.91 (s, 3H)

Example 12

3-{2-Oxo-3-[1-phenyl-1-(4-trifluoromethyl-phenyl)-meth-(E)-ylidene]-2,3-dihydro-indol-1-ylmethyl}-benzoic acid methyl ester

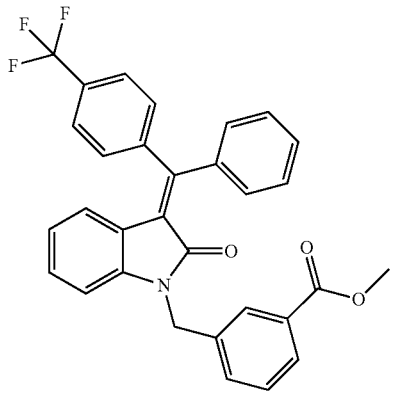 [SMILES: COC(=O)c1cccc(CN2C(=O)/C(=C(\c3ccccc3)c3ccc(C(F)(F)F)cc3)c3ccccc32)c1]

The title compound was prepared in analogy to Example 5 starting from 1-iodo-4-trifluoromethyl-benzene (commercially available) and 3-{[phenyl-(3-phenyl propynoyl)-amino]-methyl}-benzoic acid methyl ester. $^1$H NMR (300 Hz, CDCl$_3$) δppm 3.91 (s, 3H), 4.96 (s, 2H), 6.37 (d, 1H), 6.67 (dd, 2H), 7.08 (t, 1H), 7.35-7.40 (m, 7H), 7.49 (d, 2H), 7.71 (d, 2H), 7.95 (d, 1H), 8.01 (s, 1H).

Example 13

3-{3-[1-(3-Chloro-4-fluoro-phenyl)-1-phenyl-meth-(E)-ylidene]-2-oxo-2,3-dihydro-indol-1-ylmethyl}-benzoic acid methyl ester

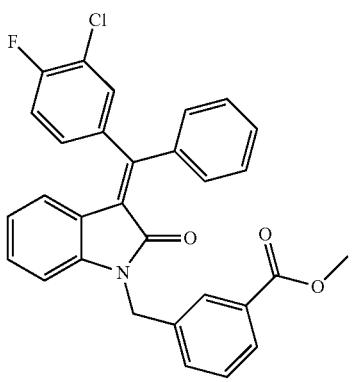 [SMILES: COC(=O)c1cccc(CN2C(=O)/C(=C(\c3ccccc3)c3ccc(F)c(Cl)c3)c3ccccc32)c1]

The title compound was prepared in analogy to Example 5 starting from 2-chloro-1-fluoro-4-iodo-benzene (commercially available) and 3-{[phenyl-(3-phenyl propynoyl)-amino]-methyl}-benzoic acid methyl ester. $^1$H NMR (CDCl$_3$, 300 MHz) δppm 8.00 (s, 1H), 7.93 (d, 1H), 7.50 (d, 1H), 7.22-7.42 (m, 9H), 7.09 (dt, 1H), 6.73 (dt, 1H), 6.66 (d, 1H), 6.51 (d, 1H), 4.95 (s, 2H), 3.91 (s, 3H).

Example 14

3-{2-Oxo-3-[1-phenyl-1-(3,4,5-trimethoxy-phenyl)-meth-(E)-ylidene]-2,3-dihydro-indol-1-ylmethyl}-benzoic acid methyl ester

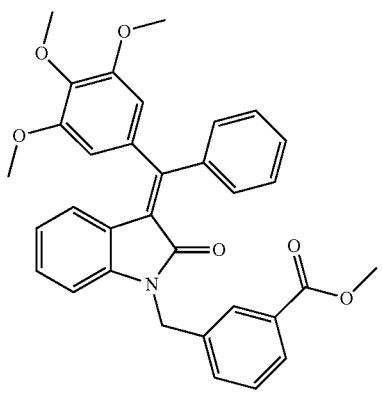

The title compound was prepared in analogy to Example 5 starting from 5-Iodo-1,2,3-trimethoxy-benzene (commercially available) and 3-{[phenyl-(3-phenyl propynoyl)-amino]-methyl}-benzoic acid methyl ester. $^1$H NMR (300 Hz, CDCl$_3$): δppm 3.76 (s, 6H), 3.91 (s, 3H), 3.94 (s, 3H), 4.96 (s, 2H), 6.55 (s, 2H), 6.61-6.71 (m, 4H), 7.06 (t, 1H), 7.38-7.40 (m, 5H), 7.53 (d, 1H), 7.91 (d, 1H), 8.02 (s, 1H).

Example 15

3-{3-[1-(3,4-Difluoro-phenyl)-1-phenyl-meth-(E)-ylidene]-2-oxo-2,3-dihydro-indol-1-ylmethyl}-benzoic acid methyl ester

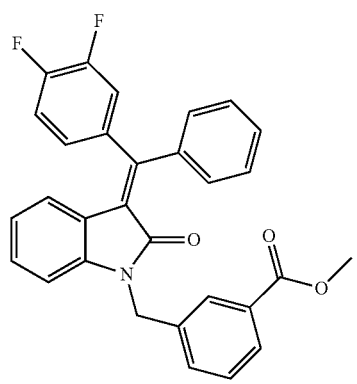 [SMILES: COC(=O)c1cccc(CN2C(=O)/C(=C(\c3ccccc3)c3ccc(F)c(F)c3)c3ccccc32)c1]

The title compound was prepared in analogy to Example 5 starting from 1,2-difluoro-4-iodo-benzene (commercially available) and 3-{[phenyl-(3-phenyl propynoyl)-amino]-methyl}-benzoic acid methyl ester. $^1$H NMR (300 Hz, CDCl$_3$): δppm 3.90 (s, 3H), 4.96 (s, 2H), 6.58 (d, 1H), 6.70 (m, 2H), 7.07-7.32 (m, 4H), 7.34-7.43 (m, 6H), 7.50 (d, 1H), 7.94 (d, 1H), 8.02 (s, 1H).

Example 16

3-{3-[1-(3-Chloro-phenyl)-1-phenyl-meth-(E)-ylidene]-2-oxo-2,3-dihydro-indol-1-ylmethyl}-benzoic acid methyl ester

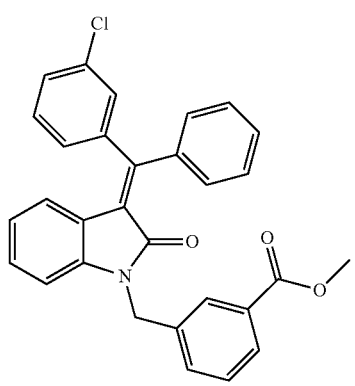 [SMILES: COC(=O)c1cccc(CN2C(=O)/C(=C(\c3ccccc3)c3cccc(Cl)c3)c3ccccc32)c1]

The title compound was prepared in analogy to Example 5 starting from 1-chloro-3-iodo-benzene (commercially available) and 3-{[phenyl-(3-phenyl propynoyl)-amino]-methyl}-benzoic acid methyl ester. $^1$H NMR (CDCl$_3$, 300 MHz) δppm 8.01 (s, 1H), 7.93 (d, 1H), 7.50 (d, 1H), 7.26-7.46 (m, 10H), 7.08 (t, 1H), 6.70 (t, 1H), 6.65 (d, 1H), 6.44 (d, 1H), 4.96 (s, 2H), 3.90 (s, 3H).

Example 17

3-{3-[1-(2-Chloro-phenyl)-1-phenyl-meth-(E)-ylidene]-2-oxo-2,3-dihydro-indol-1-ylmethyl}-benzoic acid methyl ester

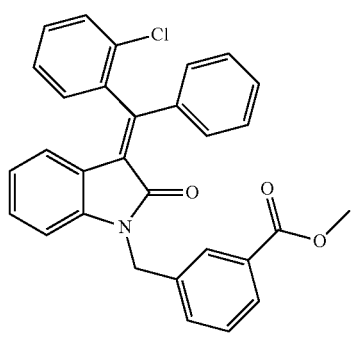 [SMILES: COC(=O)c1cccc(CN2C(=O)/C(=C(\c3ccccc3)c3ccccc3Cl)c3ccccc32)c1]

The title compound was prepared in analogy to Example 5 starting from 1-chloro-2-iodo-benzene (commercially available) and 3-{[phenyl-(3-phenyl propynoyl)-amino]-methyl}-benzoic acid methyl ester. $^1$H NMR (CDCl$_3$, 300 MHz) δppm 8.01 (s, 1H), 7.92 (d, 1H), 7.50-7.52 (m, 4H), 7.37-7.42 (m, 7H), 7.07 (t, 1H), 6.62-6.69 (m, 1H), 6.05 (d, 1H), 4.96 (dd, 2H), 3.91 (s, 3H).

Example 18

3-{3-[1-(4-Chloro-phenyl)-1-phenyl-meth-(E)-ylidene]-5-fluoro-2-oxo-2,3-dihydro-indol-1-ylmethyl}-benzoic acid methyl ester

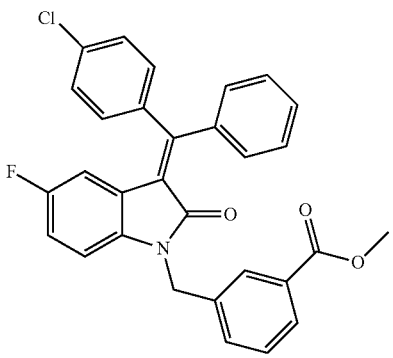 [SMILES: COC(=O)c1cccc(CN2C(=O)/C(=C(\c3ccccc3)c3ccc(Cl)cc3)c3cc(F)ccc32)c1]

The title compound was prepared in analogy to Example 5 starting from 1-chloro-4-iodo-benzene (commercially available) and 3-{[(4-fluoro-phenyl)-(3-phenyl-propynoyl)-amino]-methyl}-benzoic acid methyl ester. $^1$H NMR (300 Hz, CDCl$_3$): δppm 3.91 (s, 3H), 4.94 (s, 2H), 6.25 (dd, 1H), 6.54 (dd, 2H), 6.75-6.80 (m, 1H), 7.10 (d, 2H), 7.33-7.54 (m, 8H), 7.94 (d, 1H), 7.98 (s, 1H).

Example 19

3-{3-[1-(3,5-Dichloro-phenyl)-1-phenyl-meth-(E)-ylidene]-2-oxo-2,3-dihydro-indol-1-ylmethyl}-benzoic acid methyl ester

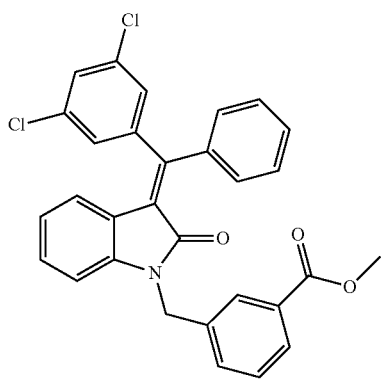 [SMILES: COC(=O)c1cccc(CN2C(=O)/C(=C(\c3ccccc3)c3cc(Cl)cc(Cl)c3)c3ccccc32)c1]

The title compound was prepared in analogy to Example 5 starting from 1,3-dichloro-5-iodobenzene (commercially available) and 3-{[phenyl-(3-phenyl propynoyl)-amino]-methyl}-benzoic acid methyl ester. $^1$H NMR (300 Hz, CDCl$_3$):

δppm 3.92 (s, 3H), 4.95 (s, 2H), 6.47 (d, 1H), 6.65-6.78 (m, 2H), 7.13 (t, 2H), 7.33-7.43 (m, 8H), 7.52 (d, 1H), 7.93 (d, 1H), 8.01 (s, 1H).

Example 20

3-{3-[1-(2,3-Dichloro-phenyl)-1-phenyl-meth-(E)-ylidene]-2-oxo-2,3-dihydro-indol-1-ylmethyl}-benzoic acid methyl ester

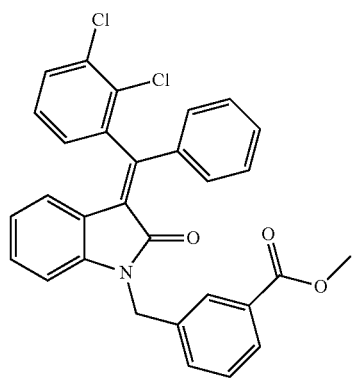 [SMILES: COC(=O)c1cccc(CN2C(=O)/C(=C(\c3ccccc3)c3cccc(Cl)c3Cl)c3ccccc32)c1]

The title compound was prepared in analogy to Example 5 starting from 1,2-dichloro-3-iodobenzene (commercially available) and 3-{[phenyl-(3-phenyl propynoyl)-amino]-methyl}-benzoic acid methyl ester. $^1$H NMR (CDCl$_3$, 300 MHz) δppm 8.00 (s, 1H), 7.92 (d, 1H), 7.33-7.54 (m, 9H), 7.23 (dd, 1H), 7.10 (t, 1H), 6.74 (t, 1H), 6.66 (d, 1H), 6.55 (d, 1H), 4.95 (s, 2H), 3.90 (s, 3H).

Example 21

4-{3-[1-(4-Chloro-phenyl)-1-phenyl-meth-(E)-ylidene]-2-oxo-2,3-dihydro-indol-1-ylmethyl}-benzoic acid methyl ester

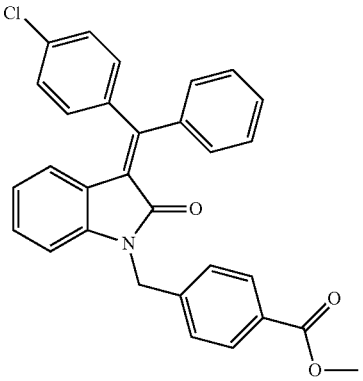 [SMILES: COC(=O)c1ccc(CN2C(=O)/C(=C(\c3ccccc3)c3ccc(Cl)cc3)c3ccccc32)cc1]

The title compound was prepared in analogy to Example 5 starting from 1-chloro-4-iodobenzene (commercially available) and 4-{[phenyl-(3-phenyl propynoyl)-amino]-methyl}-benzoic acid methyl ester. $^1$H NMR (CDCl$_3$, 300 MHz) δppm 7.97 (d, 1H), 7.25-7.43 (m, 12H), 7.07 (dt, 1H), 6.71 (dt, 1H), 6.61 (d, 1H), 6.54 (d, 1H), 4.97 (s, 2H), 3.89 (s, 3H).

Example 22

3-{3-[1-(4-Chloro-phenyl)-1-phenyl-meth-(E)-ylidene]-5-methoxy-2-oxo-2,3-dihydro-indol-1-ylmethyl}-benzoic acid methyl ester

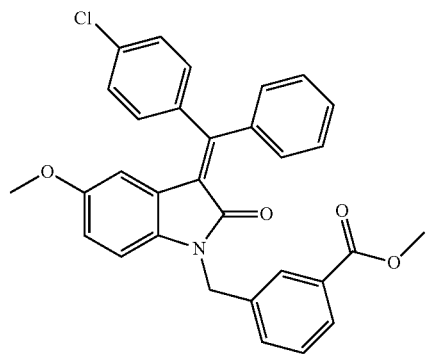

The title compound was prepared in analogy to Example 5 starting from 1-chloro-4-iodobenzene (commercially available) and 3-{[(4-methoxy-phenyl)-(3-phenyl-propynoyl)-amino]-methyl}-benzoic acid methyl ester. $^1$H NMR (300 Hz, CDCl$_3$): δppm 3.49 (s, 3H), 3.91 (s, 3H), 4.92 (s, 2H), 6.10 (dd, 1H), 6.51 (d, 1H), 6.62 (dd, 1H), 7.25-7.50 (m, 1H), 7.93 (d, 1H), 7.99 (s, 1H).

Example 23

3-{3-[1-(2-Bromo-phenyl)-1-phenyl-meth-(E)-ylidene]-2-oxo-2,3-dihydro-indol-1-ylmethyl}-benzoic acid methyl ester

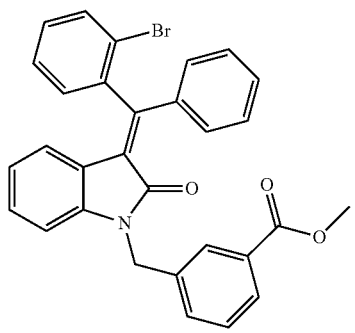 [SMILES: COC(=O)c1cccc(CN2C(=O)/C(=C(\c3ccccc3)c3ccccc3Br)c3ccccc32)c1]

The title compound was prepared in analogy to Example 5 starting from 1-bromo-2-iodobenzene (commercially available) and 3-{[phenyl-(3-phenyl propynoyl)-amino]-methyl}-benzoic acid methyl ester. $^1$H NMR (CDCl$_3$, 300 MHz) δppm 8.01 (s, 1H), 7.93 (d, 1H), 7.71 (d, 1H), 7.30-7.53 (m, 11H), 7.04-7.09 (m, 2H), 6.62-7.04 (m, 3H), 6.42 (d, 1H), 6.02 (d, 1H), 4.88-5.05 (m, 2H), 3.91 (s, 3H).

Example 24

3-{3-[1-(2-Chloro-5-trifluoromethyl-phenyl)-1-phenyl-meth-(E)-ylidene]-2-oxo-2,3-dihydro-indol-1-ylmethyl}-benzoic acid methyl ester

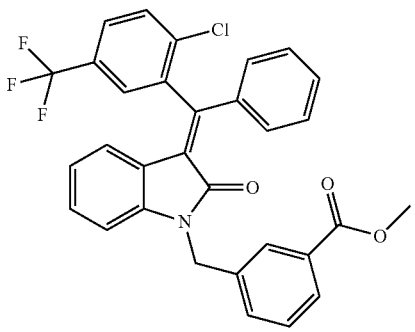 [SMILES: COC(=O)c1cccc(CN2C(=O)/C(=C(\c3ccccc3)c3cc(C(F)(F)F)ccc3Cl)c3ccccc32)c1]

The title compound was prepared in analogy to Example 5 starting from 1-chloro-2-iodo-4-trifluoromethyl-benzene (commercially available) and 3-{[phenyl-(3-phenyl propynoyl)-amino]-methyl}-benzoic acid methyl ester. $^1$H NMR (CDCl$_3$, 300 MHz) δppm 8.01 (s, 1H), 7.93 (d, 1H), 7.63-7.67 (m, 2H), 7.33-7.52 (m, 7H), 7.10 (t, 1H), 6.64-6.71 (m, 2H), 5.98 (d, 1H), 4.87-5.04 (m, 2H), 3.91 (s, 3H).

Example 25

3-{3-[1-(4-Chloro-phenyl)-1-phenyl-meth-(E)-ylidene]-4-fluoro-2-oxo-2,3-dihydro-indol-1-ylmethyl}-benzoic acid methyl ester

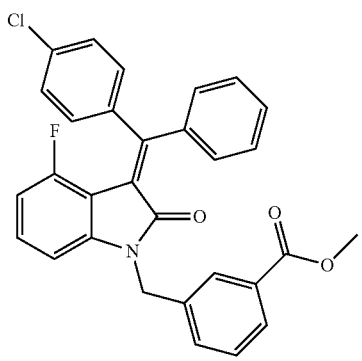 [SMILES: COC(=O)c1cccc(CN2C(=O)/C(=C(\c3ccccc3)c3ccc(Cl)cc3)c3c(F)cccc32)c1]

The title compound was prepared in analogy to Example 5 starting from 1-chloro-4-iodo-benzene (commercially available) and 3-{[(3-fluoro-phenyl)-(3-phenyl-propynoyl)-amino]-methyl}-benzoic acid methyl ester. $^1$H NMR (300

Hz, CDCl$_3$): δppm 4.97 (s, 2H), 6.39-6.51 (m, 2H), 7.25-7.45 (m, 11H), 7.53 (d, 1H), 7.99 (d, 1H), 8.00 (s, 1H).

Example 26

3-{3-[1-(4-Chloro-phenyl)-1-phenyl-meth-(E)-ylidene]-6-fluoro-2-oxo-2,3-dihydro-indol-1-ylmethyl}-benzoic acid methyl ester

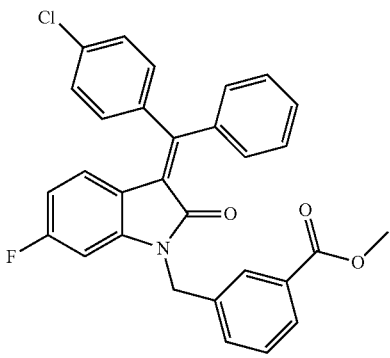 [SMILES: COC(=O)c1cccc(CN2C(=O)/C(=C(\c3ccccc3)c3ccc(Cl)cc3)c3ccc(F)cc32)c1]

The title compound was prepared in analogy to Example 5 starting from 1-chloro-4-iodo-benzene (commercially available) and 3-{[(3-fluoro-phenyl)-(3-phenyl-propynoyl)-amino]-methyl}-benzoic acid methyl ester. $^1$H NMR (300 Hz, CDCl$_3$): δppm 3.90 (s, 3H), 4.96 (s, 2H), 6.48 (d, 1H), 7.10 (d, 1H), 7.19 (d, 1H), 7.31-7.50 (m, 11H), 7.94 (d, 1H), 7.98 (s, 1H).

Example 27

3-{3-[1-(3-Bromo-phenyl)-1-phenyl-meth-(E)-ylidene]-2-oxo-2,3-dihydro-indol-1-ylmethyl}-benzoic acid methyl ester

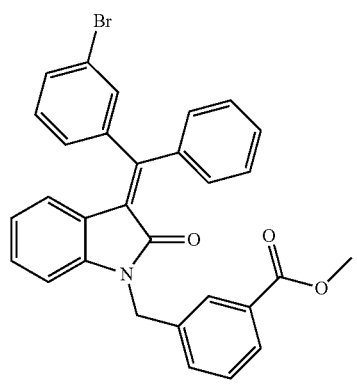 [SMILES: COC(=O)c1cccc(CN2C(=O)/C(=C(\c3ccccc3)c3cccc(Br)c3)c3ccccc32)c1]

The title compound was prepared in analogy to Example 5 starting from 1-bromo-3-iodobenzene (commercially available) and 3-{[phenyl-(3-phenyl propynoyl)-amino]-methyl}-benzoic acid methyl ester. $^1$H NMR (CDCl$_3$, 300 MHz) δppm 8.01 (s, 1H), 7.93 (d, 1H), 7.31-7.61 (m, 11H), 7.08 (t, 1H), 6.64-6.73 (m, 2H), 6.44 (d, 1H), 4.95 (s, 2H), 3.91 (s, 3H).

Example 28

3-{3-[1-(2-Methylsulfanyl-phenyl)-1-phenyl-meth-(E)-ylidene]-2-oxo-2,3-dihydro-indol-1-ylmethyl}-benzoic acid methyl ester

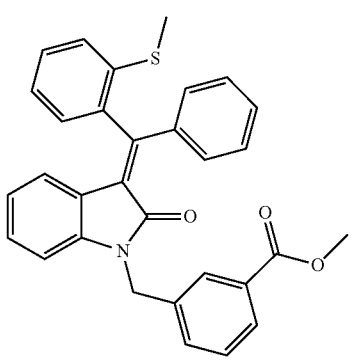 [SMILES: COC(=O)c1cccc(CN2C(=O)/C(=C(\c3ccccc3)c3ccccc3SC)c3ccccc32)c1]

The title compound was prepared in analogy to Example 5 starting from 1-iodo-2-methylsulfanyl-benzene (commercially available) and 3-{[phenyl-(3-phenyl propynoyl)-amino]-methyl}-benzoic acid methyl ester. $^1$H NMR (300 Hz, CDCl$_3$): δppm 2.31 (s, 3H), 3.90 (s, 3H), 5.00 (dd, 2H), 6.03 (d, 1H), 6.60-6.64 (m, 2H), 7.04 (t, 1H), 7.26-7.30 (m, 2H), 7.33-7.56 (m, 9H), 7.95 (d, 1H), 8.01 (s, 1H).

Example 29

3-{7-Chloro-3-[1-(4-chloro-phenyl)-1-phenyl-meth-(E)-ylidene]-5-fluoro-2-oxo-2,3-dihydro-indol-1-ylmethyl}-benzoic acid methyl ester

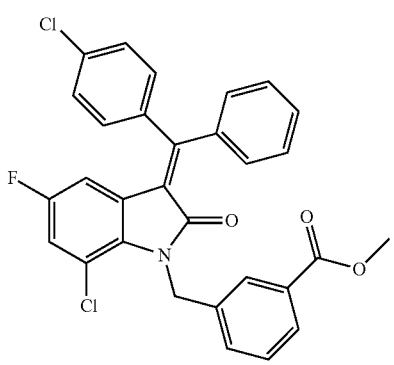 [SMILES: COC(=O)c1cccc(CN2C(=O)/C(=C(\c3ccccc3)c3ccc(Cl)cc3)c3cc(F)cc(Cl)c32)c1]

The title compound was prepared in analogy to Example 5 starting from 1-chloro-4-iodo-benzene (commercially available) and 3-{[(2-chloro-4-fluoro-phenyl)-(3-phenyl-propynoyl)-amino]-methyl}-benzoic acid methyl ester. $^1$H NMR (300 Hz, CDCl$_3$): δppm 3.90 (s, 3H), 5.38 (s, 2H), 6.01 (dd, 1H), 6.80 (dd, 1H), 7.27-7.40 (m, 9H), 7.45-7.50 (m, 3H), 7.92 (m, 2H).

Example 30

3-{2-Oxo-3-[1-phenyl-1-(3-trifluoromethyl-phenyl)-meth-(E)-ylidene]-2,3-dihydro-indol-1-ylmethyl}-benzoic acid methyl ester

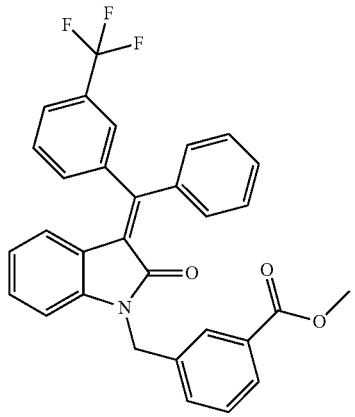 [SMILES: COC(=O)c1cccc(CN2C(=O)/C(=C(\c3ccccc3)c3cccc(C(F)(F)F)c3)c3ccccc32)c1]

The title compound was prepared in analogy to Example 5 starting from 1-iodo-3-trifluoromethyl-benzene (commercially available) and 3-{[phenyl-(3-phenyl propynoyl)-amino]-methyl}-benzoic acid methyl ester. $^1$H NMR (CDCl$_3$, 300 MHz) δppm 8.01 (s, 1H), 7.95 (d, 1H), 7.72 (d, 1H), 7.50-7.63 (m, 3H), 7.36-7.42 (m, 4H), 7.08 (t, 1H), 6.64-6.68 (m, 2H), 6.42 (d, 1H), 4.96 (s, 2H), 3.91 (s, 3H).

Example 31

3-{2-Oxo-3-[1-phenyl-1-(4-sulfamoyl-phenyl)-meth-(E)-ylidene]-2,3-dihydro-indol-1-ylmethyl}-benzoic acid methyl ester

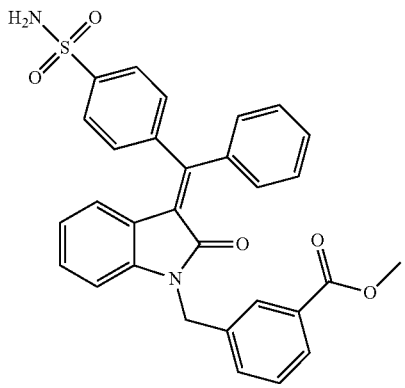 [SMILES: COC(=O)c1cccc(CN2C(=O)/C(=C(\c3ccccc3)c3ccc(S(N)(=O)=O)cc3)c3ccccc32)c1]

The title compound was prepared in analogy to Example 5 starting from 4-iodo-benzenesulfonamide (commercially available) and 3-{[phenyl-(3-phenyl propynoyl)-amino]-methyl}-benzoic acid methyl ester. $^1$H NMR (300 Hz, CDCl$_3$): δppm 3.90 (s, 3H), 4.95 (s, 2H), 5.02 (s, 2H), 6.41 (d, 1H), 6.65-6.71 (m, 2H), 7.09 (t, 1H), 7.26-7.33 (m, 2H), 7.35-7.42 (m, 6H), 7.58-7.60 (m, 3H), 7.99 (d, 1H), 8.07 (s, 1H).

Example 32

3-{3-[1-(2-Methanesulfonyl-phenyl)-1-phenyl-meth-(E)-ylidene]-2-oxo-2,3-dihydro-indol-1-ylmethyl}-benzoic acid methyl ester

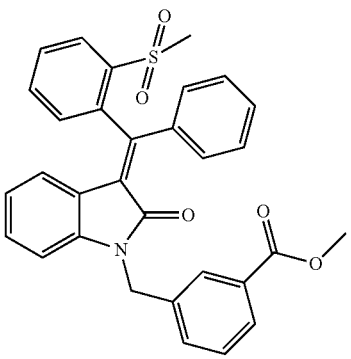 [SMILES: COC(=O)c1cccc(CN2C(=O)/C(=C(\c3ccccc3)c3ccccc3S(C)(=O)=O)c3ccccc32)c1]

The title compound was prepared in analogy to Example 5 starting from 1-iodo-2-methanesulfonyl-benzene (commercially available) and 3-{[phenyl-(3-phenyl propynoyl)-amino]-methyl}-benzoic acid methyl ester. $^1$H NMR (300 Hz, CDCl$_3$): δppm 1.89 (s, 1.5H), 2.50 (s, 1.5H), 3.90 (s, 3H), 4.98 (dd, 2H), 5.98 (dd, 1H), 6.65-6.68 (m, 2H), 7.07 (m, 1H), 7.35-7.58 (m, 8H), 7.61 (t, 1H), 7.78 (t, 1H), 7.99 (d, 1H), 8.02 (d, 1H), 8.20 (d, 1H).

Example 33

3-{2-Oxo-3-[1-phenyl-1-thiophen-3-yl-meth-(E)-ylidene]-2,3-dihydro-indol-1-ylmethyl}-benzoic acid methyl ester

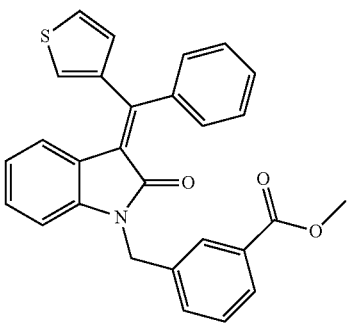 [SMILES: COC(=O)c1cccc(CN2C(=O)/C(=C(\c3ccccc3)c3ccsc3)c3ccccc32)c1]

The title compound was prepared in analogy to Example 5 starting from 3-iodo-thiophene (commercially available) and 3-{[phenyl-(3-phenyl propynoyl)-amino]-methyl}-benzoic acid methyl ester. $^1$H NMR (300 Hz, CDCl$_3$): δppm 3.91 (s, 3H), 4.96 (s, 2H), 6.65 (d, 1H), 6.76-6.82 (m, 2H), 7.06-7.11 (m, 2H), 7.33-7.43 (m, 8H), 7.50 (d, 1H), 7.92 (d, 1H), 8.01 (s, 1H).

Example 34

3-{3-[1-(4-Chloro-phenyl)-1-phenyl-meth-(Z)-ylidene]-2-oxo-2,3-dihydro-indol-1-ylmethyl}-benzoic acid methyl ester

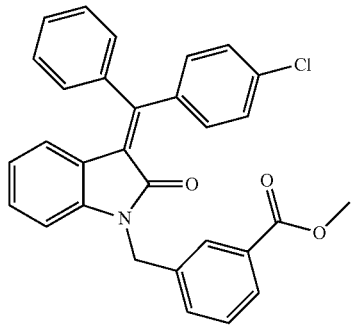 [SMILES: COC(=O)c1cccc(CN2C(=O)/C(=C(/c3ccccc3)c3ccc(Cl)cc3)c3ccccc32)c1]

The title compound was prepared in analogy to Example 5 starting from 1-chloro-4-iodo-benzene (commercially available) and 3-{[phenyl-(3-phenyl-propynoyl)-amino]-methyl}-benzoic acid methyl ester. $^1$H NMR (300 Hz, CDCl$_3$): δppm 3.91 (s, 3H), 4.96 (s, 2H), 6.42 (d, 1H), 6.63-6.66 (m, 2H), 7.06 (t, 1H), 7.33-7.52 (m, 11H), 7.92 (d, 1H), 8.01 (s, 1H).

Example 35

3-{3-[1-(4-Chloro-phenyl)-1-(4-trifluoromethyl-phenyl)-meth-(Z)-ylidene]-2-oxo-2,3-dihydro-indol-1-ylmethyl}-benzoic acid methyl ester

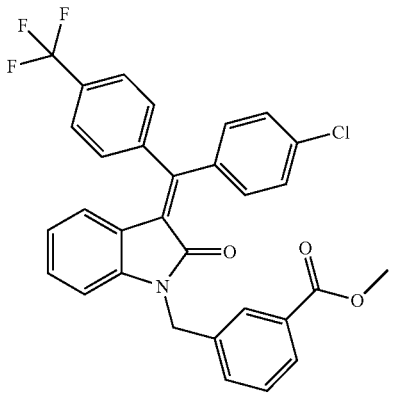 [SMILES: COC(=O)c1cccc(CN2C(=O)/C(=C(\c3ccc(Cl)cc3)c3ccc(C(F)(F)F)cc3)c3ccccc32)c1]

The title compound was prepared in analogy to Example 5 starting from 1-iodo-4-trifluoromethyl-benzene (commercially available) and 3-({[3-(4-chloro-phenyl)-propynoyl]-phenyl-amino}-methyl)-benzoic acid methyl ester. $^1$H NMR (300 Hz, CDCl$_3$): δppm 3.91 (s, 3H), 4.96 (s, 2H), 6.37 (d, 1H), 6.66-6.71 (m, 2H), 7.08 (t, 1H), 7.26-7.52 (m, 9H), 7.73 (d, 2H), 7.94 (d, 1H), 8.01 (s, 1H).

Example 36

(4-{3-[1-(4-Chloro-phenyl)-1-phenyl-meth-(E)-ylidene]-2-oxo-2,3-dihydro-indol-1-ylmethyl}-phenoxy)-acetic acid ethyl ester

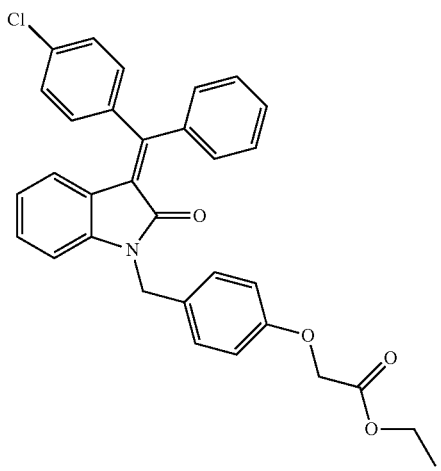 [SMILES: CCOC(=O)COc1ccc(CN2C(=O)/C(=C(\c3ccccc3)c3ccc(Cl)cc3)c3ccccc32)cc1]

The title compound was prepared in analogy to Example 5 starting from 1-chloro-4-iodo-benzene (commercially available) and (4-{[phenyl-(3-phenyl-propynoyl)-amino]-methyl}-phenoxy)-acetic acid ethyl ester. $^1$H NMR (300 Hz, CDCl$_3$): δppm 1.28 (t, 3H), 4.26 (q, 2H), 4.57 (s, 2H), 4.84 (s, 2H), 6.51 (d, 1H), 6.67-6.71 (m, 2H), 6.83 (d, 2H), 7.08 (t, 1H), 7.24-7.42 (m, 11H).

Example 37

3-{3-[1-(4-Chloro-phenyl)-1-phenyl-meth-(E)-ylidene]-2-oxo-2,3-dihydro-indol-1-ylmethyl}-N-isopropyl-benzamide

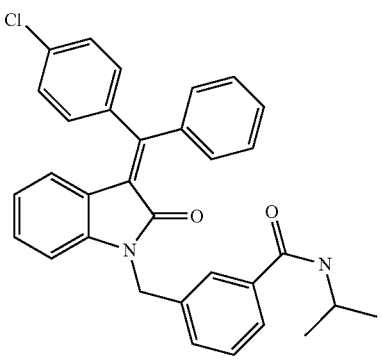 [SMILES: CC(C)NC(=O)c1cccc(CN2C(=O)/C(=C(\c3ccccc3)c3ccc(Cl)cc3)c3ccccc32)c1]

The title compound was prepared in analogy to Example 5 starting from 1-chloro-4-iodo-benzene (commercially available) and N-isopropyl-3-{[phenyl-(3-phenyl-propynoyl)-amino]-methyl}-benzamide. $^1$H NMR (CDCl$_3$, 300 MHz) δppm 7.74 (s, 1H), 7.60 (d, 1H), 7.26-7.43 (m, 10H), 7.07 (dt, 2H), 6.70 (t, 1H), 6.68 (d, 1H), 6.53 (d, 1H), 5.99 (d, 1H), 4.94 (s, 2H), 4.26 (m, 1H), 1.26 (s, 3H), 1.24 (s, 3H).

Example 38

6-{3-[1-(4-Chloro-phenyl)-1-phenyl-meth-(E)-ylidene]-2-oxo-2,3-dihydro-indol-1-ylmethyl}-nicotinic acid methyl ester

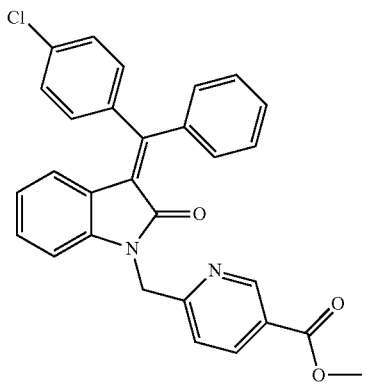 [SMILES: COC(=O)c1ccc(CN2C(=O)/C(=C(\c3ccccc3)c3ccc(Cl)cc3)c3ccccc32)nc1]

The title compound was prepared in analogy to Example 5 starting from 1-chloro-4-iodo-benzene (commercially available) and 6-{[phenyl-(3-phenyl-propynoyl)-amino]-methyl}-nicotinic acid methyl ester. $^1$H NMR (300 Hz, CDCl$_3$): δppm 3.93 (s, 3H), 5.10 (s, 2H), 6.54 (d, 1H), 6.57-6.75 (m, 2H), 7.08 (t, 1H), 7.28-7.44 (m, 10H), 8.20 (d, 1H), 9.16 (s, 1H).

Example 39

2-{3-[1-(4-Chloro-phenyl)-1-phenyl-meth-(E)-ylidene]-2-oxo-2,3-dihydro-indol-1-ylmethyl}-thiazole-4-carboxylic acid ethyl ester

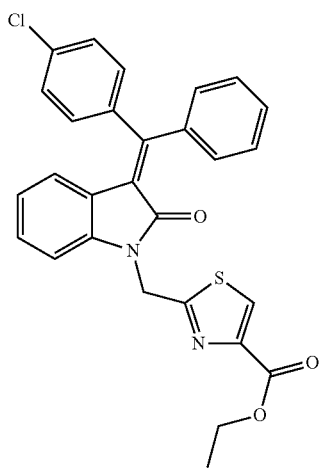 [SMILES: CCOC(=O)c1csc(CN2C(=O)/C(=C(\c3ccccc3)c3ccc(Cl)cc3)c3ccccc32)n1]

The title compound was prepared in analogy to Example 5 starting from 1-chloro-4-iodo-benzene (commercially available) and 2-{[phenyl-(3-phenyl-propynoyl)-amino]-methyl}-thiazole-4-carboxylic acid ethyl ester. $^1$H NMR (300 Hz, CDCl$_3$): δppm 1.39 (t, 3H), 4.44 (q, 2H), 5.27 (s, 2H), 6.58 (d, 1H), 6.78 (t, 1H), 6.88 (d, 1H), 7.13 (t, 1H), 7.31-7.43 (m, 9H), 8.10 (s, 1H).

Example 40

3-[1-(4-Chloro-phenyl)-1-phenyl-meth-(E)-ylidene]-1-(4-methoxy-benzyl)-1,3-dihydro-indol-2-one

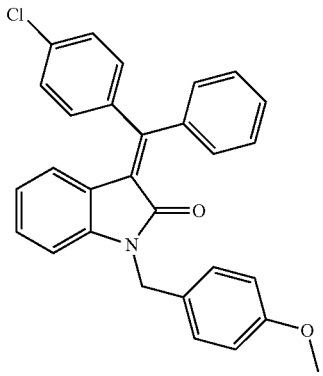 [SMILES: COc1ccc(CN2C(=O)/C(=C(\c3ccccc3)c3ccc(Cl)cc3)c3ccccc32)cc1]

The title compound was prepared in analogy to Example 5 starting from 1-chloro-4-iodo-benzene (commercially available) and 3-phenyl-propynoic acid (4-methoxy-benzyl)-phenylamide. $^1$H NMR (300 Hz, CDCl$_3$): δppm 3.77 (s, 3H), 4.88 (s, 2H), 6.53 (d, 1H), 6.67-6.71 (m, 2H), 6.80 (dd, 1H), 6.85-6.90 (m, 2H), 7.07 (t, 1H), 7.19-7.43 (m, 10H).

Example 41

3-[1-(4-Chloro-phenyl)-1-phenyl-meth-(E)-ylidene]-1-(3,4,5-trihydroxy-benzyl)-1,3-dihydro-indol-2-one; and Example 42

3-[1-(4-Chloro-phenyl)-1-phenyl-meth-(Z)-ylidene]-1-(3,4,5-trihydroxy-benzyl)-1,3-dihydro-indol-2-one

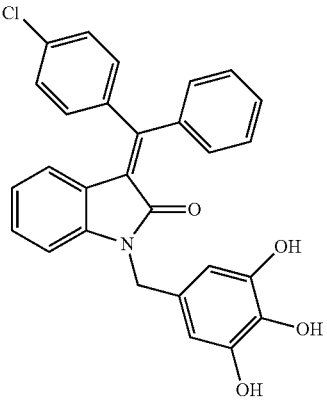

-continued

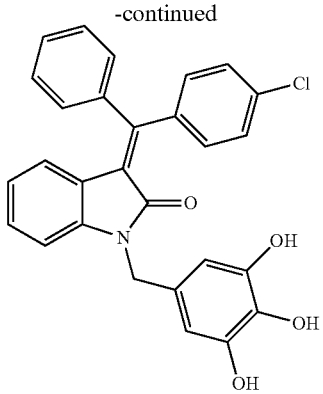

3-Phenyl-propynoic acid phenyl-(3,4,5-trimethoxy-benzyl)-amide

3-Phenyl-propynoic acid phenylamide (951.4 mg, 4.3 mmol), 5-bromomethyl-1,2,3-trimethoxy-benzene (1.35 g, 5.16 mmol), and $Cs_2CO_3$ (2.1 g, 6.45 mmol) were dissolved in DMF (20 ml). The mixture was stirred at room temperature for 16 h. The mixture was poured into water and extracted with ethyl acetate, dried over anhydrous sodium sulfate and concentrated under reduced pressure. Purification was by flash column chromatography on silica gel, eluting with hexanes-EtOAc (6:1 and then 4:1) afforded 3-phenyl-propynoic acid phenyl-(3,4,5-trimethoxy-benzyl)-amide 1.03 g (65%).

3-[1-(4-Chloro-phenyl)-1-phenyl-meth-(E)-ylidene]-1-(3,4,5-trimethoxy-benzyl)-1,3-dihydro-indol-2-one and 3-[1-(4-Chloro-phenyl)-1-phenyl-meth-(Z)-ylidene]-1-(3,4,5-trimethoxy-benzyl)-1,3-dihydro-indol-2-one To a solution of 3-phenyl-propynoic acid phenyl-(3,4,5-trimethoxy-benzyl)-amide (401.5 mg, 1 mmol) in THF (5 ml) were added palladium(II) acetate (11.2 mg, 0.05 mmol), triphenylphosphine (26.2 mg, 0.1 mmol), 1-chloro-4-iodo-benzene (262.3 mg, 1.1 mmol) and cesium fluoride (456 mg, 3 mmol) at room temperature. The solution was stirred for 3 h at 110° C. under an argon atmosphere. After being quenched with water, the mixture was extracted with ethyl acetate, dried over magnesium sulfate and concentrated under reduced pressure. The residue was purified by flash column chromatography on silica gel eluting with (hexane/ethyl acetate=5/1) to give a mixture of 3-[1-(4-chloro-phenyl)-1-phenyl-meth-(E)-ylidene]-1-(3,4,5-trimethoxy-benzyl)-1,3-dihydro-indol-2-one and 3-[1-(4-chloro-phenyl)-1-phenyl-meth-(Z)-ylidene]-1-(3,4,5-trimethoxy-benzyl)-1,3-dihydro-indol-2-one, yield 317 mg (62%);

3-[1-(4-Chloro-phenyl)-1-phenyl-meth-(E)-ylidene]-1-(3,4,5-trihydroxy-benzyl)-1,3-dihydro-indol-2-one and 3-[1-(4-chloro-phenyl)-1-phenyl-meth-(Z)-ylidene]-1-(3,4,5-trihydroxy-benzyl)-1,3-dihydro-indol-2-one To a solution of 3-[1-(4-chloro-phenyl)-1-phenyl-meth-(E)-ylidene]-1-(3,4,5-trimethoxy-benzyl)-1,3-dihydro-indol-2-one and 3-[1-(4-chloro-phenyl)-1-phenyl-meth-(Z)-ylidene]-1-(3,4,5-trimethoxy-benzyl)-1,3-dihydro-indol-2-one (317 mg, 0.62 mmol) in dichloromethane (5 ml) was added a solution of boron tribromide (1M in $CH_2Cl_2$, 3 ml) at room temperature. The mixture was stirred at room temperature for 5 h. After being quenched by pouring into ice water, the mixture was extracted with ethyl acetate, dried over magnesium sulfate and concentrated under reduced pressure. The residue was purified by flash column chromatography on silica gel eluting with (hexane/ethyl acetate=1/1) to give 3-[1-(4-chloro-phenyl)-1-phenyl-meth-(E)-ylidene]-1-(3,4,5-trihydroxy-benzyl)-1,3-dihydro-indol-2-one (60 mg). $^1$H NMR (300 Hz, $CDCl_3$): δppm 4.66 (s, 2H), 5.60 (b, 1H), 6.31 (s, 2H), 6.56 (d, 1H), 6.67-6.82 (m, 2H), 7.00-7.23 (m, 8H), 7.38 (d, 2H); and 3-[1-(4-Chloro-phenyl)-1-phenyl-meth-(Z)-ylidene]-1-(3,4,5-trihydroxy-benzyl)-1,3-dihydro-indol-2-one (40 mg). $^1$H NMR (300 Hz, $CDCl_3$): δppm 4.72 (s, 2H), 5.33 (b, 1H), 6.05 (b, 1H), 6.40 (s, 2H), 6.44 (d, 1H), 6.67 (t, 1H), 6.82 (d, 1H), 7.00 (d, 2H), 7.10-7.15 (m, 3H), 7.23-7.26 (m, 2H), 7.37-7.46 (m, 3H).

Example 43

3-[1-(4-Chloro-phenyl)-1-phenyl-meth-(E)-ylidene]-1-(4-hydroxy-benzyl)-1,3-dihydro-indol-2-one

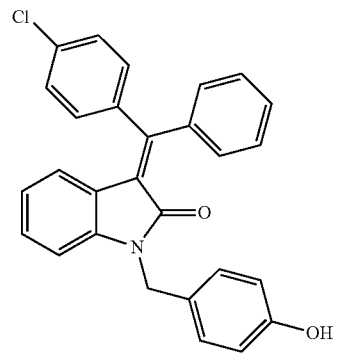 [SMILES: O=C1/C(=C(\c2ccccc2)c2ccc(Cl)cc2)c2ccccc2N1Cc1ccc(O)cc1]

The title compound was prepared in analogy to Example 41 starting from 3-[1-(4-chloro-phenyl)-1-phenyl-meth-(E)-ylidene]-1-(4-methoxy-benzyl)-1,3-dihydro-indol-2-one. $^1$H NMR (300 Hz, $CDCl_3$): δppm 4.81 (s, 2H), 6.51 (d, 1H), 6.53-6.74 (m, 4H), 7.08-7.11 (m, 3H), 7.24-7.42 (m, 9H).

Example 44

3-{3-[1-(4-Chloro-phenyl)-1-phenyl-meth-(E)-ylidene]-2-oxo-2,3-dihydro-indol-1-ylmethyl}-benzoic acid

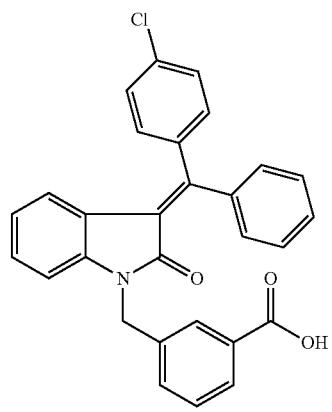 [SMILES: O=C(O)c1cccc(CN2C(=O)/C(=C(\c3ccccc3)c3ccc(Cl)cc3)c3ccccc32)c1]

3-{3-[1-(4-chloro-phenyl)-1-phenyl-meth-(E)-ylidene]-2-oxo-2,3-dihydro-indol-1-ylmethyl}-benzoic acid methyl ester (94 mg, 0.2 mmol) was dissolved in THF (2 ml) and water (2 ml) and LiOH.H₂O (42 mg, 1 mmol) was added in one portion. The mixture was stirred at 50° C. for 16 h. The mixture was concentrated under reduced pressure, and acidified to pH=3. Purification by preparative HPLC afforded 3-((3-((4-chlorophenyl)(phenyl)meth-(E)-ylene)-2-oxoindolin-1-yl)methyl)benzoic acid as light yellow powder. Yield 30 mg (70%). ¹H NMR (CDCl₃, 300 MHz) δ ppm 8.06 (s, 1H), 7.99 (d, 1H), 7.55 (d, 1H), 7.29-7.43 (m, 10H), 7.09 (t, 1H), 6.74-6.65 (m, 2H), 6.55 (d, 1H), Example 45

3-{3-[1-(4-Fluoro-phenyl)-1-phenyl-meth-(E)-ylidene]-2-oxo-2,3-dihydro-indol-1-ylmethyl}-benzoic acid

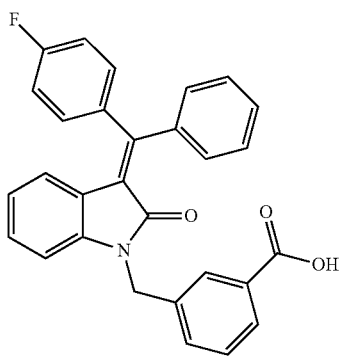 [SMILES: O=C(O)c1cccc(CN2C(=O)/C(=C(\c3ccccc3)c3ccc(F)cc3)c3ccccc32)c1]

The title compound was prepared in analogy to Example 44 starting from 3-{3-[1-(4-fluoro-phenyl)-1-phenyl-meth-(E)-ylidene]-2-oxo-2,3-dihydro-indol-1-ylmethyl}-benzoic acid methyl ester. ¹H NMR (CDCl₃, 300 MHz) δppm 8.07 (s, 1H), 8.00 (d, 1H), 7.56 (d, 1H), 7.33-7.48 (m, 8H), 7.07-7.17 (m, 3H), 6.66-6.74 (m, 2H), 6.52 (d, 1H), 4.99 (s, 2H).

Example 46

3-{3-[1-(4-Methoxy-phenyl)-1-phenyl-meth-(E)-ylidene]-2-oxo-2,3-dihydro-indol-1-ylmethyl}-benzoic acid

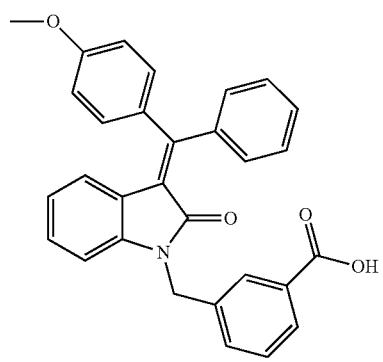 [SMILES: COc1ccc(/C(=C2/C(=O)N(Cc3cccc(C(=O)O)c3)c3ccccc32)c2ccccc2)cc1]

The title compound was prepared in analogy to Example 44 starting from 3-{3-[1-(4-methoxy-phenyl)-1-phenyl-meth-(E)-ylidene]-2-oxo-2,3-dihydro-indol-1-ylmethyl}-benzoic acid methyl ester. ¹H NMR (CDCl₃, 300 MHz) δppm 8.07 (s, 1H), 8.00 (d, 1H), 7.55 (d, 1H), 7.26-7.38 (m, 8H), 7.07 (m, 1H), 6.94 (m, 2H), 6.65-6.71 (m, 3H), 4.98 (s, 2H), 3.88 (s, 3H).

Example 47

3-{3-[1-(4-Chloro-phenyl)-1-(2-methoxy-phenyl)-meth-(Z)-ylidene]-2-oxo-2,3-dihydro-indol-1-ylmethyl}-benzoic acid

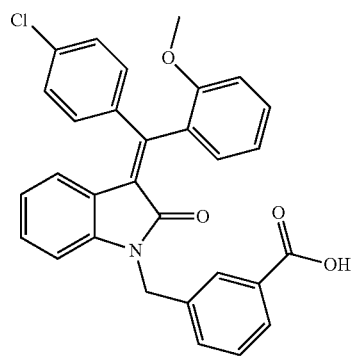 [SMILES: COc1ccccc1/C(=C1\C(=O)N(Cc2cccc(C(=O)O)c2)c2ccccc21)c1ccc(Cl)cc1]

The title compound was prepared in analogy to Example 44 starting from 3-{3-[1-(4-chloro-phenyl)-1-(2-methoxy-phenyl)-meth-(Z)-ylidene]-2-oxo-2,3-dihydro-indol-1 ylmethyl}-benzoic acid methyl ester. ¹H NMR (CDCl₃, 300 MHz) δppm 8.04 (s, 1H), 7.99 (d, 1H), 7.54 (d, 1H), 7.32-7.44 (m, 6H), 7.07-7.15 (m, 2H), 6.93-7.01 (m, 2H), 6.73 (t, 1H), 6.64 (t, 2H), 4.95 (dd, 2H), 3.90 (s, 3H), 3.72 (s, 3H).

Example 48

3-{2-Oxo-3-[1-phenyl-1-(4-trifluoromethyl-phenyl)-meth-(E)-ylidene]-2,3-dihydro-indol-1-ylmethyl}-benzoic acid

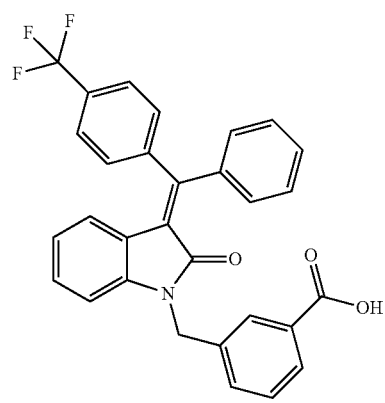 [SMILES: O=C(O)c1cccc(CN2C(=O)/C(=C(\c3ccccc3)c3ccc(C(F)(F)F)cc3)c3ccccc32)c1]

The title compound was prepared in analogy to Example 44 starting from 3-{2-oxo-3-[1-phenyl-1-(4-trifluoromethyl-phenyl)-meth-(E)-ylidene]-2,3-dihydro-indol-1-ylmethyl}-benzoic acid methyl ester. ¹H NMR (300 Hz, CDCl₃): δppm 4.98 (s, 2H), 6.40 (d, 1H), 6.68 (dd, 2H), 7.10 (t, 1H), 7.35-7.55 (m, 9H), 7.71 (d, 2H), 7.99 (d, 1H), 8.07 (s, 1H).

Example 49

3-{2-Oxo-3-[1-phenyl-1-(2-trifluoromethoxy-phenyl)-meth-(E)-ylidene]-2,3-dihydro-indol-1-ylmethyl}-benzoic acid

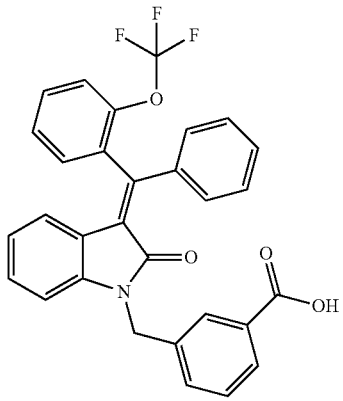 [SMILES: O=C(O)c1cccc(CN2C(=O)/C(=C(\c3ccccc3)c3ccccc3OC(F)(F)F)c3ccccc32)c1]

The title compound was prepared in analogy to Example 44 starting from 3-{2-oxo-3-[1-phenyl-1-(2-trifluoromethoxy-phenyl)-meth-(E)-ylidene]-2,3-dihydro-indol-1-ylmethyl}-benzoic acid methyl ester. $^1$H NMR (300 Hz, CDCl$_3$): δppm 3.91 (s, 3H), 5.96 (s, 2H), 6.37 (d, 1H), 6.64-6.72 (m, 2H), 7.07 (dt, 1H), 7.51-7.33 (m, H), 7.70 (d, 2H) 7.93 (d, 1H), 8.01 (s, 1H).

Example 50

3-{3-[1-(3-Chloro-4-fluoro-phenyl)-1-phenyl-meth-(E)-ylidene]-2-oxo-2,3-dihydro-indol-1-ylmethyl}-benzoic acid

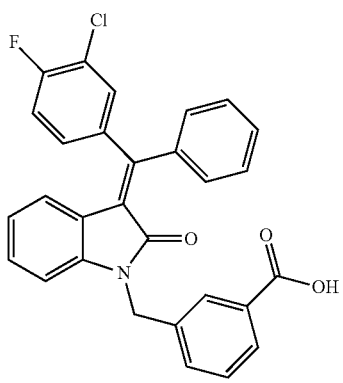

The title compound was prepared in analogy to Example 44 starting from 3-{3-[1-(3-chloro-4-fluoro-phenyl)-1-phenyl-meth-(E)-ylidene]-2-oxo-2,3-dihydro-indol-1-ylmethyl}-benzoic acid methyl ester. $^1$H NMR (CDCl$_3$, 300 MHz) δppm 8.07 (s, 1H), 8.01 (d, 1H), 7.56 (d, 1H), 7.34-7.45 (m, 6H), 7.22-7.28 (m, 3H), 7.11 (dt, 1H), 6.74 (dt, 1H), 6.68 (d, 1H), 6.53 (d, 1H), 4.98 (s, 2H).

Example 51

3-{2-Oxo-3-[1-phenyl-1-(3,4,5-trimethoxy-phenyl)-meth-(E)-ylidene]-2,3-dihydro-indol-1-ylmethyl}-benzoic acid

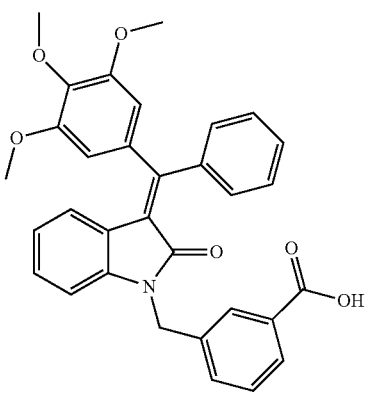 [SMILES: COc1cc(/C(=C2/C(=O)N(Cc3cccc(C(=O)O)c3)c3ccccc32)c2ccccc2)cc(OC)c1OC]

The title compound was prepared in analogy to Example 44 starting from 3-{2-oxo-3-[1-phenyl-1-(3,4,5-trimethoxy-phenyl)-meth-(E)-ylidene]-2,3-dihydro-indol-1-ylmethyl}-benzoic acid methyl ester. $^1$H NMR (300 Hz, CDCl$_3$): δppm 3.79 (s, 6H), 3.94 (s, 3H), 4.98 (s, 2H), 6.55 (s, 2H), 6.61-6.72 (m, 4H), 7.08 (t, 1H), 7.40-7.45 (m, 5H), 7.58 (d, 1H), 7.99 (d, 1H), 8.07 (s, 1H).

Example 52

3-{3-[1-(3-Chloro-phenyl)-1-phenyl-meth-(E)-ylidene]-2-oxo-2,3-dihydro-indol-1-ylmethyl}-benzoic acid

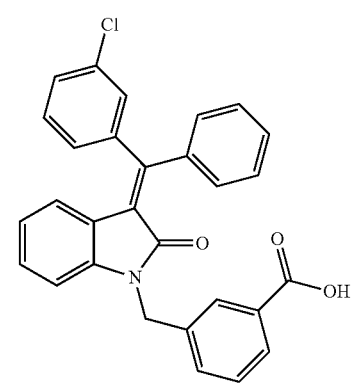 [SMILES: O=C(O)c1cccc(CN2C(=O)/C(=C(\c3ccccc3)c3cccc(Cl)c3)c3ccccc32)c1]

The title compound was prepared in analogy to Example 44 starting from 3-{3-[1-(3-chloro-phenyl)-1-phenyl-meth-(E)-ylidene]-2-oxo-2,3-dihydro-indol-1-ylmethyl}-benzoic acid methyl ester. $^1$H NMR (CDCl$_3$, 300 MHz) δppm 8.07 (s, 1H), 7.90 (d, 1H), 7.56 (d, 1H), 7.26-7.50 (m, 10H), 7.09 (t, 1H), 6.66-6.70 (m, 2H), 6.45 (d, 1H), 4.98 (s, 2H).

Example 53

3-{3-[1-(4-Chloro-phenyl)-1-phenyl-meth-(E)-ylidene]-5-fluoro-2-oxo-2,3-dihydro-indol-1-ylmethyl}-benzoic acid

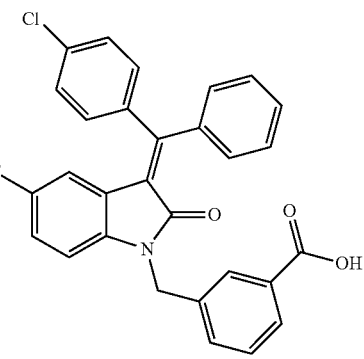

The title compound was prepared in analogy to Example 44 starting from 3-{3-[1-(4-chloro-phenyl)-1-phenyl-meth-(E)-ylidene]-5-fluoro-2-oxo-2,3-dihydro-indol-1-ylmethyl}-benzoic acid methyl ester. $^1$H NMR (300 Hz, CDCl$_3$): δppm 4.97 (s, 2H), 6.26 (dd, 1H), 6.55 (dd, 2H), 6.77-6.80 (m, 1H), 7.10 (d, 2H), 7.33-7.48 (m, 7H), 7.53 (d, 2H), 8.01 (d, 1H), 8.04 (s, 1H).

Example 54

3-{3-[1-(3,5-Dichloro-phenyl)-1-phenyl-meth-(E)-ylidene]-2-oxo-2,3-dihydro-indol-1-ylmethyl}-benzoic acid

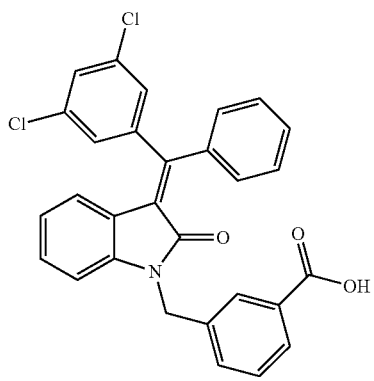 [SMILES: O=C(O)c1cccc(CN2C(=O)/C(=C(\c3ccccc3)c3cc(Cl)cc(Cl)c3)c3ccccc32)c1]

The title compound was prepared in analogy to Example 44 starting from 3-{3-[1-(3,5-dichloro-phenyl)-1-phenyl-meth-(E)-ylidene]-2-oxo-2,3-dihydro-indol-1-ylmethyl}-benzoic acid methyl ester. $^1$H NMR (300 Hz, CDCl$_3$): δppm 4.96 (s, 2H), 6.48 (d, 1H), 6.65-6.78 (m, 2H), 7.13 (t, 2H), 7.33-7.43 (m, 8H), 7.56 (d, 1H), 7.98 (d, 1H), 8.08 (s, 1H).

Example 55

3-{3-[1-(2,3-Dichloro-phenyl)-1-phenyl-meth-(E)-ylidene]-2-oxo-2,3-dihydro-indol-1-ylmethyl}-benzoic acid

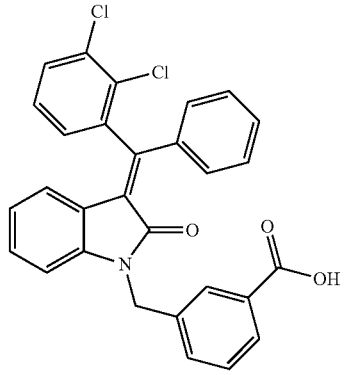 [SMILES: O=C(O)c1cccc(CN2C(=O)/C(=C(\c3ccccc3)c3cccc(Cl)c3Cl)c3ccccc32)c1]

The title compound was prepared in analogy to Example 44 starting from 3-{3-[1-(2,3-dichloro-phenyl)-1-phenyl-meth-(E)-ylidene]-2-oxo-2,3-dihydro-indol-1-ylmethyl}-benzoic acid methyl ester. $^1$H NMR (CDCl$_3$, 300 MHz) δppm 8.07 (s, 1H), 8.01 (d, 1H), 7.33-7.57 (m, 9H), 7.22-7.26 (m, 1H), 7.12 (t, 1H), 6.75 (t, 1H), 6.68 (d, 1H), 6.56 (d, 1H), 4.97 (s, 2H).

Example 56

2-{3-[1-(4-Chloro-phenyl)-1-phenyl-meth-(E)-ylidene]-2-oxo-2,3-dihydro-indol-1-ylmethyl}-benzoic acid

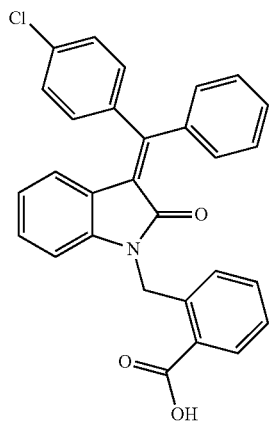 [SMILES: O=C(O)c1ccccc1CN1C(=O)/C(=C(\c2ccccc2)c2ccc(Cl)cc2)c2ccccc21]

The title compound was prepared in analogy to Example 44 starting from 2-{3-[1-(4-chloro-phenyl)-1-phenyl-meth-(E)-ylidene]-2-oxo-2,3-dihydro-indol-1-ylmethyl}-benzoic acid methyl ester. $^1$H NMR (CDCl$_3$, 300 MHz) δppm 8.10 (d, 1H), 7.32-7.48 (m, 11H), 7.18 (d, 1H), 7.11 (t, 1H), 6.75 (t, 1H), 6.65 (d, 1H), 6.58 (d, 1H), 5.39 (s, 2H).

Example 57

4-{3-[1-(4-Chloro-phenyl)-1-phenyl-meth-(E)-ylidene]-2-oxo-2,3-dihydro-indol-1-ylmethyl}-benzoic acid

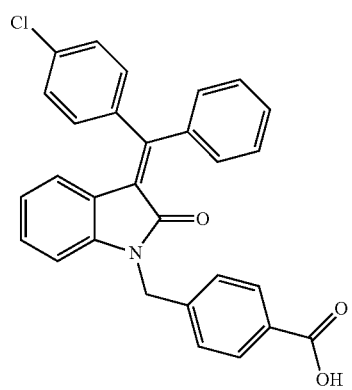 [SMILES: O=C(O)c1ccc(CN2C(=O)/C(=C(\c3ccccc3)c3ccc(Cl)cc3)c3ccccc32)cc1]

The title compound was prepared in analogy to Example 44 starting from 4-{3-[1-(4-chloro-phenyl)-1-phenyl-meth-(E)-ylidene]-2-oxo-2,3-dihydro-indol-1-ylmethyl}-benzoic acid methyl ester. $^1$H NMR (CDCl$_3$, 300 MHz) δppm 8.05 (d, 2H), 7.29-7.44 (m, 11H), 7.09 (t, 1H), 6.72 (t, 1H), 7.29 (d, 1H), 6.59 (d, 1H), 4.98 (s, 2H), 3.89 (s, 3H).

Example 58

3-{3-[1-(4-Chloro-phenyl)-1-phenyl-meth-(E)-ylidene]-5-methoxy-2-oxo-2,3-dihydro-indol-1-ylmethyl}-benzoic acid

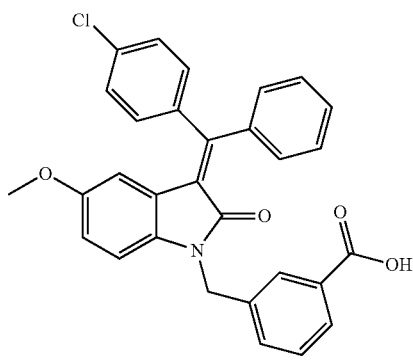 [SMILES: COc1ccc2c(c1)/C(=C(/c1ccccc1)c1ccc(Cl)cc1)C(=O)N2Cc1cccc(C(=O)O)c1]

The title compound was prepared in analogy to Example 44 starting from 3-{3-[1-(4-chloro-phenyl)-1-phenyl-meth-(E)-ylidene]-5-methoxy-2-oxo-2,3-dihydro-indol-1-ylmethyl}-benzoic acid methyl ester. $^1$H NMR (300 Hz, CDCl$_3$): δppm 3.49 (s, 3H), 4.95 (s, 2H), 6.10 (dd, 1H), 6.51 (d, 1H), 6.64 (dd, 1H), 7.25-7.45 (m, 10H), 7.54 (d, 1H), 8.00 (d, 1H), 8.05 (s, 1H).

Example 59

6-{3-[1-(4-Chloro-phenyl)-1-phenyl-meth-(E)-ylidene]-2-oxo-2,3-dihydro-indol-1-ylmethyl}-nicotinic acid

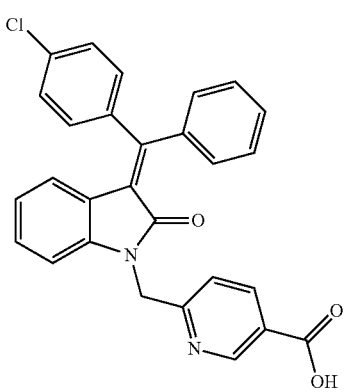 [SMILES: O=C(O)c1ccc(CN2C(=O)/C(=C(\c3ccccc3)c3ccc(Cl)cc3)c3ccccc32)nc1]

The title compound was prepared in analogy to Example 44 starting from 6-{3-[1-(4-chloro-phenyl)-1-phenyl-meth-(E)-ylidene]-2-oxo-2,3-dihydro-indol-1-ylmethyl}-nicotinic acid methyl ester. $^1$H NMR (300 Hz, CDCl$_3$): δppm 5.19 (s, 2H), 6.56 (d, 1H), 6.58-6.77 (m, 2H), 7.09 (t, 1H), 7.28-7.44 (m, 10H), 8.30 (d, 1H), 9.26 (s, 1H).

Example 60

3-{3-[1-(4-Chloro-phenyl)-1-phenyl-meth-(E)-ylidene]-4-fluoro-2-oxo-2,3-dihydro-indol-1-ylmethyl}-benzoic acid

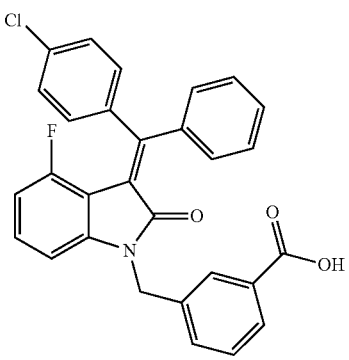 [SMILES: O=C(O)c1cccc(CN2C(=O)/C(=C(\c3ccccc3)c3ccc(Cl)cc3)c3c(F)cccc32)c1]

The title compound was prepared in analogy to Example 44 starting from 3-{3-[1-(4-chloro-phenyl)-1-phenyl-meth-(E)-ylidene]-4-fluoro-2-oxo-2,3-dihydro-indol-1-ylmethyl}-benzoic acid methyl ester. $^1$H NMR (300 Hz, CDCl$_3$): δppm 4.97 (s, 2H), 6.39-6.51 (m, 2H), 7.25-7.45 (m, 11H), 7.53 (d, 1H), 7.99 (d, 1H), 8.00 (s, 1H).

Example 61

3-{3-[1-(4-Chloro-phenyl)-1-phenyl-meth-(E)-ylidene]-6-fluoro-2-oxo-2,3-dihydro-indol-1-ylmethyl}-benzoic acid

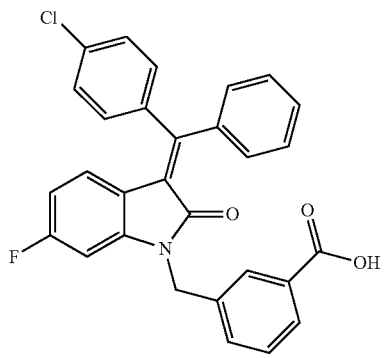 [SMILES: O=C(O)c1cccc(CN2C(=O)/C(=C(\c3ccccc3)c3ccc(Cl)cc3)c3ccc(F)cc32)c1]

The title compound was prepared in analogy to Example 44 starting from 3-{3-[1-(4-chloro-phenyl)-1-phenyl-meth-(E)-ylidene]-6-fluoro-2-oxo-2,3-dihydro-indol-1-ylmethyl}-benzoic acid methyl ester. $^1$H NMR (300 Hz, CDCl$_3$): δppm 4.88 (s, 2H), 6.40-6.429 (m, 1H), 7.08-7.10 (m, 1H), 7.20 (d, 1H), 7.31-7.38 (m, 10H), 7.42 (d, 1H), 7.90 (d, 1H), 7.94 (s, 1H).

Example 62

3-{3-[1-(2-Methylsulfanyl-phenyl)-1-phenyl-meth-(E)-ylidene]-2-oxo-2,3-dihydro-indol-1-ylmethyl}-benzoic acid

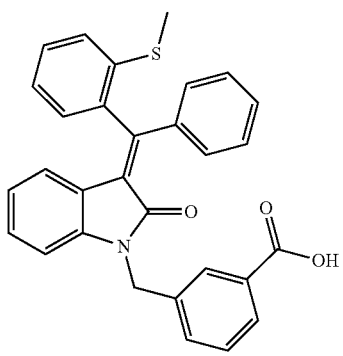 [SMILES: CSc1ccccc1/C(=C1/C(=O)N(Cc2cccc(C(=O)O)c2)c2ccccc21)c1ccccc1]

The title compound was prepared in analogy to Example 44 starting from 3-{3-[1-(2-methylsulfanyl-phenyl)-1-phenyl-meth-(E)-ylidene]-2-oxo-2,3-dihydro-indol-1-ylmethyl}-benzoic acid methyl ester. $^1$H NMR (300 Hz, CDCl$_3$): δppm 2.31 (s, 3H), 5.00 (dd, 2H), 6.04 (d, 1H), 6.63-6.64 (m, 2H), 7.07 (t, 1H), 7.26-7.30 (m, 2H), 7.33-7.46 (m, 6H), 7.58-7.60 (m, 2H), 7.99 (d, 1H), 8.07 (s, 1H).

Example 63

3-{2-Oxo-3-[1-phenyl-1-pyridin-3-yl-meth-(E)-ylidene]-2,3-dihydro-indol-1-ylmethyl}-benzoic acid

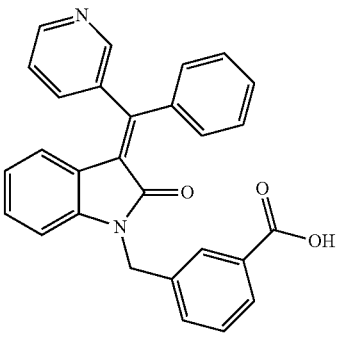 [SMILES: O=C(O)c1cccc(CN2C(=O)/C(=C(\c3ccccc3)c3cccnc3)c3ccccc32)c1]

The title compound was prepared in analogy to Example 44 starting from 3-{2-oxo-3-[1-phenyl-1-pyridin-3-yl-meth-(E)-ylidene]-2,3-dihydro-indol-1-ylmethyl}-benzoic acid methyl ester. $^1$H NMR (300 Hz, CDCl$_3$): δppm 4.98 (s, 2H), 6.40 (d, 1H), 6.65-6.68 (m, 2H), 7.07 (t, 1H), 7.35-7.42 (m, 8H), 7.58 (d, 2H), 7.69 (d, 1H), 7.99 (d, 1H), 8.04 (s, 1H).

Example 64

3-{3-[1-(2-Chloro-5-trifluoromethyl-phenyl)-1-phenyl-meth-(E)-ylidene]-2-oxo-2,3-dihydro-indol-1-ylmethyl}-benzoic acid

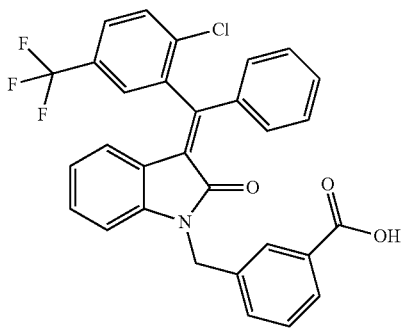 [SMILES: O=C(O)c1cccc(CN2C(=O)/C(=C(\c3ccccc3)c3cc(C(F)(F)F)ccc3Cl)c3ccccc32)c1]

The title compound was prepared in analogy to Example 44 starting from 3-{3-[1-(2-chloro-5-trifluoromethyl-phenyl)-1-phenyl-meth-(E)-ylidene]-2-oxo-2,3-dihydro-indol-1-ylmethyl}-benzoic acid methyl ester. $^1$H NMR (CDCl$_3$, 300 MHz) δppm 8.06 (s, 1H), 8.00 (d, 1H), 7.40-7.67 (m, 10H), 7.11 (t, 1H), 6.66-6.72 (m, 2H), 5.98 (d, 1H), 4.89-5.06 (m, 2H), 3.91 (s, 3H).

Example 65

3-{3-[1-(3,5-Bis-trifluoromethyl-phenyl)-1-phenyl-meth-(E)-ylidene]-2-oxo-2,3-dihydro-indol-1-ylmethyl}-benzoic acid

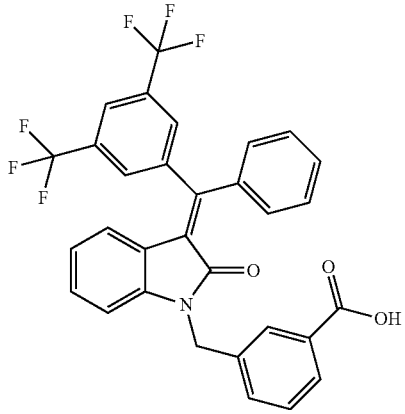 [SMILES: O=C(O)c1cccc(CN2C(=O)/C(=C(\c3ccccc3)c3cc(C(F)(F)F)cc(C(F)(F)F)c3)c3ccccc32)c1]

The title compound was prepared in analogy to Example 44 starting from 3-{3-[1-(3,5-bis-trifluoromethyl-phenyl)-1-phenyl-meth-(E)-ylidene]-2-oxo-2,3-dihydro-indol-1-ylmethyl}-benzoic acid methyl ester. $^1$H NMR (CDCl$_3$, 300 MHz) δppm 8.24 (s, 1H), 7.95-8.10 (m, 4H), 7.78-7.87 (m, 3H), 7.67 (d, 2H), 7.29-7.58 (m, 6H), 7.21 (t, 1H), 6.68-6.71 (m, 2H), 6.27 (d, 1H), 4.98 (s, 2H), 3.91 (s, 3H).

Example 66

3-{2-Oxo-3-[1-phenyl-1-(3-trifluoromethyl-phenyl)-meth-(E)-ylidene]-2,3-dihydro-indol-1-ylmethyl}-benzoic acid

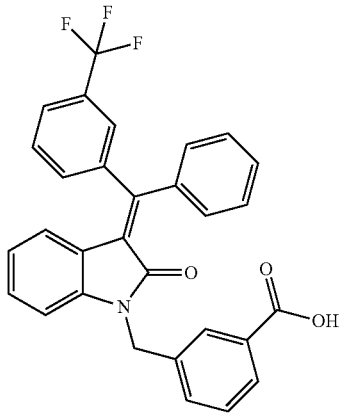 [SMILES: O=C(O)c1cccc(CN2C(=O)/C(=C(\c3ccccc3)c3cccc(C(F)(F)F)c3)c3ccccc32)c1]

The title compound was prepared in analogy to Example 44 starting from 3-{2-oxo-3-[1-phenyl-1-(3-trifluoromethyl-phenyl)-meth-(E)-ylidene]-2,3-dihydro-indol-1-ylmethyl}-benzoic acid methyl ester. $^1$H NMR (CDCl$_3$, 300 MHz) δppm 8.08 (s, 1H), 8.01 (d, 1H), 7.72 (d, 1H), 7.64-7.56 (m, 4H), 7.35-7.54 (m, 4H), 7.10 (dt, 1H), 6.66-6.70 (m, 2H), 6.33 (dd, 1H), 4.98 (s, 2H).

Example 67

3-{2-Oxo-3-[1-phenyl-1-(4-sulfamoyl-phenyl)-meth-(E)-ylidene]-2,3-dihydro-indol-1-ylmethyl}-benzoic acid

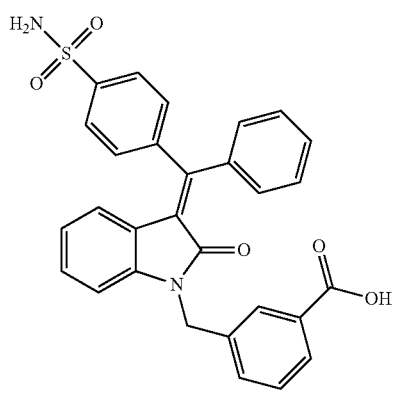 [SMILES: NS(=O)(=O)c1ccc(/C(=C2/C(=O)N(Cc3cccc(C(=O)O)c3)c3ccccc32)c2ccccc2)cc1]

The title compound was prepared in analogy to Example 44 starting from 3-{2-oxo-3-[1-phenyl-1-(4-sulfamoyl-phenyl)-meth-(E)-ylidene]-2,3-dihydro-indol-1-ylmethyl}-benzoic acid methyl ester. $^1$H NMR (300 Hz, CDCl$_3$): δppm 4.97 (s, 2H), 5.17 (s, 2H), 6.42 (d, 1H), 6.64-6.71 (m, 2H), 7.08 (t, 1H), 7.26-7.60 (m, 11H), 7.97 (s, 1H), 8.00 (s, 1H).

Example 68

3-{3-[1-(4-Chloro-phenyl)-1-phenyl-meth-(Z)-ylidene]-2-oxo-2,3-dihydro-indol-1-ylmethyl}-benzoic acid

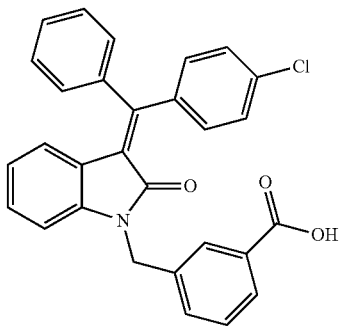 [SMILES: O=C(O)c1cccc(CN2C(=O)/C(=C(/c3ccccc3)c3ccc(Cl)cc3)c3ccccc32)c1]

The title compound was prepared in analogy to Example 44 starting from 3-{3-[1-(4-chloro-phenyl)-1-phenyl-meth-(Z)-ylidene]-2-oxo-2,3-dihydro-indol-1-ylmethyl}-benzoic acid methyl ester. $^1$H NMR (300 Hz, CDCl$_3$): δppm 4.96 (s, 2H), 6.42 (d, 1H), 6.63-6.66 (m, 2H), 7.06 (t, 1H), 7.33-7.52 (m, 11H), 7.92 (d, 1H), 8.01 (s, 1H).

Example 69

3-{3-[1-(4-Chloro-phenyl)-1-(4-trifluoromethyl-phenyl)-meth-(Z)-ylidene]-2-oxo-2,3-dihydro-indol-1-ylmethyl}-benzoic acid

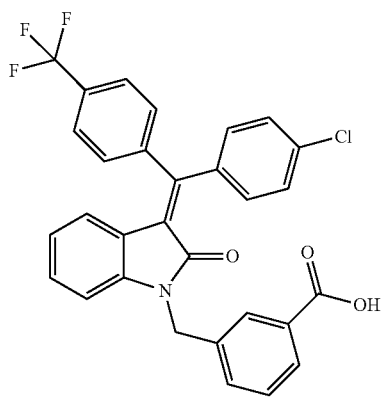 [SMILES: O=C(O)c1cccc(CN2C(=O)/C(=C(\c3ccc(Cl)cc3)c3ccc(C(F)(F)F)cc3)c3ccccc32)c1]

The title compound was prepared in analogy to Example 44 starting from 3-{3-[1-(4-chloro-phenyl)-1-(4-trifluoromethyl-phenyl)-meth-(Z)-ylidene]-2-oxo-2,3-dihydro-indol-1-ylmethyl}-benzoic acid methyl ester. $^1$H NMR (300 Hz, CDCl$_3$): δppm 4.98 (s, 2H), 6.38 (d, 1H), 6.68-6.73 (m, 2H), 7.08 (t, 1H), 7.26-7.52 (m, 9H), 7.72 (d, 2H), 8.01 (d, 1H), 8.08 (s, 1H).

Example 70

(4-{3-[1-(4-Chloro-phenyl)-1-phenyl-meth-(E)-ylidene]-2-oxo-2,3-dihydro-indol-1-ylmethyl}-phenoxy)-acetic acid

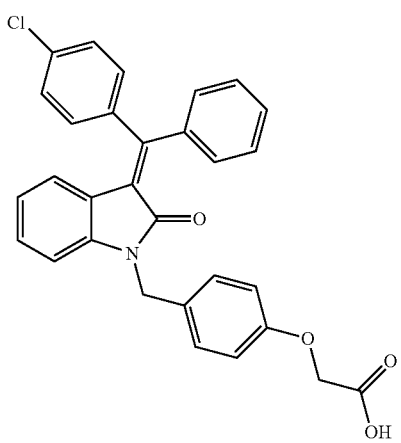 [SMILES: O=C(O)COc1ccc(CN2C(=O)/C(=C(\c3ccccc3)c3ccc(Cl)cc3)c3ccccc32)cc1]

The title compound was prepared in analogy to Example 44 starting from (4-{3-[1-(4-chloro-phenyl)-1-phenyl-meth-(E)-ylidene]-2-oxo-2,3-dihydro-indol-1-ylmethyl}-phenoxy)-acetic acid methyl ester. $^1$H NMR (300 Hz, CDCl$_3$): δppm 4.56 (s, 2H), 4.85 (s, 2H), 6.51 (d, 1H), 6.53-6.73 (m, 2H), 6.83 (d, 2H), 7.08 (t, 1H), 7.24-7.42 (m, 11H).

Example 71

3-{3-[1-(4-Isopropyl-phenyl)-1-phenyl-meth-(E)-ylidene]-2-oxo-2,3-dihydro-indol-1-ylmethyl}-benzoic acid

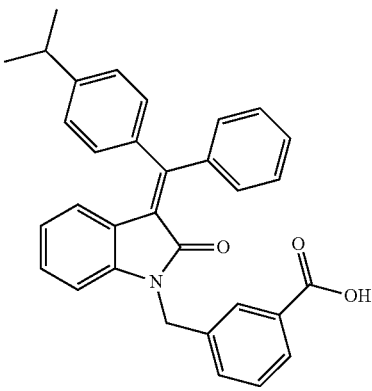 [SMILES: CC(C)c1ccc(/C(=C2/C(=O)N(Cc3cccc(C(=O)O)c3)c3ccccc32)c2ccccc2)cc1]

The title compound was prepared in analogy to Example 44 starting from 3-{3-[1-(4-isopropyl-phenyl)-1-phenyl-meth-(E)-ylidene]-2-oxo-2,3-dihydro-indol-1-ylmethyl}-benzoic acid methyl ester. $^1$H NMR (300 Hz, CDCl$_3$): δppm 1.31 (d, 6H), 2.94-3.01 (m, 1H), 4.99 (s, 2H), 6.56 (d, 1H), 6.67 (dd, 2H), 7.08 (t, 1H), 7.27 (s, 4H), 7.38-7.42 (m, 6H), 7.51 (d, 1H), 7.99 (d, 1H), 8.08 (s, 1H)

Example 72

3-{3-[1-(3,4-Difluoro-phenyl)-1-phenyl-meth-(E)-ylidene]-2-oxo-2,3-dihydro-indol-1-ylmethyl}-benzoic acid

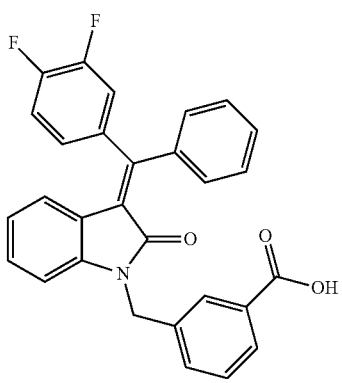 [SMILES: O=C(O)c1cccc(CN2C(=O)/C(=C(\c3ccccc3)c3ccc(F)c(F)c3)c3ccccc32)c1]

The title compound was prepared in analogy to Example 44 starting from 3-{3-[1-(3,4-difluoro-phenyl)-1-phenyl-meth-(E)-ylidene]-2-oxo-2,3-dihydro-indol-1-ylmethyl}-benzoic acid methyl ester. $^1$H NMR (300 Hz, CDCl$_3$): δppm 4.97 (s, 2H), 6.51 (d, 1H), 6.71 (m, 2H), 7.08-7.26 (m, 4H), 7.34-7.43 (m, 6H), 7.56 (d, 1H), 8.00 (d, 1H), 8.05 (s, 1H).

Example 73

3-{3-[1-(4-Chloro-phenyl)-1-phenyl-meth-(E)-ylidene]-7-fluoro-2-oxo-2,3-dihydro-indol-1-ylmethyl}-benzoic acid

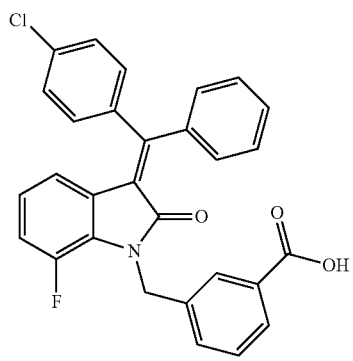 [SMILES: O=C(O)c1cccc(CN2C(=O)/C(=C(\c3ccccc3)c3ccc(Cl)cc3)c3cccc(F)c32)c1]

The title compound was prepared in analogy to Example 44 starting from 3-{3-[1-(4-chloro-phenyl)-1-phenyl-meth-(E)-ylidene]-7-fluoro-2-oxo-2,3-dihydro-indol-1-ylmethyl}-benzoic acid methyl ester. $^1$H NMR (300 Hz, CDCl$_3$): δppm 5.13 (s, 2H), 6.32 (d, 1H), 6.63-6.67 (m, 1H), 6.82-6.89 (dd, 1H), 7.26-7.43 (m, 10H), 7.59 (d, 1H), 7.99 (d, 1H), 8.08 (s, 1H).

Example 74

3-{5-Chloro-3-[1-(4-chloro-phenyl)-1-phenyl-meth-(E)-ylidene]-2-oxo-2,3-dihydro-indol-1-ylmethyl}-benzoic acid

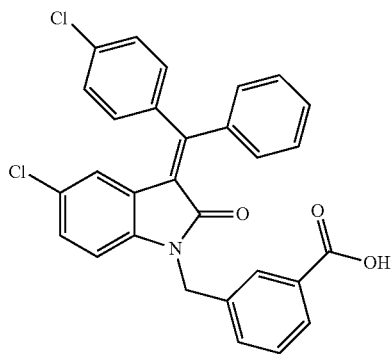 [SMILES: O=C(O)c1cccc(CN2C(=O)/C(=C(\c3ccccc3)c3ccc(Cl)cc3)c3cc(Cl)ccc32)c1]

The title compound was prepared in analogy to Example 44 starting from 3-{5-chloro-3-[1-(4-chloro-phenyl)-1-phenyl-meth-(E)-ylidene]-2-oxo-2,3-dihydro-indol-1-ylmethyl}-benzoic acid methyl ester. $^1$H NMR (300 Hz, CDCl$_3$): δppm 4.97 (s, 2H), 6.58 (m, 2H), 7.05 (dd, 1H), 7.20 (m, 1H), 7.27-7.46 (m, 9H), 7.52 (d, 1H), 8.01 (d, 1H), 8.04 (s, 1H).

Example 75

3-{3-[1-(2-Chloro-phenyl)-1-phenyl-meth-(E)-ylidene]-2-oxo-2,3-dihydro-indol-1-ylmethyl}-benzoic acid

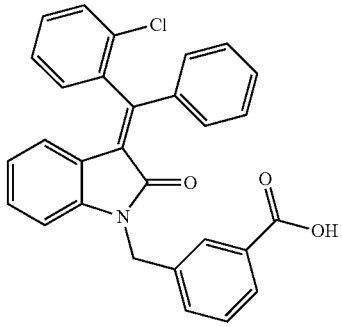 [SMILES: O=C(O)c1cccc(CN2C(=O)/C(=C(\c3ccccc3)c3ccccc3Cl)c3ccccc32)c1]

The title compound was prepared in analogy to Example 44 starting from 3-{3-[1-(2-chloro-phenyl)-1-phenyl-meth-(E)-ylidene]-2-oxo-2,3-dihydro-indol-1-ylmethyl}-benzoic acid methyl ester. $^1$H NMR (CDCl$_3$, 300 MHz) δppm 8.06 (s, 1H), 7.99 (d, 1H), 7.50-7.57 (m, 3H), 7.37-7.44 (m, 7H), 7.07 (t, 1H), 6.63-6.70 (m, 2H), 6.05 (d, 1H), 4.97 (dd, 2H).

Example 76

2-{3-[1-(4-Chloro-phenyl)-1-phenyl-meth-(E)-ylidene]-2-oxo-2,3-dihydro-indol-1-ylmethyl}-thiazole-4-carboxylic acid

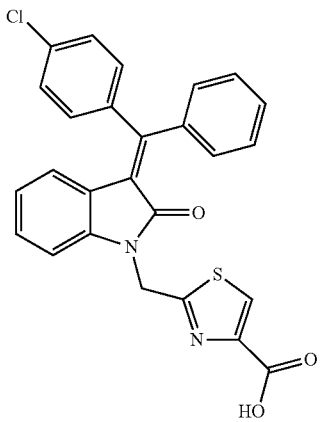 [SMILES: O=C(O)c1csc(CN2C(=O)/C(=C(\c3ccccc3)c3ccc(Cl)cc3)c3ccccc32)n1]

The title compound was prepared in analogy to Example 44 starting from 2-{3-[1-(4-chloro-phenyl)-1-phenyl-meth-(E)-ylidene]-2-oxo-2,3-dihydro-indol-1-ylmethyl}-thiazole-4-carboxylic acid methyl ester. $^1$H NMR (300 Hz, CDCl$_3$): δppm 5.27 (s, 2H), 6.59 (d, 1H), 6.78 (t, 1H), 6.87 (d, 1H), 7.15 (t, 1H), 7.31-7.43 (m, 9H), 8.22 (s, 1H).

Example 77

3-[3-(4-Methyl-1-phenyl-pent-(Z)-ylidene)-2-oxo-2,3-dihydro-indol-1-ylmethyl]-benzoic acid methyl ester

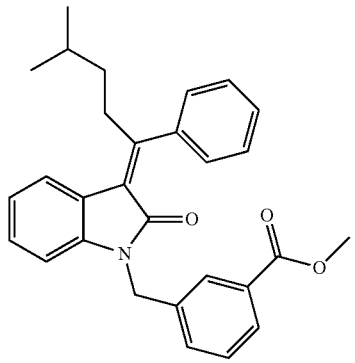 [SMILES: COC(=O)c1cccc(CN2C(=O)/C(=C(/CCC(C)C)c3ccccc3)c3ccccc32)c1]

To a degassed refluxing solution of 3-{[(2-iodo-phenyl)-(3-phenyl-propynoyl)-amino]-methyl}-benzoic acid methyl ester (100 mg, 0.2 mmol) and Ni(PPh$_3$)$_2$I$_2$ (16 mg, 0.02 mmol) in CH$_2$Cl$_2$ (8 ml) was added 3-methylbutylzinc bromide (151 mg, 0.7 mmol) in CH$_2$Cl$_2$ (1 ml). The reaction was stirred at 40° C. for 6 h and then the solution was cooled to room temperature. The resultant solution was diluted with ethyl acetate (50 ml). The organic layer was washed with aqueous HCl solution (4%, 10 ml), brine (3×10 ml). The aqueous layer was back-extracted with ethyl acetate (3×10 ml). The combined organic layer was dried over anhydrous sodium sulfate. After filtration, the solvent was removed under reduced pressure and the residue was purified by column chromatography on silica gel, eluting with petrol ether-ethyl acetate, to give 3-{3-[4-methyl-1-phenyl-pent-(Z)-ylidene]-2-oxo-2,3-dihydro-indol-1-ylmethyl}-benzoic acid methyl ester (24 mg, 28%) as light yellow solid. $^1$H NMR (300 Hz, CDCl$_3$): δppm 0.88 (d, 6H), 1.43-1.55 (m, 2H), 1.68-1.72 (m, 1H), 2.93-2.99 (m, 2H), 3.91 (s, 3H), 4.89 (s, 2H), 6.64 (d, 1H), 7.05 (t, 1H), 7.15 (t, 1H), 7.28-7.38 (m, 4H), 7.40-7.47 (m, 3H), 7.62 (d, 1H), 7.91 (d, 1H), 7.95 (s, 1H); and 3-{3-[4-methyl-1-phenyl-pent-(E)-ylidene]-2-oxo-2,3-dihydro-indol-1-ylmethyl}-benzoic acid methyl ester (29 mg, 33%) as light yellow solid. $^1$H NMR (300 Hz, CDCl$_3$): δ ppm 0.88 (d, 6H), 1.36-1.44 (m, 2H), 1.64-1.68 (m, 1H), 3.33-3.38 (m, 2H), 3.91 (s, 3H), 5.04 (s, 2H), 6.01 (d, 1H), 6.58-6.61 (m, 2H), 6.96-7.02 (t, 1H), 7.26-7.29 (m, 2H), 7.37 (t, 2H), 7.43-7.52 (m, 3H), 7.93 (d, 1H), 8.03 (s, 1H).

Example 78

3-{3-[3,3-Dimethyl-1-phenyl-but-(Z)-ylidene]-2-oxo-2,3-dihydro-indol-1-ylmethyl}-benzoic acid methyl ester

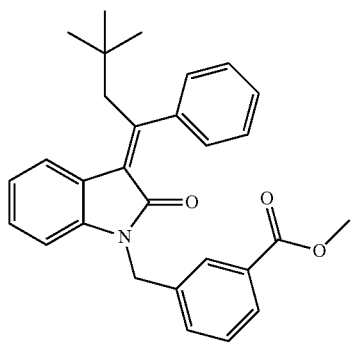 [SMILES: COC(=O)c1cccc(CN2C(=O)/C(=C(/CC(C)(C)C)c3ccccc3)c3ccccc32)c1]

The title compound was prepared in analogy to Example 77 starting from tert-butylzinc bromide (commercially available) and 3-{[(2-iodo-phenyl)-(3-phenyl-propynoyl)-amino]-methyl}-benzoic acid methyl ester. $^1$H NMR (300 Hz, CDCl$_3$): δppm 0.80 (s, 9H), 2.74 (s, 2H), 3.90 (s, 3H), 5.67 (s, 2H), 6.98 (t, 1H), 7.12-7.52 (m, 10H), 7.93 (d, 1H), 8.03 (s, 1H).

Example 79

3-{3-[2-(4-Chloro-phenyl)-1-phenyl-eth-(Z)-ylidene]-2-oxo-2,3-dihydro-indol-1-ylmethyl}-benzoic acid methyl ester

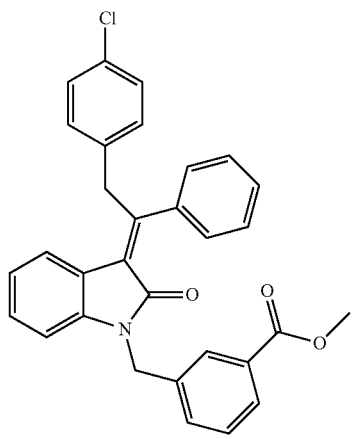 [SMILES: COC(=O)c1cccc(CN2C(=O)/C(=C(/Cc3ccc(Cl)cc3)c3ccccc3)c3ccccc32)c1]

The title compound was prepared in analogy to Example 77 starting from 4-chloro-benzylzinc bromide (commercially available) and 3-{[(2-iodo-phenyl)-(3-phenyl-propynoyl)-amino]-methyl}-benzoic acid methyl ester. $^1$H NMR (300 Hz, CDCl$_3$): δppm 3.92 (s, 3H), 4.73 (s, 2H), 5.07 (s, 2H), 5.99 (d, 1H), 6.58-6.65 (m, 2H), 7.08-7.20 (m, 7H), 7.37-7.43 (m, 4H), 7.52 (d, 1H), 7.93 (d, 1H), 8.06 (s, 1H).

Example 80

3-{3-[3,3-Dimethyl-1-phenyl-but-(E)-ylidene]-2-oxo-2,3-dihydro-indol-1-ylmethyl}-benzoic acid methyl ester

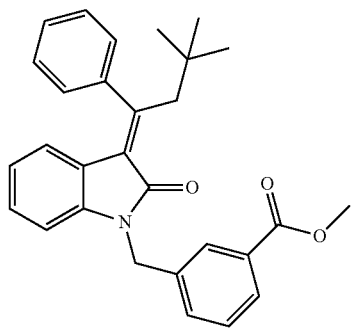 [SMILES: COC(=O)c1cccc(CN2C(=O)/C(=C(\CC(C)(C)C)c3ccccc3)c3ccccc32)c1]

The title compound was prepared in analogy to Example 77 starting from tert-butylzinc bromide (commercially available) and 3-{[(2-iodo-phenyl)-(3-phenyl-propynoyl)-amino]-methyl}-benzoic acid methyl ester. $^1$H NMR (300 Hz, CDCl$_3$): δppm 0.91 (s, 9H), 3.48 (s, 2H), 3.90 (s, 3H), 5.03 (s, 2H), 6.22 (d, 1H), 6.56-6.62 (m, 2H), 6.98 (t, 1H), 7.36-7.50 (m, 7H), 7.92 (d, 1H), 8.02 (s, 1H).

Example 81

3-[3-(4-Methyl-1-phenyl-pent-(Z)-ylidene)-2-oxo-2,3-dihydro-indol-1-ylmethyl]-benzoic acid

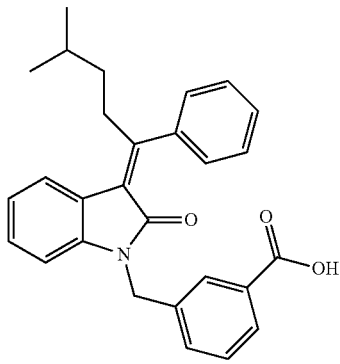 [SMILES: CC(C)CC/C(=C1/C(=O)N(Cc2cccc(C(=O)O)c2)c2ccccc21)c1ccccc1]

3-{3-[4-Methyl-1-phenyl-pent-(Z)-ylidene]-2-oxo-2,3-dihydro-indol-1-ylmethyl}-benzoic acid methyl ester (24 mg, 0.05 mmol) was dissolved in THF (1 ml) and water (1 ml) and LiOH.H$_2$O (14 mg, 0.33 mmol) was added in one portion. The mixture was stirred at 50° C. for 16 h. The mixture was concentrated under reduced pressure and acidified to pH=3. Purification by preparative HPLC afforded 3-[3-(4-methyl-1-phenyl-pent-(Z)-ylidene)-2-oxo-2,3-dihydro-indol-1-ylmethyl]-benzoic acid 10 mg. $^1$H NMR (300 Hz, CDCl$_3$): δ ppm 0.88 (d, 6H), 1.36-1.44 (m, 2H), 1.64-1.68 (m, 1H), 3.33-3.38 (m, 2H), 5.04 (s, 2H), 6.01 (d, 1H), 6.58-6.61 (m, 2H), 6.96-7.02 (t, 1H), 7.26-7.29 (m, 2H), 7.37 (t, 2H), 7.43-7.52 (m, 3H), 7.93 (d, 1H), 8.03 (s, 1H).

Example 82

3-{3-[1-(4-Chloro-benzyl)-2-methyl-prop-(Z)-ylidene]-2-oxo-2,3-dihydro-indol-1-ylmethyl}-benzoic acid

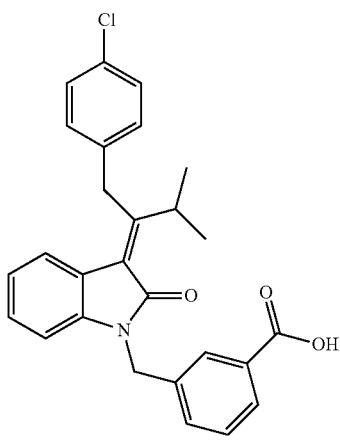 [SMILES: CC(C)/C(Cc1ccc(Cl)cc1)=C1\C(=O)N(Cc2cccc(C(=O)O)c2)c2ccccc21]

The title compound was prepared in analogy to Example 81 starting from 3-{3-[1-(4-chloro-benzyl)-2-methyl-prop-(Z)-ylidene]-2-oxo-2,3-dihydro-indol-1-ylmethyl}-benzoic acid methyl ester. $^1$H NMR (300 Hz, CDCl$_3$): δppm 1.14 (d, 6H), 3.62-3.71 (m, 1H), 4.577 (s, 2H), 5.018 (s, 2H), 6.82 (d, 1H), 7.04 (t, 1H), 7.21-7.26 (m, 5H), 7.43 (t, 1H), 7.53 (d, 1H), 7.63 (d, 1H), 8.01 (d, 1H), 8.07 (s, 1H).

Example 83

3-{3-[1-(4-Fluoro-phenyl)-ethylidene]-2-oxo-2,3-dihydro-indol-1-ylmethyl}-benzoic acid

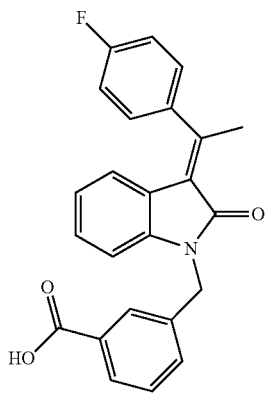 [SMILES: C/C(=C1\C(=O)N(Cc2cccc(C(=O)O)c2)c2ccccc21)c1ccc(F)cc1]

But-2-ynoic acid (2-iodo-phenyl)-amide

A mixture of 2-iodo-phenylamine (10 g, 45.7 mmol) and but-2-ynoic acid (4.6 g, 54.8 mmol) in dichloromethane (50 ml) was cooled to 0° C. Then 1,3-dicyclohexylcarbodiimide (14 g, 68.6 mmol) was added. After stirring for 3 hours at room temperature, the mixture was washed with water (20 ml). The organic layer was dried over sodium sulfate and concentrated to give the crude product but-2-ynoic acid (2-iodo-phenyl)-amide (13.0 g, 100%) as a yellow solid which was used in next step without purification. MS calcd. for C$_{10}$H$_8$INO 285.1, obsd. (ESI$^+$) [(M+H)$^+$] 286.0.

3-{[(2-Iodo-phenyl)-(1-oxo-but-2-ynyl)-amino]-methyl}-benzoic acid methyl ester A mixture of but-2-ynoic acid (2-iodo-phenyl)-amide (2.85 g, 10 mmol) and cesium carbonate (4.89 g, 15 mmol) in DMF (20 ml) was stirred for 10 minutes. 3-bromomethyl-benzoic acid methyl ester (2.52 g, 11 mmol) was added. Then the mixture was stirred for 12 hours at room temperature. After removal of solids, the filtrate was treated with water and extracted with ether. The organic layer was dried over sodium sulfate and concentrated to give the residue which was purified by flash chromatography, eluting with ethyl acetate/hexane=1:4 to afford the product 3-{[(2-iodo-phenyl)-(1-oxo-but-2-ynyl)-amino]-methyl}-benzoic acid methyl ester as yellow solid (3.03, 70%). MS calcd. for C$_{19}$H$_{16}$INO$_3$ 433.3, obsd. (ESI$^+$) [(M+H)$^+$] 434.1.

3-{3-[1-(4-Fluoro-phenyl)-ethylidene]-2-oxo-2,3-dihydro-indol-1-ylmethyl}-benzoic acid methyl ester A mixture of 3-{[(2-iodo-phenyl)-(1-oxo-but-2-ynyl)-amino]-methyl}-benzoic acid methyl ester (0.5 g, 1.15 mmol), 4-fluorophenylboronic acid (0.32 g, 2.3 mmol), tetrakis(triphenylphosphine) palladium (0.13 g, 0.115 mmol) and copper thiophene-2-carboxylic acid (0.46 g, 2.42 mmol) in THF was stirred for 5 hours at 60° C. After removal of solvent, the residue was purified by flash chromatography, eluting with ethyl acetate/hexane=1:5 to afford the product 3-{3-[1-(4-fluoro-phenyl)-ethylidene]-2-oxo-2,3-dihydro-indol-1-ylmethyl}-benzoic acid methyl ester (0.28 g, 60%) as a yellow solid. MS calcd. for $C_{25}H_{20}FNO_3$ 401.4, obsd. $(ESI^+)$ $[(M+H)^+]$ 402.2.

3-{3-[1-(4-Fluoro-phenyl)-ethylidene]-2-oxo-2,3-dihydro-indol-1-ylmethyl}-benzoic acid A solution of 3-{3-[1-(4-fluoro-phenyl)-ethylidene]-2-oxo-2,3-dihydro-indol-1-ylmethyl}-benzoic acid methyl ester (0.33 g, 0.82 mmol) was dissolved in THF 5 ml. Then a solution of lithium hydroxide (0.35 g, 8.2 mmol) in water (2.0 ml) was added. After stirring for 12 hours, the solvent was removed under reduced pressure. The residue was dissolved in 2 ml DMF for prepared HPLC to give 3-{3-[1-(4-fluoro-phenyl)-ethylidene]-2-oxo-2,3-dihydro-indol-1-ylmethyl}-benzoic acid as yellow powder (100 mg). $^1$H NMR (400 MHz, DMSO-$d_6$) δ ppm 2.78 (s, 3H) 5.06 (s, 2H) 6.08 (d, J=7.83 Hz, 1H) 6.68 (t, J=7.45 Hz, 1H) 6.92 (d, J=7.83 Hz, 1H) 7.11 (t, J=7.45 Hz, 1H) 7.38 (t, J=8.84 Hz, 2H) 7.43-7.51 (m, 1H) 7.46 (dd, J=8.72, 5.68 Hz, 2H) 7.60 (d, J=7.58 Hz, 1H) 7.85 (d, J=7.83 Hz, 1H) 7.92 (s, 1H) 13.03 (s, 1H). MS calcd. for $C_{24}H_{18}FNO_3$ 387.4, obsd. $(ESI^+)$ $[(M+H)^+]$ 388.2.

Example 84

3-{3-[1-(4-Chloro-phenyl)-2-methyl-propylidene]-2-oxo-2,3-dihydro-indol-1-ylmethyl}-benzoic acid methyl ester

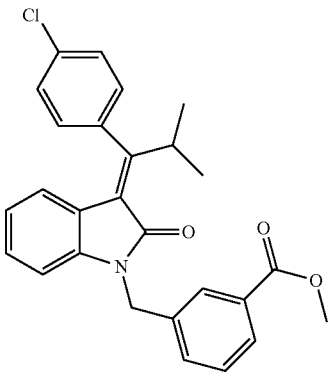 [SMILES: COC(=O)c1cccc(CN2C(=O)/C(=C(/c3ccc(Cl)cc3)C(C)C)c3ccccc32)c1]

1-Iodo-2-isocyanato-benzene

A solution of 2-iodo-phenylamine (30 g, 0.14 mol) in dichloromethane (800 ml) was added triphosgene (14.6 g, 49.3 mmol) and saturated sodium bicarbonate (544 ml) at 0° C. The resulted mixture was stirred for 4 hours. The organic layer was washed with brine (200 ml) and dried over sodium sulfate. After removal of solvent, the crude product 1-iodo-2-isocyanato-benzene (32.3 g, 96%) was obtained as a yellow oil which was used in next step without purification.

4-Methyl-pent-2-ynoic acid (2-iodo-phenyl)-amide

3-Methyl-but-1-yne (11 g, 0.16 mol) in THF (100 ml) was added n-BuLi (2.5M in hexane) (59 ml, 0.15 mol) at 0° C. The resulting mixture was stirred for 30 minutes. Then a solution of 1-iodo-2-isocyanato-benzene (33 g, 0.14 mol) in THF (100 ml) was dropped into the mixture. After stirring for 2 hours at 0° C., the mixture was treated with brine (100 ml) and extracted with ether (200 ml). The organic layer was dried over sodium sulfate and concentrated to give the crude product 4-methyl-pent-2-ynoic acid (2-iodo-phenyl)-amide (38 g, 90%) as a yellow oil which was used in next step without purification. MS calcd. for $C_{12}H_{12}INO$ 313.1, obsd. $(ESI^+)$ $[(M+H)^+]$ 314.0.

3-{[(2-Iodo-phenyl)-(4-methyl-pent-2-ynoyl)-amino]-methyl}-benzoic acid methyl ester A mixture of 4-methyl-pent-2-ynoic acid (2-iodo-phenyl)-amide (21 g, 67.1 mmol) and cesium carbonate (33.0 g, 100.7 mmol) in DMF (170 ml) was stirred for 10 minutes. 3-bromomethyl-benzoic acid methyl ester (16.9 g, 73.8 mmol) was added. Then the mixture was stirred for 12 hours at room temperature. After removal of the solids, the filtrate was treated with water and extracted with ether. The organic layer was dried over sodium sulfate and concentrated to give the residue which was purified by flash chromatography, eluting with ethyl acetate/hexane=1:4 to afford the product 3-{[(2-iodo-phenyl)-(4-methyl-pent-2-ynoyl)-amino]-methyl}-benzoic acid methyl ester as yellow solid (15.9 g, 51%). MS calcd. for $C_{21}H_{20}ClNO_3$ 461.3, obsd. $(ESI^+)$ $[(M+H)^+]$ 461.9.

3-{3-[1-(4-Chloro-phenyl)-2-methyl-propylidene]-2-oxo-2,3-dihydro-indol-1-ylmethyl}-benzoic acid methyl ester A mixture of 3-{[(2-iodo-phenyl)-(4-methyl-pent-2-ynoyl)-amino]-methyl}-benzoic acid methyl ester (0.93 g, 2.02 mmol), 4-chlorophenylboronic acid (0.63 g, 4.04 mmol), triphenylphosphine (53 mg, 0.202 mmol), palladium acetate (23 mg, 0.10 mmol) and cesium fluoride (0.92 g, 6.06 mmol) in THF (15 ml) was stirred for 3 hours at 60° C. After removal of solvent, the residue was purified by flash chromatography, eluting with ethyl acetate/hexane=1:5 to afford the product 3-{3-[1-(4-chloro-phenyl)-2-methyl-propylidene]-2-oxo-2,3-dihydro-indol-1-ylmethyl}-benzoic acid methyl ester (0.40 g, 44%) as a yellow solid. MS calcd. for $C_{27}H_{24}ClNO_3$ 445.5, obsd. $(ESI^+)$ $[(M+H)^+]$ 446.0. $^1$H NMR (400 MHz, DMSO-$d_6$) δ ppm 1.10 (d, J=6.82 Hz, 6H) 3.91 (s, 3H) 4.99 (dt, J=13.71, 6.92 Hz, 1H) 5.06 (s, 2H) 5.73 (d, J=7.58 Hz, 1H) 6.62 (t, J=7.71 Hz, 1H) 6.73 (d, J=7.83 Hz, 1H) 7.05 (t, J=7.71 Hz, 1H) 7.19 (d, J=8.34 Hz, 2H) 7.46 (t, J=7.83 Hz, 1H) 7.55 (d, J=8.08 Hz, 3H) 7.94 (d, J=7.58 Hz, 1H) 8.02 (s, 1H) MS calcd. for $C_{27}H_{24}ClNO_3$ 445.5, obsd. $(ESI^+)$ $[(M+H)^+]$ 446.0.

Example 85

3-{3-[2-Methyl-1-phenyl-prop-(E)-ylidene]-2-oxo-2,3-dihydro-indol-1-ylmethyl}-benzoic acid methyl ester

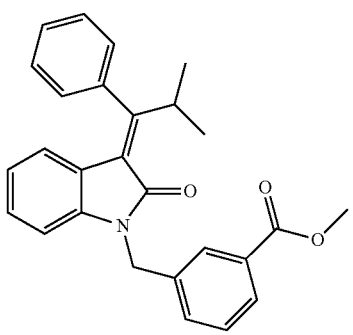 [SMILES: COC(=O)c1cccc(CN2C(=O)/C(=C(/c3ccccc3)C(C)C)c3ccccc32)c1]

The title compound was prepared in analogy to Example 84 starting from phenylboronic acid (commercially available) and 3-{[(2-iodo phenyl)-(4-methyl-pent-2-ynoyl)-amino]-methyl}-benzoic acid methyl ester. $^1$H NMR (CDCl$_3$, 300 MHz) δppm 8.04 (s, 1H), 7.94 (d, 1H), 7.48-7.53 (m, 3H), 7.39 (t, 1H), 7.15 (dd, 2H), 6.99 (t, 1H), 6.59-6.61 (d, 1H), 6.55 (t, 1H), 5.59 (d, 2H), 5.00-5.05 (m, 3H), 3.97 (s, 3H), 1.11 (s, 3H), 1.09 (s, 3H).

Example 86

3-{3-[1-(4-Acetyl-phenyl)-2-methyl-prop-(E)-ylidene]-2-oxo-2,3-dihydro-indol-1-ylmethyl}-benzoic acid methyl ester

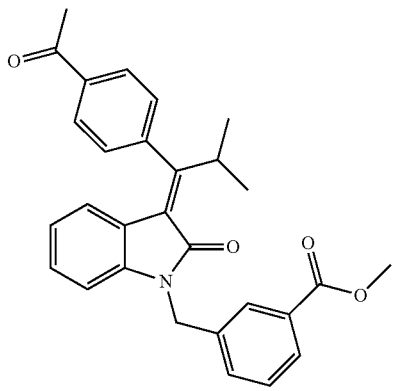 [SMILES: COC(=O)c1cccc(CN2C(=O)/C(=C(/c3ccc(C(C)=O)cc3)C(C)C)c3ccccc32)c1]

The title compound was prepared in analogy to Example 84 starting from 4-acetyl-phenylboronic acid (commercially available) and 3-{[(2-iodo phenyl)-(4-methyl-pent-2-ynoyl)-amino]-methyl}-benzoic acid methyl ester. $^1$H NMR (CDCl$_3$, 300 MHz) δppm 8.03-8.11 (m, 4H), 7.94 (d, 1H), 7.71 (d, 1H), 7.52 (d, 1H), 7.40 (t, 1H), 7.29 (d, 2H), 7.00 (t, 1H), 6.61 (d, 1H), 6.54 (t, 1H), 5.61 (d, H), 5.02-5.07 (m, 3H), 3.90 (s, 3H), 2.70 (s, 3H), 1.19 (d, 3H), 1.17 (d, 3H).

Example 87

3-{3-[1-(4-Chloro-phenyl)-1-cyclohexyl-meth-(E)-ylidene]-2-oxo-2,3-dihydro-indol-1-ylmethyl}-benzoic acid methyl ester

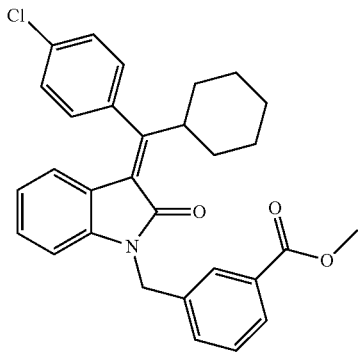 [SMILES: COC(=O)c1cccc(CN2C(=O)/C(=C(/c3ccc(Cl)cc3)C3CCCCC3)c3ccccc32)c1]

The title compound was prepared in analogy to Example 84 starting from 4-chlorophenylboronic acid (commercially available) and 3-{[(3-cyclohexyl-propynoyl)-(2-iodo-phenyl)-amino]-methyl}-benzoic acid methyl ester. $^1$H NMR (CDCl$_3$, 300 MHz) δppm 8.02 (s, 1H), 7.93 (d, 1H), 7.47-7.51 (m, 13H), 7.39 (t, 1H), 7.10 (d, 2H), 7.01 (t, 1H), 6.59-6.63 (m, 2H), 5.71 (d, 2H), 5.02 (s, 2H), 4.62 (t, 1H), 3.91 (s, 3H), 1.44-1.76 (m, 6H), 1.01-1.18 (m, 4H).

Example 88

3-{3-[2-Methyl-1-(4-trifluoromethyl-phenyl)-prop-(E)-ylidene]-2-oxo-2,3-dihydro-indol-1-ylmethyl}-benzoic acid methyl ester

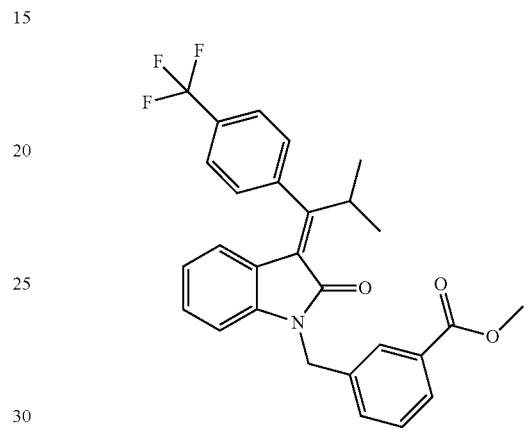

The title compound was prepared in analogy to Example 84 starting from 4-trifluoromethyl-phenylboronic acid (commercially available) and 3-{[(2-iodo phenyl)-(4-methyl-pent-2-ynoyl)-amino]-methyl}-benzoic acid methyl ester. $^1$H NMR (DMSO, 300 MHz) δppm 7.90 (s, 1H), 7.79-7.86 (m, 2H), 7.58 (d, 1H), 7.48 (t, 1H), 7.42 (d, 1H), 7.09 (t, 1H), 7.00 (d, 1H), 6.89 (d, 1H), 6.65 (t, 1H), 5.65 (d, 1H), 5.03 (s, 2H), 4.84-4.93 (m, 1H), 3.57 (s, 3H), 0.96-1.06 (dd, 6H).

Example 89

3-{3-[1-(4-Chloro-phenyl)-2-hydroxy-2-methyl-prop-(Z)-ylidene]-2-oxo-2,3-dihydro-indol-1-ylmethyl}-benzoic acid methyl ester

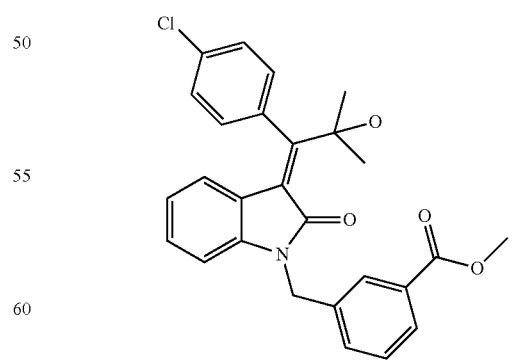

The title compound was prepared in analogy to Example 84 starting from 4-chlorophenylboronic acid (commercially available) and 3-{[(4-hydroxy-4-methyl-pent-2-ynoyl)-(2-iodo-phenyl)-amino]-methyl}-benzoic acid methyl ester. $^1$H NMR (400 MHz, DMSO-d$_6$) δppm 1.30 (s, 6H) 3.83 (s, 3H) 5.14 (s, 2H) 5.43 (d, J=7.58 Hz, 1H) 6.68 (t, J=7.58 Hz, 1H) 7.01 (d, J=7.83 Hz, 1H) 7.12 (t, J=7.45 Hz, 1H) 7.27 (d, J=8.34 Hz, 2H) 7.51 (t, J=7.71 Hz, 1H) 7.58-7.65 (m, 4H) 7.87 (d, J=7.58 Hz, 1H) 7.97 (s, 1H).

Example 90

3-{3-[1-(4-Cyano-phenyl)-2-hydroxy-2-methyl-prop-(Z)-ylidene]-2-oxo-2,3-dihydro-indol-1-ylmethyl}-benzoic acid methyl ester

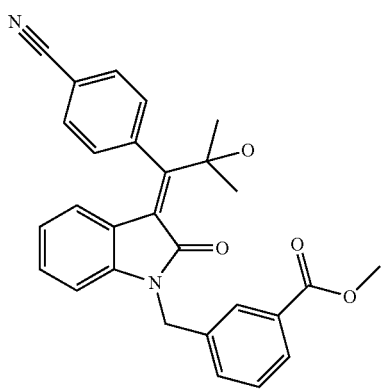

The title compound was prepared in analogy to Example 84 starting from 4-cyano-phenylboronic acid (commercially available) and 3-{[(4-hydroxy-4-methyl-pent-2-ynoyl)-(2-iodo-phenyl)-amino]-methyl}-benzoic acid methyl ester. $^1$H NMR (400 MHz, DMSO-d$_6$) δppm 1.33 (s, 6H) 3.85 (s, 3H) 5.15 (s, 2H) 5.35 (d, J=7.83 Hz, 1H) 6.68 (t, J=7.71 Hz, 1H) 7.03 (d, J=7.83 Hz, 1H) 7.15 (t, J=7.71 Hz, 1H) 7.48-7.55 (m, 1H) 7.52 (d, J=7.58 Hz, 3H) 7.62 (d, J=7.83 Hz, 1H) 7.89 (d, J=7.83 Hz, 1H) 7.99 (s, 1H) 8.05 (d, J=8.34 Hz, 2H).

Example 91

3-{3-[1-(4-Chloro-phenyl)-2,2-dimethyl-prop-(Z)-ylidene]-2-oxo-2,3-dihydro-indol-1-ylmethyl}-benzoic acid methyl ester

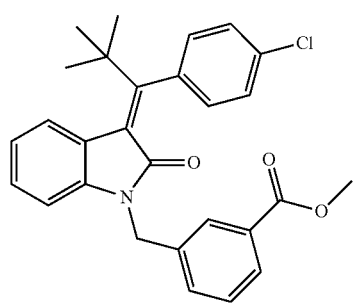 [SMILES: COC(=O)c1cccc(CN2C(=O)/C(=C(\c3ccc(Cl)cc3)C(C)(C)C)c3ccccc32)c1]

The title compound was prepared in analogy to Example 84 starting from 4-chlorophenylboronic acid (commercially available) and 3-{[(4,4-dimethyl-pent-2-ynoyl)-(2-iodo-phenyl)-amino]-methyl}-benzoic acid methyl ester. $^1$H NMR (400 MHz, MeOD) δppm 1.38 (s, 9H) 3.86 (s, 3H) 4.83 (d, 2H) 6.81 (d, J=7.83 Hz, 1H) 6.99 (d, J=7.83 Hz, 2H) 7.10 (t, J=7.58 Hz, 1H) 7.22 (t, J=7.71 Hz, 1H) 7.33-7.42 (m, 4H) 7.84-7.88 (m, 2H) 7.93 (d, J=7.83 Hz, 1H).

Example 92

3-{3-[1-(4-Cyano-phenyl)-2,2-dimethyl-prop-(E)-ylidene]-2-oxo-2,3-dihydro-indol-1-ylmethyl}-benzoic acid methyl ester

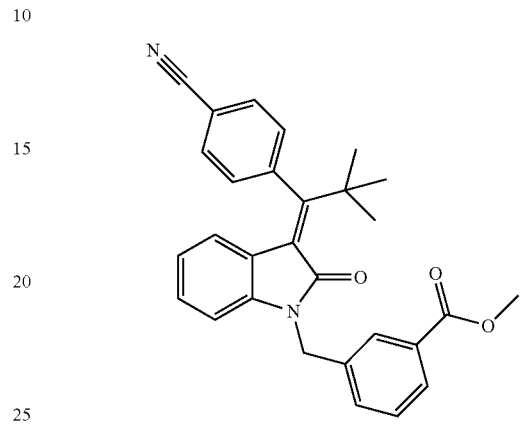

The title compound was prepared in analogy to Example 84 starting from 4-cyano-phenylboronic acid (commercially available) and 3-{[(4,4-dimethyl-pent-2-ynoyl)-(2-iodo-phenyl)-amino]-methyl}-benzoic acid methyl ester. $^1$H NMR (400 MHz, DMSO-d$_6$) δppm 1.35 (s, 9H) 3.84 (s, 3H) 5.07 (s, 2H) 5.19 (d, J=7.83 Hz, 1H) 6.56 (t, J=7.71 Hz, 1H) 6.88 (d, J=7.83 Hz, 1H) 7.06 (t, J=7.71 Hz, 1H) 7.42 (d, J=8.08 Hz, 2H) 7.50 (t, J=7.71 Hz, 1H) 7.59 (d, J=7.58 Hz, 1H) 7.87 (d, J=7.58 Hz, 1H) 7.95-8.05 (m, 3H).

Example 93

3-{3-[1-(4-Chloro-phenyl)-2,2-dimethyl-prop-(E)-ylidene]-2-oxo-2,3-dihydro-indol-1-ylmethyl}-benzoic acid methyl ester

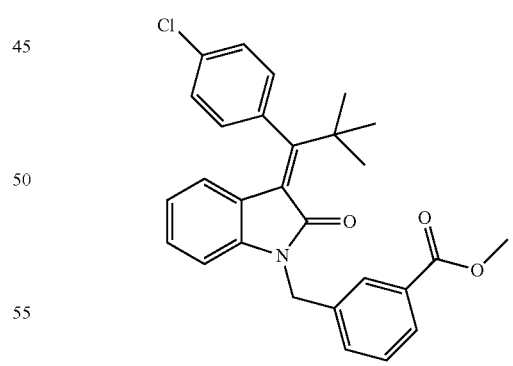

The title compound was prepared in analogy to Example 84 starting from 4-chlorophenylboronic acid (commercially available) and 3-{[(4,4-dimethyl-pent-2-ynoyl)-(2-iodo-phenyl)-amino]-methyl}-benzoic acid methyl ester. $^1$H NMR (400 MHz, DMSO-d$_6$) δppm 1.36 (s, 9H) 3.84 (s, 3H) 5.07 (s, 2H) 5.30 (d, J=7.83 Hz, 1H) 6.57 (t, J=7.83 Hz, 1H) 6.88 (d, J=7.83 Hz, 1H) 7.05 (t, J=7.71 Hz, 1H) 7.21 (d, J=8.08 Hz, 2H) 7.51 (t, J=7.71 Hz, 1H) 7.57-7.64 (m, 2H) 7.87 (d, J=7.58 Hz, 1H) 7.97 (s, 1H).

Example 94

3-{3-[1-(4-chloro-phenyl)-2-methyl-propylidene]-2-oxo-2,3-dihydro-indol-1-ylmethyl}-benzoic acid

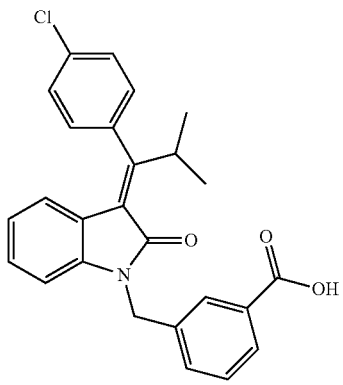 [SMILES: CC(C)/C(=C1\C(=O)N(Cc2cccc(C(=O)O)c2)c2ccccc21)c1ccc(Cl)cc1]

A solution of 3-{3-[1-(4-chloro-phenyl)-2-methyl-propylidene]-2-oxo-2,3-dihydro-indol-1-ylmethyl}-benzoic acid methyl ester (0.40 g, 0.90 mmol) was dissolved in THF 15 ml. Then a solution of lithium hydroxide (0.38 g, 9.0 mmol) in water (3.0 ml) was added. After stirring for 12 hours, the solvent was removed under reduced pressure. The residue was dissolved in 2 ml DMF for prepared HPLC to give 3-{3-[1-(4-chloro-phenyl)-2-methyl-propylidene]-2-oxo-2,3-dihydro-indol-1-ylmethyl}-benzoic acid as a yellow powder (200 mg). $^1$H NMR (400 MHz, DMSO-$d_6$) δ ppm 1.00 (d, J=6.82 Hz, 6H) 4.90-4.99 (m, 1H) 5.05 (s, 2H) 5.59 (d, J=7.83 Hz, 1H) 6.64 (t, J=7.71 Hz, 1H) 6.91 (d, J=7.83 Hz, 1H) 7.10 (t, J=7.71 Hz, 1H) 7.27 (d, J=8.34 Hz, 2H) 7.49 (t, J=7.58 Hz, 1H) 7.63 (d, J=8.34 Hz, 2H) 7.59 (d, J=7.58 Hz, 1H) 7.85 (d, J=7.58 Hz, 1H) 7.92 (s, 1H) 13.05 (s, 1H). MS calcd. for $C_{26}H_{22}ClNO_3$ 431.5, obsd. (ESI$^+$) [(M+H)$^+$] 432.0.

Example 95

3-{3-[1-(4-Cyano-phenyl)-2-methyl-prop-(E)-ylidene]-2-oxo-2,3-dihydro-indol-1-ylmethyl}-benzoic acid

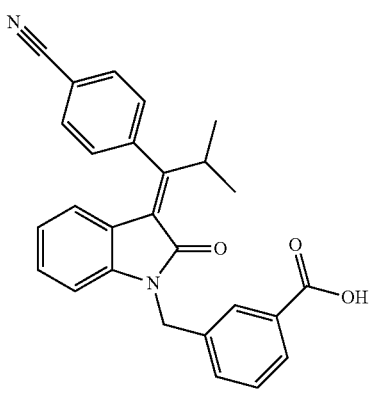

The title compound was prepared in analogy to Example 94 starting from 3-{3-[1-(4-cyano-phenyl)-2-methyl-prop-(E)-ylidene]-2-oxo-2,3-dihydroindol-1-ylmethyl}benzoic acid methyl ester. $^1$H NMR (400 MHz, DMSO-$d_6$) δppm 1.01 (d, J=6.82 Hz, 6H) 4.91-5.00 (m, 1H) 5.05 (s, 2H) 5.50 (d, J=7.83 Hz, 1H) 6.64 (t, J=7.58 Hz, 1H) 6.93 (d, J=7.83 Hz, 1H) 7.11 (t, J=7.58 Hz, 1H) 7.48 (d, J=7.58 Hz, 3H) 7.60 (d, J=7.58 Hz, 1H) 7.85 (d, J=7.33 Hz, 1H) 7.93 (s, 1H) 8.05 (d, J=8.08 Hz, 2H) 13.06 (br.s., 1H).

Example 96

6-{3-[1-(4-Chloro-phenyl)-2-methyl-prop-(E)-ylidene]-2-oxo-2,3-dihydro-indol-1-ylmethyl}-pyridine-2-carboxylic acid

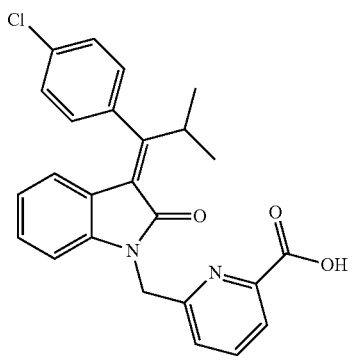 [SMILES: CC(C)/C(=C1\C(=O)N(Cc2cccc(C(=O)O)n2)c2ccccc21)c1ccc(Cl)cc1]

The title compound was prepared in analogy to Example 94 starting from 6-{3-[1-(4-chloro-phenyl)-2-methyl-prop-(E)-ylidene]-2-oxo-2,3-dihydro-indol-1 ylmethyl}-pyridine-2-carboxylic acid methyl ester. $^1$H NMR (400 MHz, MeOD) δppm 1.06 (d, 6H) 4.92-5.01 (m, 1H) 5.23 (s, 2H) 5.74 (d, 1H) 6.64 (t, 1H) 6.87 (d, 1H) 7.08 (t, 1H) 7.22 (d, 2H) 7.45 (d, 1H) 7.59 (d, 2H) 7.95 (t, 1H) 8.09 (d, 1H).

Example 97

6-{3-[1-(4-Cyano-phenyl)-2-methyl-prop-(E)-ylidene]-2-oxo-2,3-dihydro-indol-1-ylmethyl}-pyridine-2-carboxylic acid

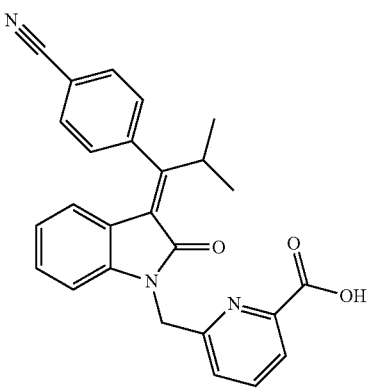 [SMILES: CC(C)/C(=C1\C(=O)N(Cc2cccc(C(=O)O)n2)c2ccccc21)c1ccc(C#N)cc1]

The title compound was prepared in analogy to Example 94 starting from 6-{3-[1-(4-cyano-phenyl)-2-methyl-prop-(E)-ylidene]-2-oxo-2,3-dihydroindol-1-ylmethyl}-pyridine-2-carboxylic acid methyl ester. $^1$H NMR (400 MHz, MeOD)

δppm 1.06 (d, 6H) 4.95-5.08 (m, 1H) 5.25 (s, 2H) 5.64 (d, 1H) 6.63 (t, 1H) 6.89 (d, 1H) 7.09 (t, 1H) 7.46 (d, 3H) 7.90-8.00 (m, 3H) 8.09 (d, 1H).

Example 98

3-{3-[1-(4-Chloro-phenyl)-2,2-dimethyl-prop-(Z)-ylidene]-2-oxo-2,3-dihydro-indol-1-ylmethyl}-benzoic acid

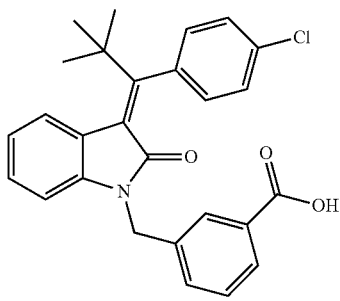 [SMILES: CC(C)(C)/C(=C1/C(=O)N(Cc2cccc(C(=O)O)c2)c2ccccc21)c1ccc(Cl)cc1]

The title compound was prepared in analogy to Example 94 starting from 3-{3-[1-(4-chloro-phenyl)-2,2-dimethyl-prop-(Z)ylidene]-2-oxo-2,3-dihydro-indol-1-ylmethyl}-benzoic acid methyl ester. $^1$H NMR (400 MHz, DMSO-$d_6$) δppm 1.32 (s, 9H) 4.86 (s, 2H) 6.95 (d, J=7.58 Hz, 1H) 7.04 (d, J=8.59 Hz, 2H) 7.13 (t, 1H) 7.29 (t, 1H) 7.38-7.42 (m, 2H) 7.44 (d, J=5.05 Hz, 2H) 7.77-7.84 (m, 2H) 7.88 (d, J=7.83 Hz, 1H) 13.01 (s, 1H).

Example 99

3-{3-[1-(4-Cyano-phenyl)-2,2-dimethyl-prop-(E)-ylidene]-2-oxo-2,3-dihydro-indol-1-ylmethyl}-benzoic acid

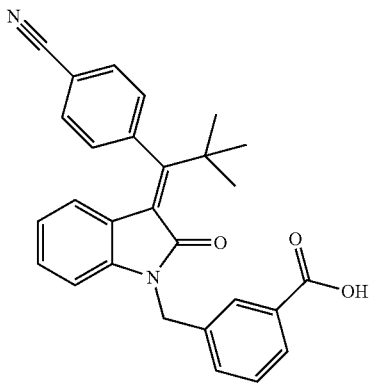

The title compound was prepared in analogy to Example 94 starting from 3-{3-[1-(4-cyano-phenyl)-2,2-dimethyl-prop-(E)-ylidene]-2-oxo-2,3-dihydro-indol-1ylmethyl}-benzoic acid methyl ester. $^1$H NMR (400 MHz, DMSO-$d_6$) δppm 1.35 (s, 9H) 5.06 (s, 2H) 5.19 (d, J=7.83 Hz, 1H) 6.57 (t, J=7.45 Hz, 1H) 6.89 (d, J=7.58 Hz, 1H) 7.07 (t, J=7.45 Hz, 1H) 7.41-7.51 (m, 3H) 7.56 (d, 1H) 7.84 (d, J=7.58 Hz, 1H) 7.93 (s, 1H) 8.03 (d, J=8.34 Hz, 2H).

Example 100

3-{3-[1-(4-Chloro-phenyl)-2,2-dimethyl-prop-(E)-ylidene]-2-oxo-2,3-dihydro-indol-1-ylmethyl}-benzoic acid

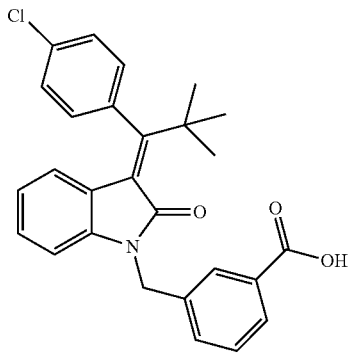 [SMILES: CC(C)(C)/C(=C1\C(=O)N(Cc2cccc(C(=O)O)c2)c2ccccc21)c1ccc(Cl)cc1]

The title compound was prepared in analogy to Example 94 starting from 3-{3-[1-(4-chloro-phenyl)-2,2-dimethyl-prop-(E)-ylidene]-2-oxo-2,3-dihydro-indol-1-ylmethyl}-benzoic acid methyl ester. $^1$H NMR (400 MHz, DMSO-$d_6$) δppm 1.35 (s, 9H) 5.06 (s, 2H) 5.30 (d, J=7.83 Hz, 1H) 6.57 (t, 1H) 6.88 (d, J=7.83 Hz, 1H) 7.06 (t, 1H) 7.22 (d, J=8.08 Hz, 2H) 7.49 (t, 1H) 7.54-7.63 (m, 3H) 7.84 (d, 1H) 7.93 (s, 1H) 12.97 (s, 1H).

Example 101

3-{3-[1-(4-Fluoro-phenyl)-2-methyl-prop-(E)-ylidene]-2-oxo-2,3-dihydro-indol-1-ylmethyl}-benzoic acid

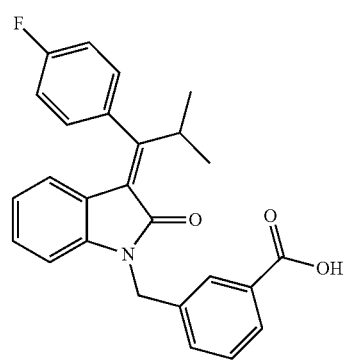 [SMILES: CC(C)/C(=C1\C(=O)N(Cc2cccc(C(=O)O)c2)c2ccccc21)c1ccc(F)cc1]

The title compound was prepared in analogy to Example 94 starting from 3-{3-[1-(4-fluoro-phenyl)-2-methyl-prop-(E)-ylidene]-2-oxo-2,3-dihydro-indol-1-ylmethyl}-benzoic acid methyl ester. $^1$H NMR (400 MHz, DMSO-$d_6$) δppm 1.01 (d, J=6.82 Hz, 6H) 4.87-4.99 (m, 1H) 5.05 (s, 2H) 5.54 (d, J=7.83 Hz, 1H) 6.63 (t, J=7.33 Hz, 1H) 6.90 (d, J=7.58 Hz, 1H) 7.09 (d, J=1.01 Hz, 1H) 7.24-7.31 (m, 2H) 7.40 (t, J=8.84 Hz, 2H)

7.49 (t, J=7.58 Hz, 1H) 7.59 (d, J=7.58 Hz, 1H) 7.85 (d, J=7.83 Hz, 1H) 7.92 (s, 1H) 13.03 (s, 1H).

Example 102

6-{3-[1-(4-Fluoro-phenyl)-2-methyl-prop-(E)-ylidene]-2-oxo-2,3-dihydro-indol-1-ylmethyl}-pyridine-2-carboxylic acid

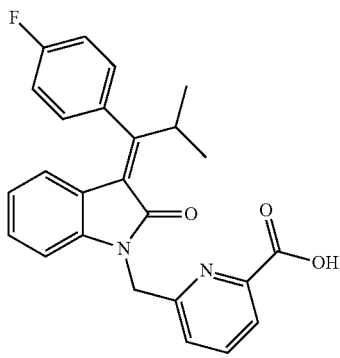 [SMILES: CC(C)/C(=C1\C(=O)N(Cc2cccc(C(=O)O)n2)c2ccccc21)c1ccc(F)cc1]

The title compound was prepared in analogy to Example 94 starting from 6-{3-[1-(4-fluoro-phenyl)-2-methyl-prop-(E)-ylidene]-2-oxo-2,3-dihydro-indol-1-ylmethyl}pyridine-2-carboxylic acid methyl ester. $^1$H NMR (400 MHz, DMSO-$d_6$) δppm 1.01 (d, J=6.82 Hz, 6H) 4.86-5.00 (m, 1H) 5.16 (br. s., 2H) 5.56 (d, J=7.83 Hz, 1H) 6.63 (t, J=7.71 Hz, 1H) 6.85 (d, J=7.33 Hz, 1H) 7.06 (t, J=7.58 Hz, 1H) 7.29 (d, J=5.56 Hz, 2H) 7.27 (d, J=5.81 Hz, 1H) 7.41 (t, J=8.72 Hz, 2H) 7.81-7.98 (m, 2H).

Example 103

3-{3-[2-Methyl-1-pyridin-3-yl-prop-(E)-ylidene]-2-oxo-2,3-dihydro-indol-1-ylmethyl}-benzoic acid

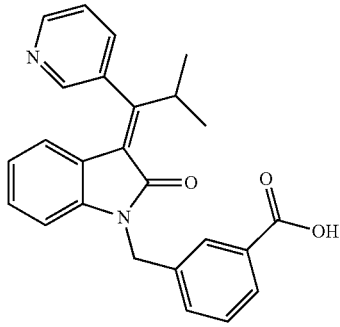 [SMILES: CC(C)/C(=C1\C(=O)N(Cc2cccc(C(=O)O)c2)c2ccccc21)c1cccnc1]

The title compound was prepared in analogy to Example 94 starting from 3-{3-[2-methyl-1-pyridin-3-yl-prop-(E)-ylidene]-2-oxo-2,3-dihydro-indol-1-ylmethyl}-benzoic acid methyl ester. $^1$H NMR (400 MHz, MeOD) δppm 1.13 (t, J=7.71 Hz, 6H) 5.01-5.14 (m, 1H) 5.10 (s, 2H) 5.59 (d, J=7.83 Hz, 1H) 6.62 (t, J=7.71 Hz, 1H) 6.83 (d, J=7.83 Hz, 1H) 7.11 (t, J=7.71 Hz, 1H) 7.47 (t, J=7.71 Hz, 1H) 7.59 (d, J=7.58 Hz, 1H) 7.84 (br. s., 1H) 7.93-8.05 (m, 2H) 7.96 (s, 1H) 8.58 (br. s., 1H) 8.85 (br. s., 1H).

Example 104

3-{3-[1-(4-Chloro-phenyl)-1-cyclohexyl-meth-(E)-ylidene]-2-oxo-2,3-dihydro-indol-1-ylmethyl}-benzoic acid

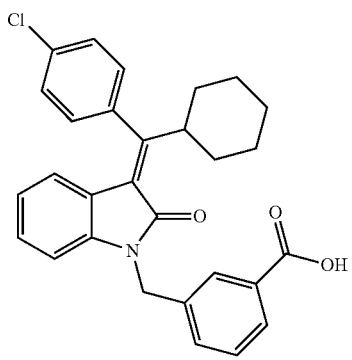 [SMILES: O=C(O)c1cccc(CN2C(=O)/C(=C(/c3ccc(Cl)cc3)C3CCCCC3)c3ccccc32)c1]

The title compound was prepared in analogy to Example 94 starting from 3-{3-[1-(4-chloro-phenyl)-1-cyclohexyl-meth-(E)-ylidene]-2-oxo-2,3-dihydro-indol-1-ylmethyl}-benzoic acid methyl ester. $^1$H NMR (CDCl$_3$, 300 MHz) δppm 8.09 (s, 1H), 8.02 (d, 1H), 7.57 (d, 1H), 7.41-7.50 (m, 3H), 7.11 (d, 2H), 7.03 (t, 1H), 6.60-6.64 (m, 2H), 5.73 (d, 1H), 5.05 (s, 2H), 4.63 (m, 1H), 1.44-1.81 (m, 6H), 1.01-1.18 (m, 4H).

Example 105

3-{3-[2-Methyl-1-(4-trifluoromethyl-phenyl)-prop-(E)-ylidene]-2-oxo-2,3-dihydro-indol-1-ylmethyl}-benzoic acid

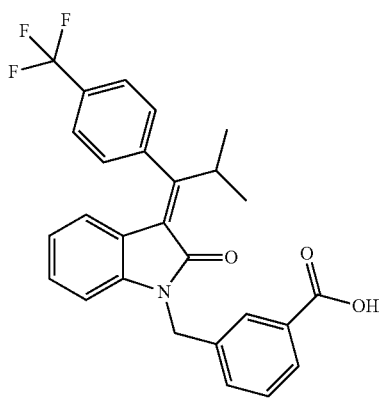 [SMILES: CC(C)/C(=C1\C(=O)N(Cc2cccc(C(=O)O)c2)c2ccccc21)c1ccc(C(F)(F)F)cc1]

The title compound was prepared in analogy to Example 94 starting from 3-{3-[2-methyl-1-(4-trifluoromethyl-phenyl)-prop-(E)-ylidene]-2-oxo-2,3-dihydro-indol-1-ylmethyl}-benzoic acid methyl ester. $^1$H NMR (CDCl$_3$, 300 MHz) δppm 8.08 (s, 1H), 8.00 (d, 1H), 7.77 (d, 2H), 7.58 (d, 1H), 7.44 (t, 1H), 7.31 (d, 2H), 7.03 (t, 1H), 6.63 (d, 1H), 6.58 (t, 1H), 5.58 (d, 1H), 5.04-5.08 (m, 3H), 1.16 (s, 3H), 1.13 (s, 1H).

Example 106

3-{3-[2-Methyl-1-thiophen-3-yl-prop-(E)-ylidene]-2-oxo-2,3-dihydro-indol-1-ylmethyl}-benzoic acid

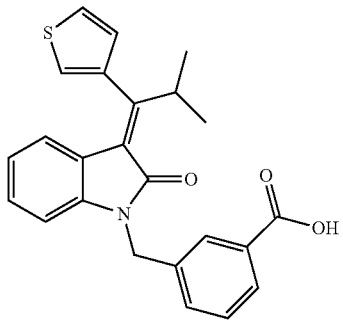 [SMILES: CC(C)/C(=C1\C(=O)N(Cc2cccc(C(=O)O)c2)c2ccccc21)c1ccsc1]

The title compound was prepared in analogy to Example 94 starting from 3-{3-[2-methyl-1-thiophen-3-yl-prop-(E)-ylidene]-2-oxo-2,3-dihydro-indol-1-ylmethyl}-benzoic acid methyl ester. $^1$H NMR (CDCl$_3$, 300 MHz) δppm 8.08 (s, 1H), 8.01 (d, 1H), 7.77 (d, 2H), 7.58 (d, 1H), 7.44 (t, 1H), 7.31 (d, 2H), 7.03 (t, 1H), 6.63 (d, 1H), 6.58 (t, 1H), 5.58 (d, 1H), 5.04-5.08 (m, 3H), 1.10 (s, 3H), 1.07 (s, 3H).

Example 107

3-{5-Chloro-3-[2-methyl-1-(4-trifluoromethyl-phenyl)-prop-(E)-ylidene]-2-oxo-2,3-dihydro-indol-1-ylmethyl}-benzoic acid

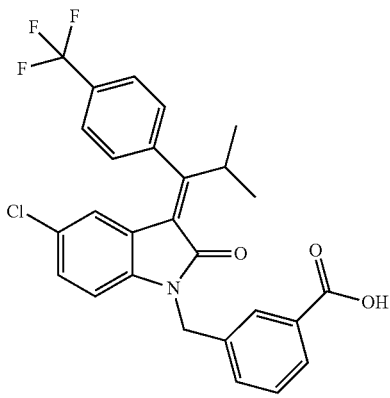 [SMILES: CC(C)/C(=C1\C(=O)N(Cc2cccc(C(=O)O)c2)c2ccc(Cl)cc21)c1ccc(C(F)(F)F)cc1]

The title compound was prepared in analogy to Example 94 starting from 3-{5-chloro-3-[2-methyl-1-(4-trifluoromethyl phenyl)-prop-(E)-ylidene]-2-oxo-2,3-dihydro-indol-1-ylmethyl}-benzoic acid methyl ester. $^1$H NMR (300 Hz, CDCl$_3$): δppm 1.11 (d, 6H), 5.00-5.04 (m, 1H), 5.01 (s, 2H), 5.40 (d, 1H), 6.51 (d, 1H), 6.98 (dd, 1H), 7.28 (d, 2H), 7.42 (t, 1H), 7.56 (m, 1H), 7.81 (d, 2H), 8.01-8.04 m, 2H).

Example 108

3-{3-[1-(4-Acetyl-phenyl)-2-methyl-prop-(E)-ylidene]-2-oxo-2,3-dihydro-indol-1-ylmethyl}-benzoic acid

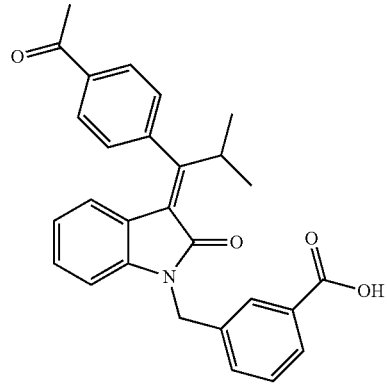 [SMILES: CC(=O)c1ccc(/C(=C2/C(=O)N(Cc3cccc(C(=O)O)c3)c3ccccc32)C(C)C)cc1]

The title compound was prepared in analogy to Example 94 starting from 3-{3-[1-(4-acetyl-phenyl)-2-methyl-prop-(E)-ylidene]-2-oxo-2,3-dihydro-indol-1-ylmethyl}-benzoic acid methyl ester. $^1$H NMR (CDCl$_3$, 300 MHz) δppm 8.00-8.12 (m, 3H), 7.72 (d, 1H), 7.57 (d, 1H), 7.44 (t, 1H), 7.29 (d, 2H), 7.02 (t, 1H), 6.62 (d, 1H), 6.55 (t, 1H), 5.63 (d, 2H), 5.04 (m, 3H), 2.70 (s, 3H), 1.10 (s, 3H), 1.08 (s, 3H).

Example 109

N-(3-{3-[1-(4-Chloro-phenyl)-2-methyl-propylidene]-2-oxo-2,3-dihydro-indol-1-ylmethyl}-benzoyl)-methanesulfonamide

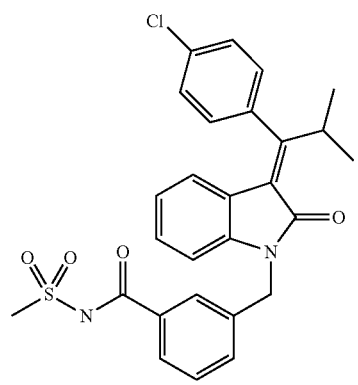 [SMILES: CC(C)/C(=C1\C(=O)N(Cc2cccc(C(=O)NS(C)(=O)=O)c2)c2ccccc21)c1ccc(Cl)cc1]

A mixture of 3-{3-[1-(4-chloro-phenyl)-2-methyl-propylidene]-2-oxo-2,3-dihydro-indol-1-ylmethyl}-benzoic acid (0.22 g, 0.51 mmol), 1-(3-dimethylaminopropyl)-3-ethylcarbodiimide hydrochloride (0.20 g, 1.02 mmol), methylsulfonamide (97 mg, 1.02 mmol), DMAP (12.2 mg, 0.10 mmol) in dichloromethane (20 ml) was stirred for 72 hours. The organic solution washed with brine (10 ml) then dried over sodium sulfate. After removal of solvent, the residue was dissolved in 2 ml DMF for prepared HPLC to give the product N-(3-{3-[1-(4-chloro-phenyl)-2-methyl-propylidene]-2-oxo-2,3-dihydro-indol-1-ylmethyl}-benzoyl)-methanesulfonamide (100 mg, 38%) as yellow solid. $^1$H NMR (400 MHz, DMSO-d$_6$) δ ppm 1.21 (d, J=6.82 Hz, 6H) 3.50 (s, 3H) 5.00-5.12 (m, 1H) 5.17 (s, 2H) 5.52 (s, 1H) 5.84 (d, J=7.83 Hz, 1H) 6.75 (t, J=7.83 Hz, 1H) 6.85 (d, J=7.83 Hz, 1H) 7.17 (t, J=7.20 Hz, 1H) 7.28 (d, J=8.59 Hz, 2H) 7.60 (t, J=7.71 Hz, 1H) 7.65 (d, J=8.34 Hz, 2H) 7.70 (d, J=7.83 Hz, 1H) 7.94 (d, J=7.83 Hz, 1H) 8.02 (s, 1H). MS calcd. for C$_{27}$H$_{25}$ClN$_2$O$_4$S 508.5, obsd. (ESI$^+$) [(M+H)$^+$] 509.2.

Example 110

N-(3-{3-[1-(4-Chloro-phenyl)-2,2-dimethyl-prop-(E)-ylidene]-2-oxo-2,3-dihydro-indol-1-ylmethyl}-benzoyl)-methanesulfonamide

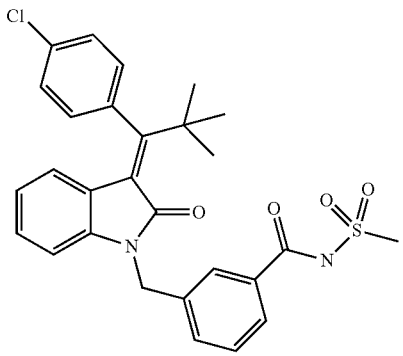 [SMILES: CC(C)(C)/C(=C1\C(=O)N(Cc2cccc(C(=O)NS(C)(=O)=O)c2)c2ccccc21)c1ccc(Cl)cc1]

The title compound was prepared in analogy to Example 109 starting from 3-{3-[1-(4-chloro-phenyl)-2,2-dimethyl-prop-(E)-ylidene]-2-oxo-2,3-dihydro-indol-1-ylmethyl}-benzoic acid. $^1$H NMR (400 MHz, MeOD) δppm 1.44 (s, 9H) 3.11 (s, 3H) 5.05 (s, 2H) 5.41 (d, J=7.83 Hz, 1H) 6.52 (t, 1H) 6.74 (d, J=7.58 Hz, 1H) 7.00 (t, 1H) 7.12-7.21 (m, 2H) 7.30-7.39 (m, 2H) 7.51-7.60 (m, 2H) 7.89-7.97 (m, 1H) 8.04 (s, 1H).

Example 111

N-(3-{3-[1-(4-Chloro-phenyl)-2,2-dimethyl-prop-(Z)-ylidene]-2-oxo-2,3-dihydro-indol-1-ylmethyl}-benzoyl)-methanesulfonamide

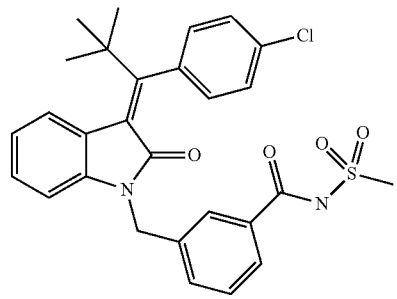 [SMILES: CC(C)(C)/C(=C1/C(=O)N(Cc2cccc(C(=O)NS(C)(=O)=O)c2)c2ccccc21)c1ccc(Cl)cc1]

The title compound was prepared in analogy to Example 109 starting from 3-{3-[1-(4-chloro-phenyl)-2,2-dimethyl-prop-(Z)-ylidene]-2-oxo-2,3-dihydro-indol-1-ylmethyl}-benzoic acid. $^1$H NMR (400 MHz, DMSO-d$_6$) δppm 1.32 (s, 9H) 3.34 (s, 3H) 4.84 (s, 2H) 6.93 (d, J=7.83 Hz, 1H) 7.04 (d, J=8.34 Hz, 2H) 7.12 (t, J=7.33 Hz, 1H) 7.27 (t, J=7.45 Hz, 1H) 7.37-7.47 (m, 4H) 7.78-7.85 (m, 2H) 7.88 (d, J=8.08 Hz, 1H).

Example 112

Evaluation of AMPK Modulator by Analysis of AMPK and ACC Phosphorylation

This method evaluates endogenous expression and phosphorylation of AMP-activated protein kinase (AMPK) and acetyl CoA carboxylase (ACC) in L6 cell line using Western blot analysis. It is used to determine the potency and efficacy of small molecular AMPK modulators. L6 cells (ATCC) are cultured and maintained at DMEM (high glucose, Gibco, BRL) with 10% fetal bovine serum (FBS, Hyclone). In an assay, cells are plated at 3×10$^6$ per plate in 10 ml on a cm dish and they reach subconfluent of 70-80% within 24 hrs. The cells are serum starved overnight prior to be treated with an AMPK modulator. The compound concentration typically ranges from 0 to 100 μM and treat the cells for 1-4 hrs. Once the incubation is completed, the medium is aspirated and the cell layer is gently rinsed with 2 ml of ice-cold PBS. 500 μl of lysis buffer containing 150 mM NaCl, 5 mM EDTA, 2 mM EGTA, 25 mM NaF, 2 mM Na$_3$VO$_4$, 1 mg/ml of Pefabloc, 1% Triton X-100, and a Roche Complete Protease Inhibitor Tablet is added and incubated on ice for 10 min. The cell lysate is harvested and subsequently centrifuged at 12,000 rpm for 10 min at 4° C. The supernatant is saved and its protein concentration is determined using Quick Start Bradford protein quantification kit (Bio-Rad). 40 μg is loaded for 7.5% SDS-PAGE analysis and subsequently blotted to PVDF membrane following a standard procedure. The membrane is treated with a blocking buffer (5% nonfat milk) for 1 h at room temperature in agitation. The levels of phospho-AMPK and phospho-ACC are determined using phospho-AMPKα (Thr172)(40H9) rabbit mAb (Cell Signaling) and phospho-acetyl CoA carboxylase(Ser79) antibody (Cell Signaling) as primary antibodies by incubating the blot at 4° C. overnight. The blots are stripped and re-probed using acetyl CoA carboxylase (C83B10) rabbit mAb (Cell signaling), AMPKα (23A3) rabbit mAb (Cell Signaling), and β-actin antibody (Cell Signaling) to determine the whole protein level of ACC, AMPK and β-actin, respectively. Each protein band in a blot is visualized via ECL Plus Western blotting detection kit (Amersham) and quantified by the scan analysis. The EC$_{50}$ value, defined as an activator concentration that produces half of the maximal activation effect, and Emax, defined as the maximal activation effect at the infinite activator concentration, are determined semi-quantitatively and recorded. All the compounds of formula (I) are active in the foregoing AMPK and ACC phosphorylation assay.

Example 113

Scintillation Proximity Assay

Preparation of Enzymes

Recombinant human AMPK α1β1γ1, α2β1γ1 or AMPK α subunit truncations α1(1-335), α1(1-394) and α2(1-394) were constructed, expressed and purified as described previously (Pang, T., Zhang, Z. S., Gu, M., Qiu, B. Y., Yu, L. F., Cao, P. R., Shao, W., Su, M. B., Li, J. Y., Nan, F. J., and Li, J. (2008)). Rat liver AMPK heterotrimer enzyme was obtained from Upstate (Billerica, Mass., U.S.A.).

Scintillation Proximity Assay

Before the Scintillation Proximity Assay (SPA) assay, 200 nM recombinant AMPK proteins (α1β1γ1, α2β1γ1, α1(1-335), α1(1-394) or α2(1-394)) were fully phosphorylated as described previously (Pang et al., 2008). SPA reactions were performed in 96-well plates at a final volume of 50l containing 20 mM Tris-HCl pH 7.5, 5 mM MgCl$_2$, 1 mM DTT, 2 μM biotin-SAMS, 2 μM ATP, 0.2 μCi/well [γ-$^{33}$P]ATP, and various amount of activator. Reactions were initiated by the addition of 50 nM recombinant AMPK proteins to the reaction solutions and incubated at 30° C. for 2 hr. After that, reactions were terminated by the addition of 40l stop solution containing 80 μg streptavidin-coated SPA beads per well, 50 mM EDTA, 0.1% Triton X-100 in PBS, pH 7.5 and incubated for 1 hr. Finally, a 160 ul suspension solution containing 2.4 M CsCl, 50 mM EDTA, and 0.1% Triton X-100 in PBS (pH 7.5) was added to the reaction solution to suspend SPA beads completely. SPA signals were determined with a Wallac MicroBeta plate counter (PerkinElmer) 30 min later for calculation of the amount of product formed. The amount of products formed in 2 hr was plotted against activator concentrations to determine the effective concentration of the activator (EC50) required for 50% of maximal enzyme activity.

Compounds as described above have EC50 values between 0.5 uM and 50 uM, preferred compounds have EC50 values between 0.5 uM and 10 uM, particularly preferred compounds have EC50 values between 0.5 uM and 1 uM. These results have been obtained by using the foregoing Scintillation Proximity Assay (uM means microMolar).

The EC50 of representative compounds of formula (I) are reported in the following table.

| Example No. | EC50 (uM) |
|---|---|
| 1 | 2.21 |
| 2 | 1.49 |
| 3 | 5.61 |
| 4 | 5.25 |
| 5 | 2.3 |
| 6 | 1.51 |
| 7 | 1.54 |
| 8 | 6.47 |
| 9 | 2.16 |
| 10 | 4.44 |
| 11 | 3.11 |
| 12 | 5.34 |
| 13 | 1.86 |
| 14 | 4.34 |
| 15 | 2.47 |
| 16 | 1.53 |
| 17 | 2.34 |
| 18 | 5.66 |
| 19 | 1 |
| 20 | 1.76 |
| 21 | 6.07 |
| 22 | 4.13 |
| 23 | 6.97 |
| 24 | 4.82 |
| 25 | 2.73 |
| 26 | 1.25 |
| 27 | 2.73 |
| 28 | 0.8 |
| 29 | 2.36 |
| 30 | 1.65 |
| 31 | 0.77 |
| 32 | 10.52 |
| 33 | 5.56 |
| 34 | 1.8 |
| 35 | 2.95 |
| 36 | 3.69 |
| 37 | 4.49 |
| 38 | 2.91 |
| 39 | 1.57 |
| 41 | 4.51 |
| 42 | 4.5 |
| 43 | 3.23 |
| 44 | 1.21 |
| 45 | 1.89 |
| 46 | 4.02 |
| 47 | 2.38 |
| 48 | 3.15 |
| 49 | 1.75 |
| 50 | 5.89 |
| 51 | 1.42 |
| 52 | 6.55 |
| 53 | 5.89 |
| 54 | 5.14 |
| 55 | 2.94 |
| 56 | 4.24 |
| 57 | 2.17 |
| 58 | 4.87 |
| 59 | 5.19 |
| 60 | 1.24 |
| 61 | 4.93 |
| 62 | 2.33 |
| 63 | 3.24 |
| 64 | 6.63 |
| 65 | 3.41 |
| 66 | 2.44 |
| 67 | 1.27 |
| 68 | 2.12 |
| 69 | 2.2 |
| 70 | 4.96 |
| 71 | 4.02 |
| 72 | 3.3 |
| 73 | 5.14 |
| 74 | 3.17 |
| 75 | 1.84 |
| 76 | 5.14 |
| 77 | 2.58 |
| 78 | 1.6 |
| 79 | 1.69 |
| 80 | 5.8 |
| 81 | 4.74 |
| 82 | 1.6 |
| 85 | 4.9 |
| 86 | 7.88 |
| 87 | 10.65 |
| 88 | 2.59 |
| 104 | 4.63 |
| 105 | 2.95 |
| 106 | 1.61 |
| 107 | 0.66 |
| 108 | 3.25 |

Example A

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A method of treatment of a disease or disorder selected from the group consisting of obesity, dyslipidemia, hyperglycemia, type 1 diabetes and type 2 diabetes, said method comprising administering to a patient in need thereof an effective amount of a compound of formula (I),

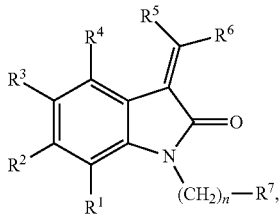

wherein
$R^1$ is selected from the group consisting of: hydrogen, halogen, alkoxy, cyano, haloalkyl, alkylsulfanyl, aminosulfonyl, alkylsulfonyl, haloalkoxy and alkylcarbonyl,
$R^2$ is selected from the group consisting of: hydrogen, halogen, alkoxy, cyano, haloalkyl, alkylsulfanyl, aminosulfonyl, alkylsulfonyl, haloalkoxy and alkylcarbonyl,
$R^3$ is selected from the group consisting of: hydrogen, halogen, alkoxy, cyano, haloalkyl, alkylsulfanyl, aminosulfonyl, alkylsulfonyl, haloalkoxy and alkylcarbonyl,
$R^4$ is selected from the group consisting of: hydrogen, halogen, alkoxy, cyano, haloalkyl, alkylsulfanyl, aminosulfonyl, alkylsulfonyl, haloalkoxy and alkylcarbonyl,
$R^5$ is selected from the group consisting of: alkyl, hydroxyalkyl, cycloalkyl, phenylalkyl, halophenylalkyl, phenyl, substituted phenyl, thiophenyl and pyridinyl, wherein said substituted phenyl is phenyl substituted with one to three substituents independently selected from the group consisting of alkyl, alkoxy, halogen, cyano, haloalkyl, alkylsulfanyl, aminosulfonyl, alkylsulfonyl, haloalkoxy and alkylcarbonyl,
$R^6$ is selected from the group consisting of: alkyl, hydroxyalkyl, cycloalkyl, phenylalkyl, halophenylalkyl, phenyl, substituted phenyl, thiophenyl and pyridinyl, wherein said substituted phenyl is phenyl substituted with one to three substituents independently selected from the group consisting of alkyl, alkoxy, halogen, cyano, haloalkyl, alkylsulfanyl, aminosulfonyl, alkylsulfonyl, haloalkoxy and alkylcarbonyl,
$R^7$ is selected from the group consisting of: substituted phenyl, pyridinyl, substituted pyridinyl, thiazolyl, substituted thiazolyl and carboxy, wherein said substituted phenyl is phenyl substituted with one to three substituents independently selected from the group consisting of alkyl, hydroxy, alkoxy, carboxy, alkoxycarbonylalkyl, alkylaminocarbonyl, carboxyalkoxy, alkoxycarbonyl, alkoxycarbonylalkoxy and alkylsulfonylaminocarbonyl, and said substituted pyridinyl and said substituted thiazolyl are, respectively, pyridinyl and thiazolyl substituted with alkoxycarbonyl or carboxy; and
n is 0 or 1;
or a pharmaceutically acceptable salt or ester thereof;
with the provisos that:
$R^5$ and $R^6$ are not both methoxyphenyl at the same time; and
when one of $R^5$ and $R^6$ is phenyl and the other one is phenyl, methylphenyl or alkoxyphenyl, $R^7$ is alkoxycarbonylphenyl.

2. The method according to claim 1, wherein $R^1$ is selected from the group consisting of: hydrogen, halogen and alkoxy.

3. The method according to claim 1, wherein $R^1$ is selected from the group consisting of: hydrogen, fluoro and chloro.

4. The method according to claim 1, wherein $R^2$ is selected from the group consisting of: hydrogen, halogen and alkoxy.

5. The method according to claim 1, wherein $R^2$ is hydrogen or fluoro.

6. The method according to claim 1, wherein $R^3$ is selected from the group consisting of: hydrogen, halogen and alkoxy.

7. The method according to claim 1, wherein $R^3$ is selected from the group consisting of: hydrogen, fluoro, chloro and methoxy.

8. The method according to claim 1, wherein $R^4$ is selected from the group consisting of: hydrogen, halogen and alkoxy.

9. The method according to claim 1, wherein $R^4$ is hydrogen or fluoro.

10. The method according to claim 1, wherein $R^5$ is selected from the group consisting of: alkyl, halophenylalkyl, phenyl, substituted phenyl, thiophenyl and pyridinyl, wherein said substituted phenyl is phenyl substituted with one to three substituents independently selected from the group consisting of alkyl, alkoxy, halogen, cyano, haloalkyl, alkylsulfanyl, aminosulfonyl, alkylsulfonyl, haloalkoxy and alkylcarbonyl.

11. The method according to claim 1, wherein $R^5$ is halophenyl or cyanophenyl.

12. The method according to claim 1, wherein $R^5$ is chlorophenyl or cyanophenyl.

13. The method according to claim 1, wherein $R^6$ is selected from the group consisting of: alkyl, hydroxyalkyl, cycloalkyl, phenyl and halophenyl.

14. The method according to claim 1, wherein $R^6$ is alkyl or phenyl.

15. The method according to claim 1, wherein $R^6$ is isopropyl or phenyl.

16. The method according to claim 1, wherein $R^7$ is selected from the group consisting of: substituted phenyl, substituted pyridinyl, substituted thiazolyl and carboxy, wherein said substituted phenyl is phenyl substituted with one to three substituents independently selected from the group consisting of alkyl, hydroxy, alkoxy, carboxy, alkoxycarbonylalkyl, alkylaminocarbonyl, carboxyalkoxy, alkoxycarbonyl, alkoxycarbonylalkoxy and alkylsulfonylaminocarbonyl, and said substituted pyridinyl and said substituted thiazolyl are, respectively, pyridinyl and thiazolyl substituted with alkoxycarbonyl or carboxy.

17. The method according to claim 1, wherein $R^7$ is selected from the group consisting of: carboxyphenyl, alkoxycarbonylphenyl and carboxypyridinyl.

18. The method according to claim 1, wherein $R^7$ is selected from the group consisting of: carboxyphenyl, methoxycarbonylphenyl and carboxypyridinyl.

19. The method according to claim 1 selected from the group consisting of:
- 3-{2-Oxo-3-[1-phenyl-eth-(E)-ylidene]-2,3-dihydro-indol-1-yl}-benzoic acid ethyl ester;
- (3-{2-Oxo-3-[1-phenyl-eth-(E)-ylidene]-2,3-dihydro-indol-1-yl}-phenyl)-acetic acid methyl ester;
- 2-Methyl-5-{2-oxo-3-[1-phenyl-eth-(E)-ylidene]-2,3-dihydro-indol-1-yl}-benzoic acid methyl ester;
- [2-Oxo-3-(1-phenyl-ethylidene)-2,3-dihydro-indol-1-yl]-acetic acid;
- 3-{3-[1-(4-Chloro-phenyl)-1-phenyl-meth-(E)-ylidene]-2-oxo-2,3-dihydro-indol-1-ylmethyl}-benzoic acid methyl ester;
- 3-{3-[1-(4-Chloro-phenyl)-1-phenyl-meth-(E)-ylidene]-7-fluoro-2-oxo-2,3-dihydro-indol-1-ylmethyl}-benzoic acid methyl ester;
- 3-(3-Benzhydrylidene-2-oxo-2,3-dihydro-indol-1-ylmethyl)-benzoic acid methyl ester;
- 3-{3-[1-(4-Methoxy-phenyl)-1-phenyl-meth-(E)-ylidene]-2-oxo-2,3-dihydro-indol-1-ylmethyl}-benzoic acid methyl ester;
- 3-{2-Oxo-3-[1-phenyl-1-p-tolyl-meth-(E)-ylidene]-2,3-dihydro-indol-1-ylmethyl}-benzoic acid methyl ester;
- 3-{3-[1-(4-Chloro-phenyl)-1-(2-methoxy-phenyl)-meth-(Z)-ylidene]-2-oxo-2,3-dihydro-indol-1-ylmethyl}-benzoic acid methyl ester;
- 3-{3-[1-(4-Cyano-phenyl)-1-phenyl-meth-(E)-ylidene]-2-oxo-2,3-dihydro-indol-1-ylmethyl}-benzoic acid methyl ester;

and pharmaceutically acceptable salts or esters thereof.

20. The method according to claim 1 selected from the group consisting of:
- 3-{3-[1-(4-Chloro-phenyl)-1-phenyl-meth-(E)-ylidene]-2-oxo-2,3-dihydro-indol-1-ylmethyl}-benzoic acid;
- 3-{3-[1-(4-Chloro-phenyl)-2-methyl-prop-(E)-ylidene]-2-oxo-2,3-dihydro-indol-1-ylmethyl}-benzoic acid;
- 3-{3-[1-(4-Cyano-phenyl)-2-methyl-prop-(E)-ylidene]-2-oxo-2,3-dihydro-indol-1-ylmethyl}-benzoic acid;
- 6-{3-[1-(4-Chloro-phenyl)-2-methyl-prop-(E)-ylidene]-2-oxo-2,3-dihydro-indol-1-ylmethyl}-pyridine-2-carboxylic acid;
- 6-{3-[1-(4-Cyano-phenyl)-2-methyl-prop-(E)-ylidene]-2-oxo-2,3-dihydro-indol-1-ylmethyl}-pyridine-2-carboxylic acid.

21. The method according to claim 1 selected from the group consisting of:
- 3-{2-Oxo-3-[1-phenyl-1-(4-trifluoromethyl-phenyl)-meth-(E)-ylidene]-2,3-dihydro-indol-1-ylmethyl}-benzoic acid methyl ester;
- 3-{3-[1-(3-Chloro-4-fluoro-phenyl)-1-phenyl-meth-(E)-ylidene]-2-oxo-2,3-dihydro-indol-1-ylmethyl}-benzoic acid methyl ester;
- 3-{2-Oxo-3-[1-phenyl-1-(3,4,5-trimethoxy-phenyl)-meth-(E)-ylidene]-2,3-dihydro-indol-1-ylmethyl}-benzoic acid methyl ester;
- 3-{3-[1-(3,4-Difluoro-phenyl)-1-phenyl-meth-(E)-ylidene]-2-oxo-2,3-dihydro-indol-1-ylmethyl}-benzoic acid methyl ester;
- 3-{3-[1-(3-Chloro-phenyl)-1-phenyl-meth-(E)-ylidene]-2-oxo-2,3-dihydro-indol-1-ylmethyl}-benzoic acid methyl ester;
- 3-{3-[1-(2-Chloro-phenyl)-1-phenyl-meth-(E)-ylidene]-2-oxo-2,3-dihydro-indol-1-ylmethyl}-benzoic acid methyl ester;
- 3-{3-[1-(4-Chloro-phenyl)-1-phenyl-meth-(E)-ylidene]-5-fluoro-2-oxo-2,3-dihydro-indol-1-ylmethyl}-benzoic acid methyl ester;
- 3-{3-[1-(3,5-Dichloro-phenyl)-1-phenyl-meth-(E)-ylidene]-2-oxo-2,3-dihydro-indol-1-ylmethyl}-benzoic acid methyl ester;
- 3-{3-[1-(2,3-Dichloro-phenyl)-1-phenyl-meth-(E)-ylidene]-2-oxo-2,3-dihydro-indol-1-ylmethyl}-benzoic acid methyl ester;
- 4-{3-[1-(4-Chloro-phenyl)-1-phenyl-meth-(E)-ylidene]-2-oxo-2,3-dihydro-indol-1-ylmethyl}-benzoic acid methyl ester;

and pharmaceutically acceptable salts or esters thereof.

22. The method according to claim 1 selected from the group consisting of:
- 3-{3-[1-(4-Chloro-phenyl)-1-phenyl-meth-(E)-ylidene]-5-methoxy-2-oxo-2,3-dihydro-indol-1-ylmethyl}-benzoic acid methyl ester;
- 3-{3-[1-(2-Bromo-phenyl)-1-phenyl-meth-(E)-ylidene]-2-oxo-2,3-dihydro-indol-1-ylmethyl}-benzoic acid methyl ester;
- 3-{3-[1-(2-Chloro-5-trifluoromethyl-phenyl)-1-phenyl-meth-(E)-ylidene]-2-oxo-2,3-dihydro-indol-1-ylmethyl}-benzoic acid methyl ester;
- 3-{3-[1-(4-Chloro-phenyl)-1-phenyl-meth-(E)-ylidene]-4-fluoro-2-oxo-2,3-dihydro-indol-1-ylmethyl}-benzoic acid methyl ester;
- 3-{3-[1-(4-Chloro-phenyl)-1-phenyl-meth-(E)-ylidene]-6-fluoro-2-oxo-2,3-dihydro-indol-1-ylmethyl}-benzoic acid methyl ester;
- 3-{3-[1-(3-Bromo-phenyl)-1-phenyl-meth-(E)-ylidene]-2-oxo-2,3-dihydro-indol-1-ylmethyl}-benzoic acid methyl ester;
- 3-{3-[1-(2-Methylsulfanyl-phenyl)-1-phenyl-meth-(E)-ylidene]-2-oxo-2,3-dihydro-indol-1-ylmethyl}-benzoic acid methyl ester;
- 3-{7-Chloro-3-[1-(4-chloro-phenyl)-1-phenyl-meth-(E)-ylidene]-5-fluoro-2-oxo-2,3-dihydro-indol-1-ylmethyl}-benzoic acid methyl ester;
- 3-{2-Oxo-3-[1-phenyl-1-(3-trifluoromethyl-phenyl)-meth-(E)-ylidene]-2,3-dihydro-indol-1-ylmethyl}-benzoic acid methyl ester;
- 3-{2-Oxo-3-[1-phenyl-1-(4-sulfamoyl-phenyl)-meth-(E)-ylidene]-2,3-dihydro-indol-1-ylmethyl}-benzoic acid methyl ester;

and pharmaceutically acceptable salts or esters thereof.

23. The method according to claim 1 selected from the group consisting of:
- 3-{3-[1-(2-Methanesulfonyl-phenyl)-1-phenyl-meth-(E)-ylidene]-2-oxo-2,3-dihydro-indol-1-ylmethyl}-benzoic acid methyl ester;
- 3-{2-Oxo-3-[1-phenyl-1-thiophen-3-yl-meth-(E)-ylidene]-2,3-dihydro-indol-1-ylmethyl}-benzoic acid methyl ester;
- 3-{3-[1-(4-Chloro-phenyl)-1-phenyl-meth-(Z)-ylidene]-2-oxo-2,3-dihydro-indol-1-ylmethyl}-benzoic acid methyl ester;
- 3-{3-[1-(4-Chloro-phenyl)-1-(4-trifluoromethyl-phenyl)-meth-(Z)-ylidene]-2-oxo-2,3-dihydro-indol-1-ylmethyl}-benzoic acid methyl ester;
- (4-{3-[1-(4-Chloro-phenyl)-1-phenyl-meth-(E)-ylidene]-2-oxo-2,3-dihydro-indol-1-ylmethyl}-phenoxy)-acetic acid ethyl ester;
- 3-{3-[1-(4-Chloro-phenyl)-1-phenyl-meth-(E)-ylidene]-2-oxo-2,3-dihydro-indol-1-ylmethyl}-N-isopropyl-benzamide;
- 6-{3-[1-(4-Chloro-phenyl)-1-phenyl-meth-(E)-ylidene]-2-oxo-2,3-dihydro-indol-1-ylmethyl}-nicotinic acid methyl ester;

2-{3-[1-(4-Chloro-phenyl)-1-phenyl-meth-(E)-ylidene]-2-oxo-2,3-dihydro-indol-1-ylmethyl}-thiazole-4-carboxylic acid ethyl ester;

3-[1-(4-Chloro-phenyl)-1-phenyl-meth-(E)-ylidene]-1-(4-methoxy-benzyl)-1,3-dihydro-indol-2-one;

3-[1-(4-Chloro-phenyl)-1-phenyl-meth-(E)-ylidene]-1-(3,4,5-trihydroxy-benzyl)-1,3-dihydro-indol-2-one;

and pharmaceutically acceptable salts or esters thereof.

24. The method according to claim 1 selected from the group consisting of:

3-[1-(4-Chloro-phenyl)-1-phenyl-meth-(Z)-ylidene]-1-(3,4,5-trihydroxy-benzyl)-1,3-dihydro-indol-2-one;

3-[1-(4-Chloro-phenyl)-1-phenyl-meth-(E)-ylidene]-1-(4-hydroxy-benzyl)-1,3-dihydro-indol-2-one;

3-{3-[1-(4-chloro-phenyl)-1-phenyl-meth-(E)-ylidene]-2-oxo-2,3-dihydro-indol-1-ylmethyl}-benzoic acid;

3-{3-[1-(4-Fluoro-phenyl)-1-phenyl-meth-(E)-ylidene]-2-oxo-2,3-dihydro-indol-1-ylmethyl}-benzoic acid;

3-{3-[1-(4-Methoxy-phenyl)-1-phenyl-meth-(E)-ylidene]-2-oxo-2,3-dihydro-indol-1-ylmethyl}-benzoic acid;

3-{3-[1-(4-Chloro-phenyl)-1-(2-methoxy-phenyl)-meth-(Z)-ylidene]-2-oxo-2,3-dihydro-indol-1-ylmethyl}-benzoic acid;

3-{2-Oxo-3-[1-phenyl-1-(4-trifluoromethyl-phenyl)-meth-(E)-ylidene]-2,3-dihydro-indol-1-ylmethyl}-benzoic acid;

3-{2-Oxo-3-[1-phenyl-1-(2-trifluoromethoxy-phenyl)-meth-(E)-ylidene]-2,3-dihydro-indol-1-ylmethyl}-benzoic acid;

3-{3-[1-(3-Chloro-4-fluoro-phenyl)-1-phenyl-meth-(E)-ylidene]-2-oxo-2,3-dihydro-indol-1-ylmethyl}-benzoic acid;

3-{2-Oxo-3-[1-phenyl-1-(3,4,5-trimethoxy-phenyl)-meth-(E)-ylidene]-2,3-dihydro-indol-1-ylmethyl}-benzoic acid;

and pharmaceutically acceptable salts or esters thereof.

25. The method according to claim 1 selected from the group consisting of:

3-{3-[1-(3-Chloro-phenyl)-1-phenyl-meth-(E)-ylidene]-2-oxo-2,3-dihydro-indol-1-ylmethyl}-benzoic acid;

3-{3-[1-(4-Chloro-phenyl)-1-phenyl-meth-(E)-ylidene]-5-fluoro-2-oxo-2,3-dihydro-indol-1-ylmethyl}-benzoic acid;

3-{3-[1-(3,5-Dichloro-phenyl)-1-phenyl-meth-(E)-ylidene]-2-oxo-2,3-dihydro-indol-1-ylmethyl}-benzoic acid;

3-{3-[1-(2,3-Dichloro-phenyl)-1-phenyl-meth-(E)-ylidene]-2-oxo-2,3-dihydro-indol-1-ylmethyl}-benzoic acid;

2-{3-[1-(4-Chloro-phenyl)-1-phenyl-meth-(E)-ylidene]-2-oxo-2,3-dihydro-indol-1-ylmethyl}-benzoic acid;

4-{3-[1-(4-Chloro-phenyl)-1-phenyl-meth-(E)-ylidene]-2-oxo-2,3-dihydro-indol-1-ylmethyl}-benzoic acid;

3-{3-[1-(4-Chloro-phenyl)-1-phenyl-meth-(E)-ylidene]-5-methoxy-2-oxo-2,3-dihydro-indol-1-ylmethyl}-benzoic acid;

6-{3-[1-(4-Chloro-phenyl)-1-phenyl-meth-(E)-ylidene]-2-oxo-2,3-dihydro-indol-1-ylmethyl}-nicotinic acid;

3-{3-[1-(4-Chloro-phenyl)-1-phenyl-meth-(E)-ylidene]-4-fluoro-2-oxo-2,3-dihydro-indol-1-ylmethyl}-benzoic acid;

3-{3-[1-(4-Chloro-phenyl)-1-phenyl-meth-(E)-ylidene]-6-fluoro-2-oxo-2,3-dihydro-indol-1-ylmethyl}-benzoic acid;

and pharmaceutically acceptable salts or esters thereof.

26. The method according to claim 1 selected from the group consisting of:

3-{3-[1-(2-Methylsulfanyl-phenyl)-1-phenyl-meth-(E)-ylidene]-2-oxo-2,3-dihydro-indol-1-ylmethyl}-benzoic acid;

3-{2-Oxo-3-[1-phenyl-1-pyridin-3-yl-meth-(E)-ylidene]-2,3-dihydro-indol-1-ylmethyl}-benzoic acid;

3-{3-[1-(2-Chloro-5-trifluoromethyl-phenyl)-1-phenyl-meth-(E)-ylidene]-2-oxo-2,3-dihydro-indol-1-ylmethyl}-benzoic acid;

3-{3-[1-(3,5-Bis-trifluoromethyl-phenyl)-1-phenyl-meth-(E)-ylidene]-2-oxo-2,3-dihydro-indol-1-ylmethyl}-benzoic acid;

3-{2-Oxo-3-[1-phenyl-1-(3-trifluoromethyl-phenyl)-meth-(E)-ylidene]-2,3-dihydro-indol-1-ylmethyl}-benzoic acid;

3-{2-Oxo-3-[1-phenyl-1-(4-sulfamoyl-phenyl)-meth-(E)-ylidene]-2,3-dihydro-indol-1-ylmethyl}-benzoic acid;

3-{3-[1-(4-Chloro-phenyl)-1-phenyl-meth-(Z)-ylidene]-2-oxo-2,3-dihydro-indol-1-ylmethyl}-benzoic acid;

3-{3-[1-(4-Chloro-phenyl)-1-(4-trifluoromethyl-phenyl)-meth-(Z)-ylidene]-2-OXO-2,3-dihydro-indol-1-ylmethyl}-benzoic acid;

(4-{3-[1-(4-Chloro-phenyl)-1-phenyl-meth-(E)-ylidene]-2-oxo-2,3-dihydro-indol-1-ylmethyl}-phenoxy)-acetic acid;

3-{3-[1-(4-Isopropyl-phenyl)-1-phenyl-meth-(E)-ylidene]-2-oxo-2,3-dihydro-indol-1-ylmethyl}-benzoic acid;

and pharmaceutically acceptable salts or esters thereof.

27. The method according to claim 1 selected from the group consisting of:

3-{3-[1-(3,4-Difluoro-phenyl)-1-phenyl-meth-(E)-ylidene]-2-oxo-2,3-dihydro-indol-1-ylmethyl}-benzoic acid;

3-{3-[1-(4-Chloro-phenyl)-1-phenyl-meth-(E)-ylidene]-7-fluoro-2-oxo-2,3-dihydro-indol-1-ylmethyl}-benzoic acid;

3-{5-Chloro-3-[1-(4-chloro-phenyl)-1-phenyl-meth-(E)-ylidene]-2-oxo-2,3-dihydro-indol-1-ylmethyl}-benzoic acid;

3-{3-[1-(2-Chloro-phenyl)-1-phenyl-meth-(E)-ylidene]-2-oxo-2,3-dihydro-indol-1-ylmethyl}-benzoic acid;

2-{3-[1-(4-Chloro-phenyl)-1-phenyl-meth-(E)-ylidene]-2-oxo-2,3-dihydro-indol-1-ylmethyl}-thiazole-4-carboxylic acid;

3-{3-[4-Methyl-1-phenyl-pent-(Z)-ylidene]-2-oxo-2,3-dihydro-indol-1-ylmethyl}-benzoic acid methyl ester;

3-{3-[3,3-Dimethyl-1-phenyl-but-(Z)-ylidene]-2-oxo-2,3-dihydro-indol-1-ylmethyl}-benzoic acid methyl ester;

3-{3-[2-(4-Chloro-phenyl)-1-phenyl-eth-(Z)-ylidene]-2-oxo-2,3-dihydro-indol-1-ylmethyl}-benzoic acid methyl ester;

3-{3-[3,3-Dimethyl-1-phenyl-but-(E)-ylidene]-2-oxo-2,3-dihydro-indol-1-ylmethyl}-benzoic acid methyl ester;

3-{3-[4-Methyl-1-phenyl-pent-(Z)-ylidene]-2-oxo-2,3-dihydro-indol-1-ylmethyl}-benzoic acid;

and pharmaceutically acceptable salts or esters thereof.

28. The method according to claim 1 selected from the group consisting of:

3-{3-[1-(4-Chloro-benzyl)-2-methyl-prop-(Z)-ylidene]-2-oxo-2,3-dihydro-indol-1-ylmethyl}-benzoic acid;

3-{3-[1-(4-Fluoro-phenyl)-eth-(E)-ylidene]-2-oxo-2,3-dihydro-indol-1-ylmethyl}benzoic acid;

3-{3-[1-(4-Chloro-phenyl)-2-methyl-prop-(E)-ylidene]-2-oxo-2,3-dihydro-indol-1-ylmethyl}-benzoic acid methyl ester;

3-{3-[2-Methyl-1-phenyl-prop-(E)-ylidene]-2-oxo-2,3-dihydro-indol-1-ylmethyl}-benzoic acid methyl ester;

3-{3-[1-(4-Acetyl-phenyl)-2-methyl-prop-(E)-ylidene]-2-oxo-2,3-dihydro-indol-1-ylmethyl}-benzoic acid methyl ester;

3-{3-[1-(4-Chloro-phenyl)-1-cyclohexyl-meth-(E)-ylidene]-2-oxo-2,3-dihydro-indol-1-ylmethyl}-benzoic acid methyl ester;

3-{3-[2-Methyl-1-(4-trifluoromethyl-phenyl)-prop-(E)-ylidene]-2-oxo-2,3-dihydro-indol-1-ylmethyl}-benzoic acid methyl ester;

3-{3-[1-(4-Chloro-phenyl)-2-hydroxy-2-methyl-prop-(Z)-ylidene]-2-OXO-2,3-dihydro-indol-1-ylmethyl}-benzoic acid methyl ester;

3-{3-[1-(4-Cyano-phenyl)-2-hydroxy-2-methyl-prop-(Z)-ylidene]-2-oxo-2,3-dihydro-indol-1-ylmethyl}-benzoic acid methyl ester;

3-{3-[1-(4-Chloro-phenyl)-2,2-dimethyl-prop-(Z)-ylidene]-2-Oxo-2,3-dihydro-indol-1-ylmethyl}-benzoic acid methyl ester;

and pharmaceutically acceptable salts or esters thereof.

29. The method according to claim 1 selected from the group consisting of:

3-{3-[1-(4-Cyano-phenyl)-2,2-dimethyl-prop-(E)-ylidene]-2-oxo-2,3-dihydro-indol-1-ylmethyl}-benzoic acid methyl ester;

3-{3-[1-(4-Chloro-phenyl)-2,2-dimethyl-prop-(E)-ylidene]-2-oxo-2,3-dihydro-indol-1-ylmethyl}-benzoic acid methyl ester;

3-{3-[1-(4-Chloro-phenyl)-2-methyl-prop-(E)-ylidene]-2-oxo-2,3-dihydro-indol-1-ylmethyl}-benzoic acid;

3-{3-[1-(4-Cyano-phenyl)-2-methyl-prop-(E)-ylidene]-2-Oxo-2,3-dihydro-indol-1-ylmethyl}-benzoic acid;

6-{3-[1-(4-Chloro-phenyl)-2-methyl-prop-(E)-ylidene]-2-oxo-2,3-dihydro-indol-1-ylmethyl}-pyridine-2-carboxylic acid;

6-{3-[1-(4-Cyano-phenyl)-2-methyl-prop-(E)-ylidene]-2-oxo-2,3-dihydro-indol-1-ylmethyl}-pyridine-2-carboxylic acid;

3-{3-[1-(4-Chloro-phenyl)-2,2-dimethyl-prop-(Z)-ylidene]-2-oxo-2,3-dihydro-indol-1-ylmethyl}-benzoic acid;

3-{3-[1-(4-Cyano-phenyl)-2,2-dimethyl-prop-(E)-ylidene]-2-oxo-2,3-dihydro-indol-1-ylmethyl}-benzoic acid;

3-{3-[1-(4-Chloro-phenyl)-2,2-dimethyl-prop-(E)-ylidene]-2-oxo-2,3-dihydro-indol-1-ylmethyl}-benzoic acid;

3-{3-[1-(4-Fluoro-phenyl)-2-methyl-prop-(E)-ylidene]-2-oxo-2,3-dihydro-indol-1-ylmethyl}-benzoic acid;

and pharmaceutically acceptable salts or esters thereof.

30. The method according to claim 1 selected from the group consisting of:

6-{3-[1-(4-Fluoro-phenyl)-2-methyl-prop-(E)-ylidene]-2-Oxo-2,3-dihydro-indol-1-ylmethyl}-pyridine-2-carboxylic acid;

3-{3-[2-Methyl-1-pyridin-3-yl-prop-(E)-ylidene]-2-Oxo-2,3-dihydro-indol-1-ylmethyl}-benzoic acid;

3-{3-[1-(4-Chloro-phenyl)-1-cyclohexyl-meth-(E)-ylidene]-2-oxo-2,3-dihydro-indol-1-ylmethyl}-benzoic acid;

3-{3-[2-Methyl-1-(4-trifluoromethyl-phenyl)-prop-(E)-ylidene]-2-oxo-2,3-dihydro-indol-1-ylmethyl}-benzoic acid;

3-{3-[2-Methyl-1-thiophen-3-yl)-prop-(E)-ylidene]-2-oxo-2,3-dihydro-indol-1-ylmethyl}-benzoic acid;

3-{5-Chloro-3-[2-methyl-1-(4-trifluoromethyl-phenyl)-prop-(E)-ylidene]-2-oxo-2,3-dihydro-indol-1-ylmethyl}-benzoic acid;

3-{3-[1-(4-Acetyl-phenyl)-2-methyl-prop-(E)-ylidene]-2-oxo-2,3-dihydro-indol-1-ylmethyl}-benzoic acid;

N-(3-{3-[1-(4-Chloro-phenyl)-2-methyl-prop-(E)-ylidene]-2-oxo-2,3-dihydro-indol-1-ylmethyl}-benzoyl)-methanesulfonamide;

N-(3-{3-[1-(4-Chloro-phenyl)-2,2-dimethyl-prop-(E)-ylidene]-2-oxo-2,3-dihydro-indol-1-ylmethyl}-benzoyl)-methanesulfonamide;

N-(3-{3-[1-(4-Chloro-phenyl)-2,2-dimethyl-prop-(Z)-ylidene]-2-oxo-2,3-dihydro-indol-1-ylmethyl}-benzoyl)-methanesulfonamide;

and pharmaceutically acceptable salts or esters thereof.

31. The method according to claim 1, wherein said disease or disorder is type 2 diabetes.

\* \* \* \* \*